(12) United States Patent
Urfer-Buchwalder et al.

(10) Patent No.: US 12,385,093 B2
(45) Date of Patent: Aug. 12, 2025

(54) USE OF APOE4 MOTIF-MEDIATED GENES FOR DIAGNOSIS AND TREATMENT OF ALZHEIMER'S DISEASE

(71) Applicant: SELONTERRA, INC., Belmont, CA (US)

(72) Inventors: Anne Urfer-Buchwalder, Belmont, CA (US); Roman Urfer, Belmont, CA (US)

(73) Assignee: SELONTERRA, INC., Belmont, CA (US)

( * ) Notice: Subject to any disclaimer, the term of this patent is extended or adjusted under 35 U.S.C. 154(b) by 0 days.

(21) Appl. No.: 16/470,537

(22) PCT Filed: Dec. 15, 2017

(86) PCT No.: PCT/US2017/066881
§ 371 (c)(1),
(2) Date: Jun. 17, 2019

(87) PCT Pub. No.: WO2018/112446
PCT Pub. Date: Jun. 21, 2018

(65) Prior Publication Data
US 2019/0338363 A1 Nov. 7, 2019

Related U.S. Application Data

(60) Provisional application No. 62/435,815, filed on Dec. 18, 2016.

(51) Int. Cl.
*C12Q 1/6883* (2018.01)
*G01N 33/68* (2006.01)

(52) U.S. Cl.
CPC ....... *C12Q 1/6883* (2013.01); *G01N 33/6896* (2013.01); *C12Q 2600/106* (2013.01); *C12Q 2600/136* (2013.01); *C12Q 2600/156* (2013.01); *C12Q 2600/158* (2013.01); *C12Q 2600/178* (2013.01); *G01N 2800/2821* (2013.01)

(58) Field of Classification Search
CPC ............ C12Q 1/6883; C12Q 2600/106; C12Q 2600/136; C12Q 2600/156; C12Q 2600/158; C12Q 2600/178; G01N 33/6896; G01N 2800/2821; A61P 25/28
See application file for complete search history.

(56) References Cited

U.S. PATENT DOCUMENTS

| | | |
|---|---|---|
| 5,935,781 A | 8/1999 | Nadeau et al. |
| 2002/0107197 A1 | 8/2002 | Xu et al. |
| 2015/0141491 A1 | 5/2015 | Nagy |
| 2016/0251665 A1 | 9/2016 | Lindquist et al. |

FOREIGN PATENT DOCUMENTS

| | | | |
|---|---|---|---|
| WO | WO/2003/096025 A1 | * | 11/2003 |
| WO | WO2007098417 | * | 8/2007 |

OTHER PUBLICATIONS

Oyama et al., Molecular Brain Research, 29:92-98, (Year: 1995).*
Dong et al. PLOS One, 8(4):e61991, published Apr. 2013 (Year: 2013).*
Lum et al., Am J Physiol Heart Circ Physiol., 285:H1786-89, published Jun. 12, 2003 (Year: 2003).*
Huang et al., J Neuroscience, 36(30):7996-8011, Jul. 2016 (Year: 2016).*
Hampe et al., J Cell Science, 113:4475-4485, published Nov. 2000 (Year: 2000).*
Xu et al. Molecular and Cellular Neuroscience, 36:313-331, published online Jul. 24, 2007 (Year: 2007).*
Yajima et al., Biochemical and Biophysical Research Communications, 456:482-488, 2015 (Year: 2015).*
BrightFocus Foundation, "Targeted Discovery of LR11/SorLA-Based AD Therapeutics", published 2010. Retrieved from < https://www.brightfocus.org/taxonomy/term/101?page=10> Retrieved on: Feb. 6, 2023. (Year: 2010).*
May et al., Toxicon, 69:143-151, (Year: 2013).*
International Search Report and Written Opinion dated Aug. 31, 2018, for corresponding International Application No. PCT/US2017/66881, International Filing Date Dec. 15, 2017, consisting of 20-pages.
Hayato Fukuda, et al., Identification of a Potent and Selective GPR4 Antagonist as a Drug Lead for the Treatment of Myocardial Infarction, ACS Medical Chemistry Letters, Feb. 24, 2016 vol. 7, No. 5, pp. 493-497.
Anne Urfer-Buchwalder, et al., Identification of a Nuclear Respiratory Factor 1 Recognition Motif in the Apolipoprotein E Variant APOE4 linked to Alzheimer's Disease, Scientific Reports, Jan. 17, 2017, vol. 7, No. 40668, pp. 1-8.
Shubhabrata Mukherjee, et al., Systems Biology Approach to Late-Onset Alzheimer's Disease Genome-Wide Association Study Identifies Novel Candidate Genes Validated Using Brain Expressions Data and Caenorhabditis Elegans Experiments, Alzheimner's & Dementia, Oct. 2017, Epub: Feb. 24, 2017, vol. 13, No. 10, pp. 1133-1142.

* cited by examiner

*Primary Examiner* — Kimberly Ballard
*Assistant Examiner* — Stacey N MacFarlane
(74) *Attorney, Agent, or Firm* — Gearhart Law LLC

(57) ABSTRACT

The present invention provides compositions and methods using APOE4 motif-mediated genes and expression products thereof for diagnosis, treatment and prevention of Alzheimer's disease and mild cognitive impairment. The present invention also relates to a method of identifying therapeutic agents to treat and diagnose Alzheimer's disease or mild cognitive impairment based on APOE4 motif-mediated genes.

11 Claims, 9 Drawing Sheets
Specification includes a Sequence Listing.

```
APOE_HUMAN       RLGADMEDVCGRLVQYRGEVQAMLGQSTEELRVRLASHLRKLRKLRKRLLRDADDLQKRLAVY 180
APOE_CHIMPANZEE  RLGADMEDVRGRLVQYRGEVQAMLGQSTEELRARLASHLRKLRKLRKRLLRDADDLQKRLAVY 180
APOE_MACAQUE     RLGADMEDVRSRLVQYRSEVQAMLGQSTEELRARLASHLRKLRKLRKRLLRDADDLQKR---- 107
APOE_GORILLA     RLGADMEDVRGRLAQYRGEVQAMLGQSTEELRARLASHLRKLRKLRKRLLRDADDLQKRLAVY 180
APOE_ORANGUTAN   RLGADMEDVRGRLVQYRGEVQAMLGQSTEELRARLASHLRKLRKLRKRLLRDADDLQKRLAVY 180
APOE_DOG         RLRADMEDVRNRLTQYRGELQAMLGQSSEELRARFASHMRKLRKRVLRDAEDLQRRLAVY     168
APOE_PIG         RVGADMEDVRNRLVLYRSEVHNMLGQTTEELRSRLASHLRNVRKRLVRDTEDLQKRLAVY     179
APOE_MOUSE       RLGADMEDLRNRLGQYRNEVHTMLGQSTEEIRARLSTHLRKMRKRLMRDAEDLQKRLAVY     172
APOE_RAT         RLGADMEDLRNRLGQYRNEVNTMLGQSTEELRSRLSTHLRKMRKRLMRDADDLQKRLAVY     172
APOE_RABBIT      ALEADMEDVCNRLAQYRGEAQAMLGQSTEELARAFSSHLRKLRKLRKRLLRDAEDLQKRMAVY 173
APOE_BOVIN       RLGSDMEDLRNRLAQYRSEVQAMLGQSTEELRARMASHLRKLPKRLLRKLPKRLLDADDLKKRLAVY 179
```

FIGURE 1

```
                           130                                                    176
APOE_HUMAN ε3    RLGADMEDVCGRLVQYRGEVQAMLGQSTEELRVRLASHLRKLRKLRKRLLRDADDLQKRLAVY
APOE_HUMAN ε4    RLGADMEDVKGRLVQYRGEVQAMLGQSTEELRVRLASHLRKLRKLRKRLLRDADDLQKRLAVY
APOE_MOUSE       RLGADMEDLENRLGQYRNEVHTMLGQSTEEIRARLSTHLRKMRKRLMRDAEDLQKRLAVY
```

```
481
GCGGACATGGAGGACGTG[T]GCGGCCGCCTGGTGCAGTACCGCGGCGAGGTGCAGGCCATG
    124 A--D--M--E--D--V--[C]--G--R--L--V--Q--Y--R--G--E--V--Q--
A--M-
```

Cys→Arg

```
541
CTCGGCCAGAGCACCGAGGAGCTGCGGGTGCGCCTCGCCTCCCACCTGCGCAAGCTGCGT
    144 L--G--Q--S--T--E--E--L--R--V--R--L--A--S--H--L--R--K--
L--R-
```

Rs7412
C→T

```
601
AAGCGGCTCCTCCGCGATGCCGATGACCTGCAGAAG[CGC]CTGGCAGTGTACCAGGCCGGG
    164 K--R--L--L--R--D--A--D--D--L--Q--K--[R]--L--A--V--Y--Q--
A--G-
```

Arg→Cys

*The allelic nucleotides are in bold inside the box delineating the variable codons. The resulting amino acid changes are in bold and boxed.*

Comparison of the DNA sequence around the SNPs determining the APOE ε alleles

Rs429358
GGCTGGGCGCGGACATG[GAGGACGTGcGCGGCCGCCTGG]TGCAGTACCGCGGCGAGG

Rs7412
GGCTCCTCCGCGATGCC[GATGACCTGCAGAAGcGCCTGG]CAGTGTACCAGGCCGGGG

Val254Glu protective mutation

T→A

```
730
CGC.GAC.CGC.CTG.GAC.GAG.GTG.AAG.GAG.CAG.G[T]G.GCG.GAG.GTG.CGC.GC
C.AAG.CTG.GAG
    244 -R---D---R---L---D---E---V---K---E---Q---[V]---A---E---V---R---A---K---L---E-
```

V→E

Sequence comparison between rs429358 (APOE4) and rs199768005 (Val254Glu)

rs429358
GGCTGGGCGCGGACA[TGGAGGACGTGcGCGGCCGCCTGG]TGCAGTACCGCGG CGAGG rs199768005
AGGTGAAGGAGCAGG[tGGCGGAGGTGCGCGCCAAGCTGG]AGGAGCAGGCCCAGCAGA

*Rs429358 and rs7412 and rs199768005 are indicated in lowercase. Common nucleotides are in bold.*

FIGURE 5

```
APOE4 region
GGGCGCGGACATGGAGGA CGTGC GCGGC CGCCTGG TGCAGTACCGCGGCGAGGT
Rs7412 region
CCTCCGCGATGCCGATGA CCTGC AGAAG CGCCTGG CAGTGTACCAGGCCGGGGC
IRF5(3)
GGAGTAGGGCGGGGTCCG CGTCC AGCTG CGCCTGG AAAGCGAGCTCGGGGGGT
IRF5(5)
GGAGTAGGGCGGGGTCCG CGTCC AGCTG CGCCTGG AGACCGAGCTTCGGTG
GGT
C9orf172-1
CGCGGGTCCCGCCCCCCA CGTGC GCTGC CGCCTGG ACATCAAGCCAGACGACGC
19q12
ATTGCCTGAATAAGACAG CCTCC AAAGG CGCCTGG AGGCCGAGGACTCTTAGAA
TRPM4
TGTGCGCGCCGAGGTACC CCTCC GGGGG CGCCTGG GACCCTCACCCAGGCC
AGG
CAPN10Ins   CCCTCCCACAAGCCCACC CTCCT CCCAgctcctgggacagaatcatcaccctcc
```

*IRF5, Interferon Regulatory Factor 5; TRPM4, Transient Receptor Potential Cation Channel, Subfamily M, Member 4, CAPN10, Calpain 10. Rs429358 and rs7412 and the Calpain 10 insert (Ins) are in lowercase. Nucleotides occurring in at least four of the sequences at a given position shown in bold.*

Sequence repeats within Exon 4 of Apolipoprotein E

```
GGCGCTGATGGACGAGACCATGAAGGAGTTGAAGGCCTACAAATCGGAACTGGAGGAACAAC
TGACCCCGGTGGCGGAGGAGACGCGGGCACGGCTGTCCAAGGAGC TGCAGGCGGCGCAGGCC
CGGCTGG GCGCGGACA TGGAGGACGTG C GCGGCCGCCTGG TGCAGTACCGCGGCGAGGTGC
AGGCCATGCTCGGCCAGAGCA CCGAGGAGCTGCGGGTGCGCCTCG CCTCCCACCTGCGCAAG
CTGCGTAAGCGGCTCCTCCGCGATG CCGATGACCTGCAGAAG C GCCTGG CAGTGTACCAGG
CCGGGGCCCGCGAGGGCGCCGAGCGCGGCC TCAGCGCCATCCGCGAGCGCCTGG GGCCCCTG
GTGGAACAGGGCCGCGTGCGGGCCGCCACTGTGGGCTCCCTGGCCGGCCAGCCGCTACAGGA
GCGGGCCCAGGCCTGGGGCGAGCGGCTGCGCGCGCGGA TGGAGGAGATGGGCAGCCGGACCC
GCGACCGCCTGG ACGAGG
TGAAGGAGCAGG TGGCGGAGGTGCGCGCCAAGCTGG AGGAGCAGGCCCAGCAGATACGCCTG
CAGGCCGAGGCCTTCCAGGCCCGCCTCAAGAGCTGGT TCGAGCC CCTGG TGGAAGACATGCA
GCGCAG TGGGCCGGGCTGG TGGAGAAGGTGCAGGCTGCCGTGGGCACCAGCGCCGCCCCTGT
GCCCAGCGACAATCACTGAACGCCGAAGCCTGCAGCCATGCGACCCCACGCCACCCCGTGCC
TCCTGCCTCCGCGCAGCCTGCAGCGGGAGACCCTGTCCCCGCCCCAG CCGTCCTCCTGG GGT
GGACCCTAGTTTAATAAAGATTCACCAAGTTTCACGCA
```

*Rs429358 and rs7412 are indicated by a double box. Elements of high similarity with APOE4 motif are indicated by boxes. Nucleotides common to APOE4 region are in bold.*

FIGURE 6

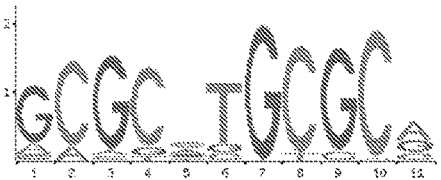

De novo NRF1 binding motif overlapping APOE4 on the reverse strand

| G | C | G | G | C | C | G | C | G | C | A |
|---|---|---|---|---|---|---|---|---|---|---|
| 1 | 2 | 3 | 4 | 5 | 6 | 7 | 8 | 9 | 10 | 11 |

Position Frequency Matrix for each nucleotide in the recognition motif (Jaspar database) matched to APOE4 and APOE3 overlapping sequences (reverse strand).

| Position | 1 | 2 | 3 | 4 | 5 | 6 | 7 | 8 | 9 | 10 | 11 |
|---|---|---|---|---|---|---|---|---|---|---|---|
| A | 602 | 623 | 196 | 0 | 1514 | 0 | 0 | 0 | 0 | 74 | 2245 |
| C | 375 | 4001 | 189 | 416 | 1862 | 403 | 0 | 4338 | 349 | 4550 | 804 |
| G | 3647 | 0 | 4239 | 468 | 935 | 528 | 4624 | 0 | 4275 | 0 | 1575 |
| T | 0 | 0 | 0 | 140 | 313 | 3693 | 0 | 286 | 0 | 0 | 0 |
| APOE3 | G | C | G | G | C | C | G | C | a | C | A |
| APOE4 | G | C | G | G | C | C | G | C | g | C | A |

*Pertaining nucleotide frequency at each position is in bold. Variant rs429358/C is indicated in small cap.*

FIGURE 7

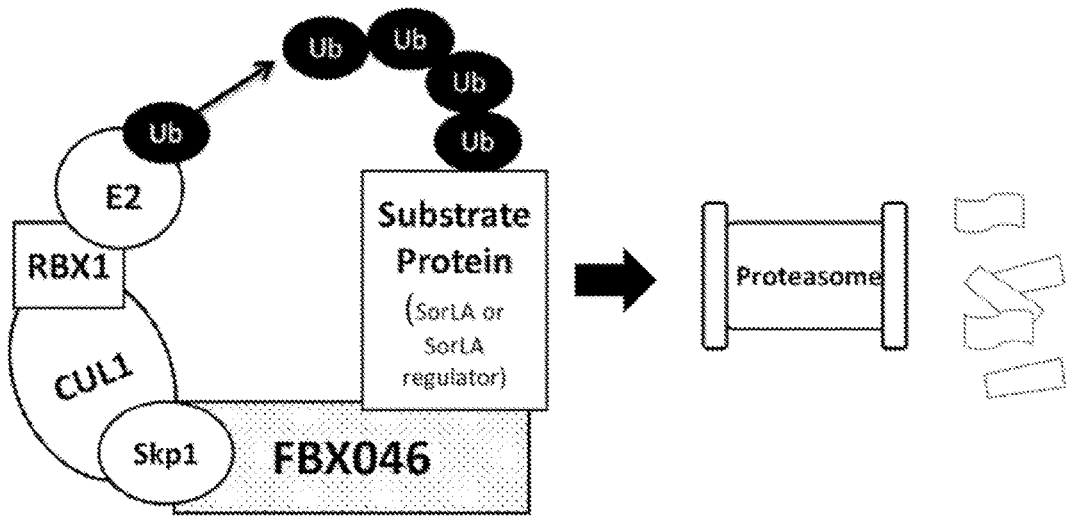

FIGURE 8A

USE OF APOE4 MOTIF-MEDIATED GENES FOR DIAGNOSIS AND TREATMENT OF ALZHEIMER'S DISEASE

CROSS-REFERENCE TO RELATED APPLICATIONS

This application claims the priority benefit of U.S. Provisional Application No. 62/435,815, filed Dec. 18, 2016, which is incorporated herein by reference in its entirety.

FIELD OF THE INVENTION

The present invention relates to a method of diagnosing, preventing and treating Alzheimer's disease or mild cognitive impairment. Methods of the invention are based at least in part on measuring or modulating one or more genes, or their expression products, from a set of genes identified by the present inventors as being connected to Alzheimer's disease (referred to herein as the "APOE4 motif-mediated genes"). The present invention also relates to a method of using the inhibition of APOE4 motif-mediated gene expression to treat and diagnose Alzheimer's disease or a mild cognitive impairment.

BACKGROUND OF THE INVENTION

Alzheimer's disease (AD) affects tens of millions of people worldwide and its prevalence continues to rise. Currently, however, there are no reliable and effective methods for diagnosis, treatment or prevention of AD. It is believed that AD is caused by a combination of environment, lifestyle, medical condition and genetic factors. AD often goes unrecognized in its early stages where treatments might be most effective. Current Food and Drug Administration (FDA) approved Alzheimer's drugs have significant side effects and only modest effects on improving the patient's daily functioning but do not slow down the disease process or treat the underlying pathology.

The biochemical basis of AD is not fully understood. Most of AD research has focused on the accumulation of amyloid plaques—whose major components are 39- to 43-amino acid β-amyloid peptides derived by proteolytic cleavages of the amyloid precursor protein (APP)- and and neurofibrillary tangles of hyperphosphorylated microtubule associated protein Tau (MAPT). Other hallmarks of AD include the dysregulation of cyclin-dependent kinase 5 (CDK5)[i] which participates in the abnormal hyperphosphorylation of Tau and the presence of neuroinflammation from early to late stages of AD. Markers of DNA damage, particularly oxidative DNA damage, have been found in brain regions, peripheral tissues, and biological fluids of AD patients. Research has also suggested AD involves dysfunction in neuronal cell cycle reentry[ii]. An increased occurrence of chromosomal anomalies, micronuclei, binucleation and aneuploidy has been noted in AD patients' neurons, lymphocytes[iii] and somatic cells[iv]. Autophagy dysregulation[v], Golgi fragmentation and atrophy[vi] are also typically observed. Downregulation of cell-surface α-Amino-3-hydroxy-5-methyl-4-isoxazolepropionic acid receptors (AMPAR) and selective loss of GluR2/R3 AMPAR subunits was observed, even before plaque formation[vii]. Additionally, early endosomes are markedly enlarged in sporadic AD, an anomaly which develops years before the earliest stage of AD[viii].

Unfortunately, it is not clear whether the biochemical events observed are a cause or a result of the development of AD. The conventional research apparently does not relate to the actual mechanism of causation of AD but rather only relates to the consequences of the underlying mechanism that causes AD. If one can gain detailed knowledge of the underlying mechanism for development of AD, it would be possible to accurately diagnose, treat and/or prevent development of AD.

One tantalizing clue towards possible treatments for AD comes from genetic research which, in the early 1990s, revealed that people carrying a specific allele of the apolipoprotein (APOE) gene, namely the APOE4 allele, are at substantially increased risk of developing AD. Apolipoproteins have a major role in transporting cholesterol and triglycerides in the blood and liver. The genetic discovery has triggered substantial investigation into the role apolipoproteins may play in the development of AD. To date there is no generally accepted explanation for the correlation between APOE4 activity, which is predominantly in the blood and liver, and the observed biochemical effects of AD which are identified in the brain, beyond the blood-brain barrier. Here again, this research area has been frustrating and has not yet led to new treatments for AD.

Since current treatment of AD only treats the symptoms and not the underlying cause of AD, there is still a need for a method for treating AD by treating the actual cause of AD.

SUMMARY OF THE INVENTION

Some aspects of the present invention are based on the discovery of a set of genes that are directly responsible for the development of AD. This discovery by the present inventors provides multiple new avenues for diagnosing, preventing and/or treating AD.

One particular aspect of the invention is based on the analysis of the gene structure of the APOE4 variant and the unexpected discovery that the APOE4 variant creates a de novo recognition motif for the neuron-specific transcription factor NRF1. This remarkable finding by the present inventors reveals for the first time that the APOE4 allele is causing transcription effects in brain cells, and unexpectedly modulating (e.g., activating or suppressing) transcription of a wide range of genes, herein referred to as APOE4 motif-mediated genes. These genes are not activated (or suppressed) to the same extent by other alleles of APOE, thereby for the first time providing an explanation for the correlation of APOE4 with AD. As discussed herein, APOE4 motif-mediated gene expression can result in inhibition or activation of a particular gene or the activity of the gene expression product. Accordingly, throughout this disclosure, it should be understood that when the term "inhibit" is used in reference to APOE4 motif-mediated gene expression or the gene expression product thereof, the term "inhibit" can be alternatively be substituted with the term "increase" or "activate." For example, if a particular gene expression (or the activity of the gene expression product thereof) is reduced or suppressed due to the presence of APOE4 allele, then the methods of the invention will be directed to increasing the gene expression (or the activity of the gene expression product thereof). Similarly, if a particular gene expression (or the activity of the gene expression product thereof) is increased due to the presence of APOE4 allele, then the methods of the invention will be directed to inhibiting the gene expression (or the activity of the gene expression product thereof).

The transcription factor which recognizes the APOE4 motif is Nuclear respiratory factor 1 ("NRF1"). Nuclear respiratory factor 1, also known as Nrf1, Nrf-1, NRF1 and NRF-1, has been associated with the regulation of neurite outgrowth. NRF1 has also been shown to encode a protein that homodimerizes and functions as a transcription factor which activates the expression of some key metabolic genes. An analysis of target genes in the vicinity of APOE4 which may be activated by NRF1 identified FBXO46 as an AD causing gene. FBXO46 interferes with the function of the physiological amyloidogenic pathway, leading to widespread protein sorting dysfunction, cell cycle re-entry and neuronal death and thereby is believed to cause AD. In some embodiments, methods of the invention provide inhibiting aberrant activity of FBXO46, and/or inhibiting the function of this NRF1 recognition site created by the APOE4 motif to stabilize or improve the cognitive ability of subjects with AD.

One particular aspect of the invention provides a method of modulating the APOE4 motif-mediated (i.e., regulated) expression of a gene or the activity of gene product thereof. In some embodiments, modulation of the APOE4 motif regulated gene expression is achieved by contacting a cell that is capable of or is expressing a gene mediated by the APOE4 motif with a molecule. As used herein unless the context requires otherwise, the terms "molecule" and "compound" are used interchangeably herein and refers to any molecule known to one skilled in the art, such as, but not limited to, drugs, oligonucleotides (including short interfering RNAs, aptamers, etc.), peptides (including aptamers, antibodies and fragments thereof), as well as derivatives or modified forms thereof. In some embodiments, the cell is a neuronal cell, a neuronal progenitor cell or a differentiated neuron. In other embodiments, the modulation of the activity of APOE4 motif-mediated gene expression product is achieved by contacting said gene expression product with a molecule that is capable of selectively modulating said gene expression product.

Yet in other embodiments, the gene that is expressed by the APOE4 motif is located on human chromosome 19 within about 2 Mb of rs429358. In other embodiments, the APOE4 motif-mediated gene is selected from the group consisting of PSG1, XRCC1, PINLYP, IRGQ, ZNF576, SRRM5, ZNF428, PLAUR, SMG9, ZNF224, ZNF285, ZNF180, PVR, BCL3, CBLC, BCAM, PVRL2/NECTIN2, CLPTM1, RELB, CLASRP, GEMIN7, MARK4, PPP1R37, NKPD1, TRAPPC6A, BLOC1S3, EXOC3L2, CKM, KLC3, ERCC2, PPP1R13L, ERCC1, FOSB/deltaFOSB, RTN2, VASP, OPA3, GPR4, EML2, GIPR, SNRPD2, QPCTL, FBXO46, SIX5, SYMPK, FOXA3, MYPOP, NOVA2, CCDC61, HIF3A, PPP5C, PNMA8A/PNMAL1, PNMA8B/PNMAL2, DACT3, STRN4, FKRP and a combination thereof. Still in other embodiments, the APOE4 motif-mediated gene comprises FBXO46, SNRPD2, ZNF285, ZNF180, PVR, ERCC2, QPCTL, SYMPK, MYPOP, CCDC61, XRCC1, ZNF576, ZNF428, SMG9, PPP5C, PNMA8A/PNMAL1, PNMA8B/PNMAL2, DACT3, STRN4, FKRP, RTN2, IRGQ, SRRM5, FOXA3, FOSB/deltaFOSB, SIX5, GPR4 or a combination thereof. In a further embodiment, the APOE4 motif-mediated gene comprises FBXO46, PPP5C, FKRP, SYMPK, FOSB/deltaFOSB, FOXA3, GPR4, PSG1, PPP1R13L, EXOC3L2, SIX5, PLAUR, KLC3 or a combination thereof.

In one particular embodiment, the APOE4 motif-mediated expression is modulated using a molecule or a compound that modulates APOE4 motif-mediated gene expression. As used herein, the terms "APOE4 motif-mediated gene," "gene mediated by APOE4 motif" and "APOE4 motif" are used interchangeably herein and refer to gene(s) located on human chromosome 19 within about 5 Mb, typically within about 4 Mb, often within about 3 Mb, and most often within about 2 Mb of rs429358. In one particular embodiment, the APOE4 motif-mediated gene is selected from the group consisting of PSG1, XRCC1, PINLYP, IRGQ, ZNF576, SRRM5, ZNF428, PLAUR, SMG9, ZNF224, ZNF285, ZNF180, PVR, BCL3, CBLC, BCAM, PVRL2/NECTIN2, CLPTM1, RELB, CLASRP, GEMIN7, MARK4, PPP1R37, NKPD1, TRAPPC6A, BLOC1S3, EXOC3L2, CKM, KLC3, ERCC2, PPP1R13L, ERCC1, FOSB/deltaFOSB, RTN2, VASP, OPA3, GPR4, EML2, GIPR, SNRPD2, QPCTL, FBXO46, SIX5, SYMPK, FOXA3, MYPOP, NOVA2, CCDC61, HIF3A, PPP5C, PNMA8A/PNMAL1, PNMA8B/PNMAL2, DACT3, STRN4, FKRP and a combination thereof. Still in another embodiment, the APOE4 motif-mediated gene comprises FBXO46, SNRPD2, ZNF285, ZNF180, PVR, ERCC2, QPCTL, SYMPK, MYPOP, CCDC61, XRCC1, ZNF576, ZNF428, SMG9, PPP5C, PNMA8A/PNMAL1, PNMA8B/PNMAL2, DACT3, STRN4, FKRP, RTN2, IRGQ, SRRM5, FOXA3, FOSB/deltaFOSB, SIX5, GPR4 or a combination thereof. In a further embodiment, the APOE4 motif-mediated gene comprises FBXO46, PPP5C, FKRP, SYMPK, FOSB/deltaFOSB, FOXA3, GPR4, PSG1, PPP1R13L, EXOC3L2, SIX5, PLAUR, KLC3 or a combination thereof. The terms "about" and "approximately", when used to describe a numeric value, are used interchangeably herein and are not intended to limit the scope of the invention unless indicated otherwise. The terms "about" and "approximately" refer to being within an acceptable error range for the particular value as determined by one of ordinary skill in the art, which will depend in part on how the value is measured or determined, i.e., the limitations of the measurement system, i.e., the degree of precision required for a particular purpose. For example, the terms "about" and "approximately" can mean within 1 or more than 1 standard deviation, per the practice in the art. Alternatively, the terms "about" and "approximately" when referring to a numerical value can mean±20%, typically ±10%, often ±5% and more often ±1% of the numerical value. In general, however, where particular values are described in the application and claims, unless otherwise stated, the terms "about" and "approximately" mean within an acceptable error range for the particular value. The term "modulate" when used in reference to APOE4 motif-mediated gene expression includes reducing or increasing transcription and/or translation of the gene. This can include downregulating or complete suppression or upregulating of gene expression as compared to a control (e.g., in the absence of the molecule). Typically, methods of the invention show at least about 25%, typically at least about 50%, and often at least about 75% modulation of APOE4 motif-mediated gene expression or activity of the expression product thereof. In one particular embodiment, methods of the invention inhibits APOE4 motif-mediated gene expression or activity of the expression product thereof.

The molecule used for inhibiting APOE4 motif-mediated expression of a gene includes, but not limited to, a drug, an oligonucleotide, a peptide or a derivative thereof or a combination thereof. In some instances, the oligonucleotide is 11 to 30 nucleotides in length comprising consecutive nucleotide sequences within SEQ ID NO: 1. In some cases, the oligonucleotide is a single-stranded oligonucleotide while in other instances the oligonucleotide is a double-stranded oligonucleotide. The oligonucleotide can also be a phosphorothioate oligonucleotide, a methylphosphonate oligonucleotide, a phosphoamidite oligonucleotide, a peptide nucleic acid oligonucleotide, a locked-nucleic acid-modified oligonucleotide, or combinations thereof.

In some embodiments, the molecule further comprises a pharmaceutically acceptable carrier.

Another aspect of the invention provides a method for identifying a molecule that can inhibit binding of a transcription factor to the APOE4 motif. This method can be used inter alia to identify a lead candidate for a drug development for treatment of AD.

Yet another aspect of the invention provides a method for inhibiting APOE4 motif-mediated expression of a gene in a cell. The method comprises contacting a cell that is expressing a gene mediated by the APOE4 motif with a molecule that is capable of inhibiting expression of said gene. Yet in other embodiments, the molecule comprises a drug, an oligonucleotide, a peptide or a derivative thereof or a combination thereof. In some instances, the oligonucleotide is a small interfering RNA (siRNA). Still in other embodiments, the APOE4 motif-mediated expressed gene is MIR4531, MIR8085, MIR6088, MIR330, MIR642A, MIR642B, MIR769 or MIR320E and the molecule that is used for inhibiting expression is a locked nucleic acid modified oligonucleotide. As used herein, the term "locked nucleic acid" refers to a nucleic acid in which the ribose moiety is modified with an extra bridge connecting the 2'-oxygen and 4'-carbon.

Yet another aspect of the invention provides a method for treating a subject suffering from Alzheimer's disease or mild cognitive impairment. The method includes determining the APOE genotype present in the subject; and (a) if said subject carries the APOE4 allele, administering said subject with a molecule that is capable of inhibiting binding of a transcription factor to the APOE4 motif; or (b) if said subject does not carry the APOE4 allele, administering said subject with a molecule that is different from said molecule of (a). In some embodiments, the method can include a step of determining whether said subject is homozygous or heterozygous for APOE4. As used herein, the term "treating" or "treatment" of a disease includes: (1) preventing the disease, i.e., causing the clinical symptoms of the disease not to develop in a mammal that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The advantages of the present invention include a transformative approach to AD treatment, targeted therapies addressing APOE4 motif-mediated dysfunction that delays AD onset, prevent its progression or reverse its symptoms, and provide disease-modifying therapies, i.e., treating the actual cause of AD rather than treating mere symptoms of AD.

BRIEF DESCRIPTION OF THE DRAWINGS

FIG. 1 illustrates a protein sequence alignment of the APOE4 region from 11 mammalian species.

FIG. 2 is comparison of the mouse APOE and human APOE4 with respect to the ε allele residues.

FIG. 5 is analysis the DNA sequences in the proximity of the APOE ε alleles. The APOE4 motif is defined as the sequence "TGGAGGACGTGCGCGGCCGCCTGG". The nucleotide change present in rs429358 is highlighted in bold and underlined.

FIG. 6 demonstrates the genomic occurrences of the APOE4 motif.

FIG. 7 is a schematic illustration showing creation of a de novo NRF1 binding site by APOE4.

FIGS. 8a-c show FBXO46 mechanism of action and the effect of FBXO46 misexpression on the amyloidogenic pathway. FIG. 8a, Legend: The cullin subunit CUL1 functions as a molecular scaffold that interacts at the amino terminus with the adaptor subunit SKP1 (S-phase kinase-associated protein 1) and at the carboxyl terminus with RING-finger protein RBX1 and a specific ubiquitin-conjugating enzyme E2. F-box protein FBXO46 is linked to the core complex through interaction between Skp1 and the F-box domain. Ubiquitin is transferred from E2 onto the substrate recruited by FBXO46. After poly-ubiquitination, the substrate is recognized and degraded by the proteasome or alternatively the lysosome. The specific target substrate for FBXO46 is either SorLA or a protein affecting SorLA gene transcription and/or protein stability. FIG. 8(c) Effect of FBXO46 expression on amyloidogenic pathway. Mutation effect: APOE4 linked expression of FBXO46 reduces SorLA levels; Affected step: APP-BACE1 processing occurs prematurely; End result: Fe65 remains bound to APP, no BACE1 recycling (endosome enlargement), no retromer binding.

DETAILED DESCRIPTION OF THE INVENTION

Figure 3:
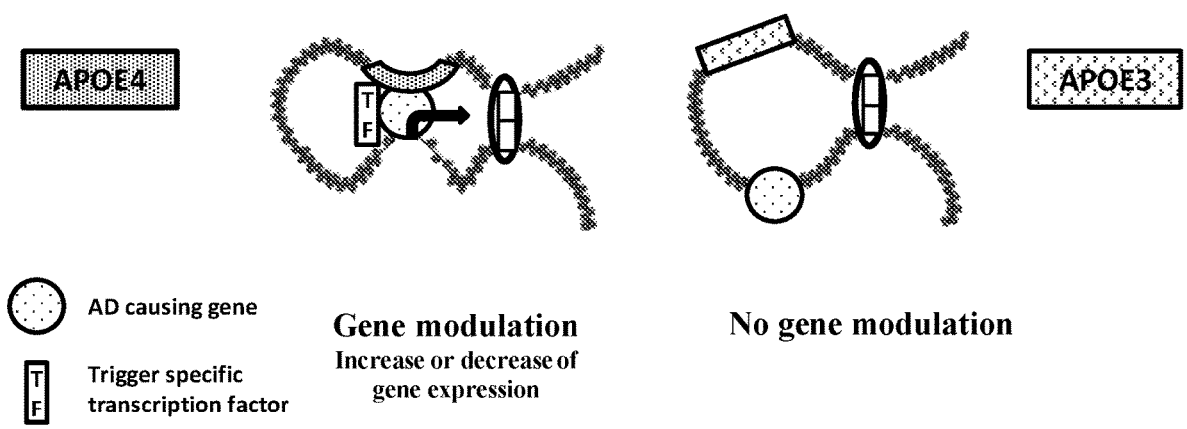
FIG. 3 illustrates the mechanism of activation of the AD causing gene by APOE4 and a trigger-specific transcription factor.

Apolipoprotein E ("APOE") is a major cholesterol carrier that regulates lipid transport from one tissue or cell type to another. In the brain, APOE is mainly produced by astrocytes, and transports cholesterol to neurons via APOE receptors. It is a polymorphic protein arising from different alleles—designated ε 2, 3 and 4—at a single gene locus. An "allele" is a variant or alternative form of a gene that exists in a population. An individual normally inherits two such alleles for each gene at conception. APOE ε variants frequencies in the general population are shown (Table 1). The three major isoforms, APOE2, APOE3, and APOE4, differ from one another by a Cysteine/Arginine substitution at 2 positions, rs429358 (T/C polymorphism at position 19:44908684 on chromosome 19 in the Genome Reference Consortium Human Build 38 patch release 2/GRCh38.p2) and rs7412 (C/T polymorphism at position 19:44908822 on chromosome 19 in GRCh38.p2), affecting residues 130 and 176 in the synthesized protein containing the signal-peptide and residues 112 and 158 in the mature protein. APOE allele ε4 (APOE4 variant, short form E4) harbors a C at position 19:44908684 and position 19:44908822. APOE allele ε2 (APOE2 variant, short form E2) harbors a T at both positions. APOE allele ε3 (APOE3 variant, short form E3) harbors a T at position 19:44908684 and a C at position 19:44908822 (Table 2). In the following paragraphs "APOE2/E3/E4" will refer either to the gene or the protein variants depending on the context. "APOE2/E3/E4" has the meaning that either APOE2, or APOE3 or APOE4 is present. APOE3 is the normal isoform for all known functions. APOE2 is associated with the genetic disorder type III hyperlipo-proteinemia and atherosclerosis[ix].

TABLE 1

APOE ε variants frequencies in the general population

| Genotype | ε2/ε2 | ε2/ε3 | ε2/ε4 | ε3/ε3 | ε3/ε4 | ε4/ε4 |
|---|---|---|---|---|---|---|
| Frequency in global population (%) | 1 | 12 | 2 | 60 | 22 | 2 |

TABLE 2

APOE2, APOE3, and APOE4

| | rs429358 | | | rs7412 | | |
|---|---|---|---|---|---|---|
| Variant | Nucleotide | AA 130 | MAF | Nucleotide | AA 176 | MAF |
| ε2 | T | Cys | 0.851 | T | Cys | 0.074 |
| ε3 | T | Cys | 0.851 | C | Arg | 0.926 |
| ε4 | C | Arg | 0.149 | C | Arg | 0.926 |

Linkage studies and genome wide associations by the present inventors have revealed that the Apolipoprotein E variant APOE4 as the largest known genetic risk factor for AD. In addition, meta-analysis of clinical and autopsy-based studies demonstrated that the risk of developing AD increases with each copy of the E4 variant compared with the E3/E3 genotype: Odds ratios (OR) are 2.6 (E2/E4) and 3.2 (E3/E4) with one copy of the E4 allele, OR increases to 14.9 with two copies of the allele (E4/E4). On the other hand, the E2 allele of APOE is protective against AD, with an OR=0.6 for E2/E2 individuals. APOE4 is associated with an earlier age of onset with age 68 as mean age of clinical onset for APOE4 homozygotes versus 84 years of mean age of clinical onset for subjects not carrying the APOE4 allele[x]. Clinical and epidemiological data have indicated that, depending on the population and the study, between 40 to 80% of AD patients are APOE4 carriers[xi] with penetrance of APOE4 estimated to be at 60-80%. These data show that the magnitude of the effect of APOE on AD is more similar to the one observed for major genes in Mendelian diseases such as BRCA1 in breast cancer than to low-risk common alleles identified by recent GWASs in complex diseases[xii].

The most commonly accepted prodromal AD stage is mild cognitive impairment (MCI), which is characterized by clinically-relevant cognitive dysfunction in the absence of significant interference with daily functioning. The relative risk of progression from normal cognition to mild impairment was doubled for individuals with one or more APOE4 alleles[xiii]. In addition, E4/E4 homozygote status substantially accelerates progression from MCI to dementia, and accelerate dementia occurrence by more than 3 years in people with MCI[xiv].

Genome wide association studies have shown that the APOE region is also significantly associated with nonpathological cognitive ageing[xv].

Variants ε2, ε3, and ε4 are imbedded in a CpG island (CGI) overlapping the end of Intron 3 and Exon 4 of the APOE gene that is highly methylated in the human brain. This APOE CGI can function both as a transcriptional enhancer or silencer in a luciferase-based reporter system depending on cell type and promoter construct[xvi,xvii].

Amino acid changes in proteins almost always lead to reduced function, and are prime suspects for disease causation. Since a direct causative effect could not be assigned to APOE4 protein function in AD, whole exome sequencing of thousands of AD patient DNA samples were subsequently undertaken. However, these studies failed to identify non-synonymous mutations associated with the disease (other than APOE4). Several genomic regions were identified in genome wide association studies as risk factors for late-onset disease (e.g., CLU, PICALM, CR1, BIN1, MS4A, CD2AP, CD33, EPHA1, and ABCA7)[xviii]. However, no single functional risk variant were identified from over 400 genetic association studies performed. In these studies, only a small fraction of patients had a given single nucleotide polymorphism (SNP). Moreover, the vast majority of SNPs identified were located in introns. APOE4 is the sole mutation consistently associated with AD.

Approximately half of the cases of early-onset Alzheimer's (i.e., diagnosed before the age of 65) are Familial Alzheimer's Disease (FAD), and are inherited in an autosomal dominant fashion. FAD is caused by a mutation in one of at least 3 genes: APP mutants, PSEN1 mutants and PSEN2 mutants. Amyloid Precursor Protein (APP) mutations have been identified in 121 families. The most common missense mutations replace $Val^{717}$ residue by Ile (London mutation), Phe, or Gly residues, $Glu^{693}$ by Gln residue (Dutch mutation) or Gly residue (Arctic mutation), or $Lys^{670}$ and $Met^{671}$ by Asn and Leu residues (double mutant known as the Swedish mutation, numbering in $APP_{770}$ isoform). 219 Presenilin 1 (PSEN1) mutations have been identified in 480 families, with impaired γ-secretase cleavage, increased oxidative stress for some mutants and increased neuron sensitivity to DNA damage-induced death[xix]. 13 Presenilin 2 (PSEN2) mutations have been identified in 34 families, with impaired γ-secretase cleavage and increased oxidative stress for some mutants[xx].

Non-amyloidogenic processing of APP occurs mainly at the cell surface, where α-secretases are present. It is the main type of APP cleavage under physiological conditions[xxi]. Proteolytic cleavage by alpha-secretase leads to the generation of soluble APP peptides (SAPPα), and the retention of a corresponding membrane-anchored C-terminal fragment, C83. Subsequent processing of C83 by presenilin/nicastrin-mediated γ-secretase yields p3 peptides and a C-terminal intracellular soluble domain AICD. After γ-secretase processing soluble AICD is released in the cytoplasm where it is degraded, although a fraction of it is redistributed to the nucleus where it could have important signaling functions[xxii]. Amyloidogenic processing is part of the normal APP processing as well, but involves transit through the endocytic organelles, where APP encounters β-secretase (BACE1)[xxiii]. APP proteolytic cleavage by BACE1 leads to the generation of soluble APP peptides (SAPPβ), and the retention of a corresponding membrane-anchored C-terminal fragment, C99. Processing of C99 by γ-secretase releases AICD and amyloid-beta fragments (Aβ40-42). The Aβ40/Aβ42 ratio is influenced by the intracellular site of production. Aβ40 is generated predominantly in the trans-Golgi network (TGN), relying on an endocytosed pool of APP recycled from early endosomes to the TGN[xxiv]. An interruption of the bidirectional trafficking of APP between the TGN and endosomes, particularly retromer-mediated retrieval of APP from early endosomes to the TGN, results in the accumulation of endocytosed APP in early endosomes with reduced APP processing. BACE1 undergoes recycling between the endosome, TGN, or the plasma membrane, from where it is endocytosed. The cytosolic domain of BACE1 contains an acid cluster-dileucine motif (ACDL) that binds Golgi-localized γ-ear-containing ARF-binding (GGA) proteins and influences its subcellular distribution. Phosphorylation of $Ser^{498}$ by casein kinase 1 facilitates BACE1 recognition by GGA1 for retrieval to the endosome. Ubiquitination of the BACE1 C-terminal Lys$^{501}$ signals GGA3 to export BACE1 to the lysosome for degradation. The retromer mediates the retrograde transport of BACE1 from the endosome to TGN. Under basal conditions, the majority of APP and BACE1 containing dendritic vesicles are largely segregated after synthesis via the secretory pathway. While BACE1 is sorted into acidic recycling endosomes, APP is conveyed in Golgi-derived vesicles. However, upon trigger induction of the amyloidogenic pathway APP is routed into BACE1-positive recycling endosomes via a clathrin-dependent mechanism[xxv]. Alternatively, BACE1 may cluster in lipid rafts at the plasma membrane and undergo endocytosis together with APP.

The cytoplasmic domain of APP contains the highly conserved Y$^{682}$ENPTY$^{687}$ motif (residue numbering of neuronal APP spliceform APP$_{695}$) where several adaptor proteins bind through their phosphotyrosine-binding (PTB) domains, most notably Fe65 (Amyloid beta A4 precursor protein-binding family B member 1, APBB1)[xxvi]. Fe65 is a 90-kDa adaptor protein expressed in neurons in several regions of the mammalian nervous system[xxvii]. Fe65 possesses three putative protein-protein interaction domains: one WW (tryptophan-rich, proline-proline-leucine-proline-sequence binding) domain and two PTB domains. The PTB1 domain binds among others histone acetyltransferase Tip60 (KAT5)[xxviii] and the transcription factor LSF/CP2/LBP1 (TFCP2), which is a genetic determinant of risk of AD[xxix]. TFCP2 drives the expression of thymidylate synthase that is essential for DNA replication and cell survival. Moreover, Fe65 also interacts with proteins involved in actin cytoskeleton remodeling through its WW domain, notably Vasodilator-stimulated phosphoprotein VASP. VASP has been shown to modulate spine and synapse formation, maturation, and spine head enlargement[xxx].

Low density lipoprotein-related protein-1 (LRP1) is a receptor localized mainly in hepatocytes, fibroblasts, and neurons. It is composed of an extracellular ligand-binding subunit (515-kDa α-chain) linked to a shorter transmembrane subunit (85-kDa β-chain). It is implicated in diverse biological processes both as an endocytic receptor and as a signaling molecule. Moreover, LRP1 expression is critical for the survival of primary neurons under stress conditions[xxxi]. Under physiological conditions LRP1 undergoes ectodomain shedding, mediated by metalloproteinases, to release a soluble form of LRP1 (sLRP1) that can bind to ligands[xxxii]. LRP1 and its ligands, notably APOE, are genetically associated with AD and are found in senile plaques of AD patients[xxxiii]. Along with LRP1, APP is transported from the early secretory compartments to the cell surface and subsequently internalized into the endosomal compartment. It has been shown that LRP1 modulates multiple steps in APP processing and trafficking, including the turnover of both full-length and C-terminal fragments of APP, secretion of APPs, internalization of cell surface APP, and the generation and release of Aβ peptide[xxxiv]. APP is not known to directly bind to LRP1 but rather through an indirect interaction with the PTB1 domain of Fe65[xxxv].

Phosphorylation of APP at Thr$^{668}$ by proline-directed protein kinases such as CDK5, GSK-3β, CDK1 and c-Jun N-terminal protein kinase (JNK)[xxxvi] can be observed in neurons in normal conditions. Threonine$^{668}$ phosphorylation by JNK is required for γ-mediated cleavage of the C-terminal fragment of APP produced by β-secretase[xxxvii]. Thr$^{668}$ is located within the motif $^{667}$VTPEER$^{672}$, which forms a type I β-turn and amino-terminal helix-capping box structure that stabilizes its carboxyl-terminal helix structure. Phosphorylation of Thr$^{668}$ induces a conformational change in APP cytoplasmic region, affecting its interaction with Fe65[xxxviii]. The production of Aβ is significantly reduced when phosphorylation of Thr$^{668}$ is either abolished by mutation or inhibited by Thr$^{668}$ kinase inhibitors. Thr$^{668}$ phosphorylation may also facilitate the BACE1 cleavage of APP[xxxix].

Proteins involved in trafficking between endosomal compartments and the TGN, namely the retromer complex (Vps35, Vps26) and its putative receptors (SorL1/Sortilin-Related Receptor, SorLA) have been implicated in the molecular pathology of AD[xl, xli]. Direct binding between APP and the retromer complex has not yet been found, suggesting the existence of a sorting receptor that bridges APP to the retromer. To mediate trafficking of APP to TGN, the retromer binds to the sorting motif of neuronal sorting receptor SorLA, bound itself to cytoplasmic domain of APP[xlii]. Reduced retromer activity can mimic the effects of familial AD Presenilin mutations on APP processing[xliii].

Several studies have shown that SorLA is protective against AD. Reduced levels of SorLA in cortex and hippocampus have been noted in autopsy material from AD patients. Expression of SorLA, on the other hand, is normal in cerebellum (a tissue that is not affected by AD pathology). Western blot and immunohistochemical analysis confirmed a 25% reduction of the SorLA protein in AD frontal cortex[xliv]. Decreased levels of the shed SorLA ectodomain is observed in the cerebrospinal fluid of AD patients[xlv]. Expression of SorLA, however, is normal in individuals suffering from FAD and in PS1/APP transgenic mice[xlvi]. Neuronal SorLA expression is reduced in subjects showing mild cognitive impairment[xlvii]. Several SorLA variants associated with AD have been reported to result in reduced SorLA protein levels[xlviii].

APP interacts with SorLA both through its carbohydrate linked, extracellular domain and its cytoplasmic tail[xlix]. Studies have shown that secretases are allosteric enzymes that require cooperativity by APP oligomerization for efficient processing and that SorLA prevents APP oligomerization, causing secretases to switch to a less efficient non-allosteric mode of action[l]. SorLA also interacts with BACE, and might therefore directly affect BACE-APP complex formation[li]. ROCK2 kinase phosphorylation of SorLA at Ser$^{2206}$, a residue close to the GGA-binding site in the cytoplasmic domain, boosts both SorLA ectodomain shedding by metalloproteinases and GGA binding. This phosphorylation event is necessary for proper APP amyloidogenic processing[lii]. The processed SorLA C-tail remains able to bind C99 (β cleaved, C-terminal APP fragment), independently from the GYENPTY motif[102].

The Nuclear Respiratory Factor 1 (NRF1) protein sequence is deposited in UniProtKB as "NRF1_HUMAN" with the accession number Q16656-1. NRF1 is a homodimeric transcription factor which mediates the expression of key metabolic genes and of a range of nuclear genes essential for mitochondrial biogenesis, including subunits of the respiratory chain complexes, and constituents of the mtDNA transcription and replication machinery[liii]. NRF1 regulates both the expression of glutamatergic receptor subunit genes (e.g., NMDA receptor subunits 1 and 2B and AMPA receptor subunit 2) and of the subunits of ion pumps Na+/K+-ATPase, thus playing an important role in the coupling between energy consumption, energy generation, and neuronal activity[liv]. NRF1 has also been associated with the regulation of neurite outgrowth[lv]. Moreover, a panel of neurodegenerative disease-related genes, such as PARK2, PINK1, PARK7, and GPR37, PSENEN, and MAPT have been recognized as NRF1 targets[lvi]. NRF1 has also been found to be a potentially important factor for AD using network topology analysis of microarray data from post-mortem brains[lvii]

Members of the F-box protein family, such as FBXO46, are components of the SCF complex (or SKP1—Cullin—F-box containing complex), a multi-protein E3 ubiquitin ligase catalyzing the ubiquitination of proteins destined for proteasomal degradation. The cullin subunit CUL1 functions as a molecular scaffold that interacts at the amino terminus with the adaptor subunit SKP1 (S-phase kinase-associated protein 1) and at the carboxyl terminus with RING-finger protein RBX1 and a specific ubiquitin-conjugating enzyme (E2). The F-box protein functions as the variable component that binds SKP1 through the F-box domain and the substrate to be ubiquitinated through other motifs localized C-terminally of the F-box motif. Each F-box protein is target specific and recognizes a small subset of substrates hence contributing to the specificity of SCF.

Some F-box proteins also have functions of their own. FBXP38 as an example is a transcriptional co-activator of Krueppel-like factor KLF7.

Reticulons form a large and diverse family of membrane-associated proteins with multiple functions in cells. Reticulons principally localize to the endoplasmic reticulum, and there is evidence that they are involved in shaping the endoplasmic reticulum (ER) membrane, ER-Golgi trafficking, membrane morphogenesis, vesicle formation and fusion and endocytic recycling[lviii]. The mammalian reticulon family of proteins consists of four members (RTN1-RTN4). Although the reticulon genes are expressed in many tissues, RTN4 (Nogo) and RTN2 are preferentially expressed in nervous tissues. RTN4 has been widely demonstrated to be an inhibitor of axonal extension and neurite outgrowth. Mutations in RTN2 cause the axon-degenerative disorder hereditary spastic paraplegia type 12[lix].

He et al[lx] showed that BACE1 co-immunoprecipitates with RTN1, RTN2, RTN3 and RTN4. Reticulons bind to BACE1 transmembrane/C-terminal domain and inhibit its activity. Overexpression of a single RTN reduces the levels of Aβ produced by HEK-293 cells expressing a mutant of APP[lxi] that fosters β-secretase (Swedish mutation). Reduction of β-amyloid accumulation by RTN3 has been observed in transgenic mice expressing APP Swedish and London mutations[lxii]. On the other hand, reticulons are known to accumulate in the dystrophic neurites of Alzheimer's disease neurons. Transgenic mice overexpressing RTN3 develop dystrophic neuritis that are morphologically similar to those observed in AD brains and that correlate with the formation of RTN3 aggregates in susceptible brain regions[lxiii].

Axonal microtubules in neurons are organized such that the plus-end is oriented out from the cell body, while dendrites exhibit a mixed microtubule polarity containing both minus-end-out and plus-end-out microtubules. Intracellular transport of vesicles and organelles along microtubules is powered by kinesin (anterograde) and cytoplasmic dynein (retrograde) molecular motors. Dynein is a large protein complex with six subunits: a large dynein heavy chain, an intermediate and light-intermediate chain, and three dynein light chains. Kinesin-1 is composed of a pair of heavy chains (KHC), which use ATP hydrolysis to power movement on microtubules, and a pair of light chains (KLC), which regulate KHC activity and mediate cargo attachment. APP is able to recruit kinesin-1 to vesicles through binding of its C-terminus to KLC[lxiv] although some evidence suggests that the attachment of APP to kinesin-1 may not be direct, but instead requires proteins of the c-Jun N-terminal kinase (JNK)-interacting proteins (JIP1-1/JIP-2).

Data further suggest that APP is also able to recruit Dynein-1 as a retrograde APP vesicle motor subunit[lxv]. Moreover kinesin-1 is required for proper association of dynein on APP vesicles. Loss of kinesin-1 on cargos leads to reduced dynein on vesicles. Since both anterograde and retrograde motors can simultaneously attach to the same cargo, tight coordination is critical to proper distribution of intracellular materials. Work in animal models suggests that altered axonal transport caused by kinesin-1 dysfunction perturbs levels of both Aβ and phosphorylated Tau in neural tissues. Mouse transcriptomics have identified KLC1 as a modifier of Aβ accumulation. Functional analysis using neuroblastoma cells showed that overexpression of a KLC1 splicing variant increases the production of both Aβ40 and Aβ42[lxvi].

Apolipoprotein E (APOE) is a key constituent of lipoproteins and is crucial for maintaining cholesterol and triglyceride homeostasis. It is expressed by about 75% of the astrocyte population under normal (healthy) conditions with the highest level of expression in the olfactory bulb. It is not expressed by neurons except in response to stress (e.g., excitotoxic injury). A series of hypotheses have been proposed to explain the association of the APOE4 allele with AD[lxvii]: Impairment of the antioxidative defense system, dysregulation of neuronal signaling pathways, disruption of cytoskeletal structure and function, altered phosphorylation of Tau and the formation of neurofibrillary tangles, depletion of cytosolic androgen receptor levels in the brain, potentiation of Aβ-induced lysosomal leakage and apoptosis in neuronal cells, or promotion of endosomal abnormalities linked to Aβ overproduction, or direct transcriptional effect of the expressed APOE protein[lxviii]. Skilled artisans in the field have concluded that these APOE4 effects are mediated by the amino acid change $Cys^{130}$/Arg in the APOE protein.

Variants in APOE were analyzed and surprisingly found that there is no correlation between APOE variants protein structure and AD: APOE4 variant ($Cys^{130}$/Arg) associated with increased risk of AD is benign as assessed by tools predicting deleterious effects of protein variants (e.g., Sift, PolyPhen-2). $Arg^{132}$/Ser next to it is predicted to be more damaging yet it is not associated with increased risk of AD. Furthermore, it is striking that most mammals carry the E4 isoform at position 130 (Arg). A multiple protein sequence alignment of the APOE4 region from apes and several other mammals is provided in FIG. 1.

Many APOE mouse models have been established to study the mechanisms underlying the pathogenic actions of APOE4. These include transgenic mice expressing different APOE isoforms in neurons or astrocytes, mice expressing neurotoxic APOE4 fragments in neurons and human APOE isoforms knock-in mice. However, since mouse Apoe is equivalent to human APOE4 with respect to the ε allele residues (FIG. 2), results obtained with transgenic mice cannot be representative of the true effect of the human APOE4 variant as they replace WT mouse Apoe by a structurally identical isoform. Moreover, differences observed between APOE isoforms show that human APOE4 protein is only detrimental when artificially overexpressed in transgenic neurons. On the other hand, APOE2/3/4 knock-in into $Apoe^{-/-}$ mice display the same rank order of affinities (APOE4>APOE3>>APOE2) to LDLR as in humans. Moreover, the lipoprotein profile of APOE variants in humans is reflected in mice expressing the corresponding APOE genotype. Differences in cholesterol levels in humans carrying the different APOE isoforms are reflected in the corresponding APOE2/3/4 knock-in mice. In the same way, transgenic overexpression of APO4 in astrocytes (under e.g., Glial fibrillary acidic protein/GFAP) in $Apoe^{-/-}$ mice does not lead to senile plaques accumulation, neurodegeneration nor any other AD hallmark. The present inventors realized that even though APOE allelic effects on cholesterol and fat metabolism are faithfully represented in animal models these models do not display AD hallmarks. The present inventors discovered, contrary to skilled artisans in the field, that the effects of APOE4 on AD are not linked to the Cys to Arg mutation at the protein level.

Many genes are expressed in more than one subset of cells or tissues. The activity of transcription factors allows temporal and spatial regulation of these genes. Transcription factors bind to regulatory elements such as enhancers, resulting in stimulation or enhancement, or alternatively repression of gene transcription. Enhancers contain the same regulatory elements that are found at promoter their corresponding promoters. They generally represent a modular arrangement of short sequence motifs, each interacting with a specific cellular transcription factor[lxix], which will be responsible for turning the transcription on or off in a different set of cells, or at different times in development.

The present inventors discovered that the APOE4 variant at the genetic level contains a short sequence motif, the appearance in the nucleotide frequency matrix of the NRF1 consensus sequence into a highly conserved, consensus matching C nucleotide (G on the reverse strand) with 4275 appearances in the frequency matrix (FIG. 7c). It was discovered that surprisingly, the change of the T nucleotide (APOE3) to a C nucleotide (APOE4) creates a de novo NRF1 binding site. APOE4 motif also leads to a statistically significant hit for transcription factor HIF1A::ARNT. A binding motif for this transcription factor can be found in the APOE3 sequence as well, with a similar score (Table 4). HIF1A::ARNT is hypoxia-inducible factor 1 (HIF-1), a heterodimeric transcription factor composed of the alpha subunit HIF1A (Hypoxia-inducible factor 1, alpha), and the beta subunit ARNT (Aryl hydrocarbon receptor nuclear translocator). HIF-1 is the chief regulator of the cellular response to hypoxia, owing to the activating of many genes. The de novo NRF1 binding motif created by APOE4 overlaps the already existing HIFA::ARNT binding motif. Thus, in APOE4 AD patients' response to hypoxia can be impeded due to competitive binding of NRF1 and HIF-1 to the same DNA region.

TABLE 4

JASPAR Analysis of the Region Overlapping rs429358

| Model ID | Model name | Sequence name | Score | Strand | Predicted site |
|---|---|---|---|---|---|
| MA0506.1 | NRF1 | Consensus | 18.058 | forward | GCGCCTGCGCA |
| MA0506.1 | NRF1 | APOE3, Rs429358/T | 3.879 | reverse | GCGGCCGCaCA |
| MA0506.1 | NRF1 | APOE4, Rs429358/C | 11.859 | reverse | GCGGCCGCgCA |
| MA0259.1 | HIF1A::ARNT | Consensus | 11.2 | forward | GGACGTGC |
| MA0259.1 | HIF1A::ARNT | APOE3, Rs429358/T | 11.2 | forward | GGACGTGt |
| MA0259.1 | HIF1A::ARNT | APOE4, Rs429358/C | 9.6 | forward | GGACGTGc |

APOE variant rs429358 is indicated in small cap.

"APOE4 motif" (FIG. 5e) and creates a de novo recognition sequence for the transcription factor NRF1 in AD neurons. The APOE4 transcriptional enhancer element can extend beyond the central APOE4 motif, encompassing neighboring sequences on APOE4 exon 4.

Enhancers exert their regulatory function through binding of cell-type specific transcription factors. Therefore, the DNA sequence of the APOE4 motif was searched for putative transcription factor binding sites using binding profiles from the JASPAR CORE database of experimentally defined transcription factor binding sites for eukaryotes (jaspar.genereg.net). A score was calculated for the probed sequence that provided a measure of similarity to the transcription factor consensus sequence. This analysis of the APOE4 motif resulted in a statistically significant hit for the nuclear respiratory factor 1 (NRF1) consensus binding motif (FIG. 7a). Table 4 shows the highest values obtained for APOE4 rs429358/C variant, compared to the score and relative score obtained for APOE3 at the same position. The novel NRF1 binding site created by the APOE4 variant is located on the reverse strand (FIG. 7b), with a score of 11.859 while APOE3 resulted in a score of 3.879. As a comparison, the highest score to be expected for the NRF1 consensus sequence in JASPAR is 18.058. Score is 0 if the sequence has equal probability for being a functional or a random site. Moreover, the APOE4 variant changes a non-consensus T nucleotide (A on the reverse strand) with 0

The NRF1 binding site of the APOE4 motif is a legitimate enhancer as these sequences can be positioned in both forward or reversed orientations, inside, downstream, or upstream of the regulated gene and most transcription factor binding sites can occur in both orientations in promoters or enhancers.

Age, head trauma, poorly controlled diabetes as well as common virus infections are known risk factors influencing AD onset, progression and outcome. These triggers all stimulate NRF1 activity[lxx, lxxi, lxxii, lxxiii]. The present inventors have discovered that the APOE4 variant creates a de novo binding site for NRF1, which is part of the APOE4 motif that regulates the expression of AD causing genes.

In some instances enhancers modulate DNA transcription over long distances. For instance, Sonic Hedgehog enhancer ZRS is situated 1 Mb upstream of the gene that it regulates. The ability of enhancers to interact with promoters is not limited to genes located in cis on the same chromosome. Gene regulatory elements have been found to engage in direct physical interactions with target genes on other chromosomes[lxxiv]. Yet an important property of enhancers is that their readout is context-specific[lxxv], so too are the effects of mutations within them, that may alter a gene's expression in one tissue, but not another. Variations in distantly acting enhancers are known to contribute to disease (e.g. Beta-thalassaemia, Hirschsprung's disease, preaxial polydactyly). A common single nucleotide polymorphism (SNP) that alters a binding site for the lymphoid enhancer-binding factor 1 (LEF1) transcription factor, reducing LEF1 responsiveness and enhancer activity in cultured human keratinocytes has been found to contribute to the classic blond hair phenotype found in northern Europeans[lxxvi].

The present inventors have discovered that the APOE4 motif acts as an enhancer causing improper transcription of a distant gene in AD vulnerable neurons, defined as the AD causing gene.

Enhancers can affect the transcription of genes located in cis as far as 2 Mb away on the same chromosome, but they can also affect the transcription of genes located on a different chromosome brought into spatial proximity to the enhancer by protein-protein, DNA-DNA or protein-DNA interactions. Several genes located upstream and downstream of the APOE4 motif can affect pathways involved in AD.

In some embodiments, "APOE4 motif-mediated gene" means any gene located within 2 Mb (2 megabases=2 million bases) upstream or downstream of the APOE4 motif centered on rs429358 of chromosome 19. Still in other embodiments, the term "APOE4 motif-mediated gene" or the "expression product" refers to the gene or the expression product, respectively, that is modulated (e.g., either increased or decreased) by the presence of APOE4 allele compare to other APOE alleles. In some cases, the activity of APOE4 motif-mediated gene or the expression product thereof is increased compared to other APOE alleles. In other cases, the activity of the gene or the expression product thereof is reduced compared to other APOE alleles. A transcription product of such a gene includes any RNA transcript based on such gene, including any microRNA or mRNA (whether the mRNA transcript is primary, spliced, edited, modified or mature). An "APOE4 motif-mediated gene expression product" as used herein means a polypeptide translated from an mRNA transcript of an APOE4 motif-mediated gene, although it is sometimes colloquially used to refer to the RNA transcription product of a gene. Such polypeptide may be nascent or processed into a mature or modified form of the protein.

A representative list of the APOE4 motif-mediated genes, including genes located on chromosome 19 in a 2 Mb window around the APOE motif, was compiled from the GRCh38.p5 *Homo sapiens* Genome Assembly of EnsEmbl[lxxvii] and is provided in Table 3. These genes include PSG1, XRCC1, PINLYP, IRGQ, ZNF576, SRRM5, ZNF428, PLAUR, SMG9, ZNF224, ZNF285, ZNF180, PVR, BCL3, CBLC, BCAM, PVRL2/NECTIN2, CLPTM1, RELB, CLASRP, GEMIN7, MARK4, PPP1R37, NKPD1, TRAPPC6A, BLOC1S3, EXOC3L2, CKM, KLC3, ERCC2, PPP1R13L, ERCC1, FOSB/deltaFOSB, RTN2, VASP, OPA3, GPR4, EML2, GIPR, SNRPD2, QPCTL, FBXO46, SIX5, SYMPK, FOXA3, MYPOP, NOVA2, CCDC61, HIF3A, PPP5C, PNMA8A/PNMAL1, PNMA8B/PNMAL2, DACT3, STRN4 and FKRP. Still in other embodiments, the gene that is expressed by APOE4 motif comprises FBXO46, SNRPD2, ZNF285, ZNF180, PVR, ERCC2, QPCTL, SYMPK, MYPOP, CCDC61, XRCC1, ZNF576, ZNF428, SMG9, PPP5C, PNMA8A/PNMAL1, PNMA8B/PNMAL2, DACT3, STRN4, FKRP, RTN2, IRGQ, SRRM5, FOXA3, FOSB/deltaFOSB, SIX5 and GPR4. In a further embodiment the gene that is expressed by the APOE4 motif comprises FBXO46, PPP5C, FKRP, SYMPK, FOSB/deltaFOSB, FOXA3, GPR4, PSG1, PPP1R13L, EXOC3L2, SIX5, PLAUR and KLC3.

TABLE 3

Representative list of genes located within about 2 Mb upstream and downstream of APOE4 motif (genome assembly GRCh38.p5)

| Gene | Location |
|---|---|
| PSG1 (ENSG00000231924) | 19: 42866464-42879822 |
| PSG7 (ENSG00000221878) | 19: 42906822-43082671 |
| PSG2 (ENSG00000242221) | 19: 43064211-43083045 |
| PSG5 (ENSG00000204941) | 19: 43166256-43186536 |
| PSG4 (ENSG00000243137) | 19: 43192702-43207299 |
| PSG9 (ENSG00000183668) | 19: 43211791-43269530 |
| CD177 (ENSG00000204936) | 19: 43353659-43363172 |
| TEX101 (ENSG00000131126) | 19: 43401496-43418597 |
| LYPD3 (ENSG00000124466) | 19: 43460787-43465660 |
| PHLDB3 (ENSG00000176531) | 19: 43474954-43504935 |
| ETHE1 (ENSG00000105755) | 19: 43506719-43527244 |
| ZNF575 (ENSG00000176472) | 19: 43525497-43536130 |
| XRCC1 (ENSG00000073050) | 19: 43543040-43580473 |
| L34079.2 (ENSG00000268361) | 19: 43554692-43593036 |
| PINLYP (ENSG00000234465) | 19: 43576800-43583964 |
| IRGQ (ENSG00000167378) | 19: 43584369-43596135 |
| ZNF576 (ENSG00000124444) | 19: 43596392-43601157 |
| SRRM5 (ENSG00000226763) | 19: 43596617-43614497 |
| ZNF428 (ENSG00000131116) | 19: 43607219-43619874 |
| CADM4 (ENSG00000105767) | 19: 43622368-43639839 |
| PLAUR (ENSG00000011422) | 19: 43646095-43670547 |
| IRGC (ENSG00000124449) | 19: 43716010-43720021 |
| SMG9 (ENSG00000105771) | 19: 43727992-43754990 |
| KCNN4 (ENSG00000104783) | 19: 43766533-43781257 |
| LYPD5 (ENSG00000159871) | 19: 43795929-43827206 |
| ZNF283 (ENSG00000167637) | 19: 43827292-43852017 |
| ZNF404 (ENSG00000176222) | 19: 43872363-43901385 |
| ZNF45 (ENSG00000124459) | 19: 43912629-43935278 |
| ZNF221 (ENSG00000159905) | 19: 43951223-43967709 |
| ZNF155 (ENSG00000204920) | 19: 43967862-43998325 |
| ZNF230 (ENSG00000159882) | 19: 44002948-44013926 |
| ZNF222 (ENSG00000159885) | 19: 44025342-44033112 |
| AC084219.2 (ENSG00000267022) | 19: 44025354-44087318 |
| ZNF223 (ENSG00000178386) | 19: 44051367-44067991 |
| ZNF284 (ENSG00000186026) | 19: 44072144-44089613 |
| ZNF224 (ENSG00000267680) | 19: 44094339-44109886 |
| ZNF225 (ENSG00000256294) | 19: 44112181-44134816 |
| ZNF234 (ENSG00000263002) | 19: 44141557-44160309 |
| ZNF226 (ENSG00000167380) | 19: 44165073-44178381 |
| ZNF227 (ENSG00000131115) | 19: 44207547-44237268 |
| ZNF235 (ENSG00000159917) | 19: 44228729-44305046 |
| ZNF233 (ENSG00000159915) | 19: 44259880-44275317 |
| ZNF112 (ENSG00000062370) | 19: 44326555-44367217 |
| CTC-512J12.6 (ENSG00000267173) | 19: 44329695-44401608 |
| ZNF285 (ENSG00000267508) | 19: 44382298-44401608 |
| ZNF229 (ENSG00000278318) | 19: 44417519-44448578 |
| ZNF180 (ENSG00000167384) | 19: 44474428-44500524 |
| CEACAM20 (ENSG00000273777) | 19: 44501677-44529788 |
| IGSF23 (ENSG00000216588) | 19: 44613630-44636781 |
| PVR (ENSG00000073008) | 19: 44643798-44663583 |
| CEACAM19 (ENSG00000186567) | 19: 44662278-44684359 |
| CEACAM16 (ENSG00000213892) | 19: 44699151-44710714 |
| BCL3 (ENSG00000069399) | 19: 44747705-44760044 |
| MIR8085 (ENSG00000277736O) | 19: 44758657-44758721 |
| CBLC (ENSG00000142273) | 19: 44777869-44880064 |
| BCAM (ENSG00000187244) | 19: 44809059-44821420 |
| PVRL2 (ENSG00000130202) | 19: 44846175-44889228 |
| TOMM40 (ENSG00000130204) | 19: 44890569-44903689 |
| APOE (ENSG00000130203) | 19: 44905754-44909393 |
| AC005779.2 (ENSG00000267545) | 19: 45179822-45202444 |
| APOC1 (ENSG00000130208) | 19: 44914247-44919349 |
| APOC4 (ENSG00000267467) | 19: 44942238-44945496 |
| APOC4-APOC2 (ENSG00000224916) | 19: 44942238-44949565 |
| APOC2 (ENSG00000234906) | 19: 44946035-44949565 |
| CLPTM1 (ENSG00000104853) | 19: 44954585-44993341 |
| RELB (ENSG00000104856) | 19: 45001430-45038198 |
| CLASRP (ENSG00000104859) | 19: 45039040-45070956 |
| ZNF296 (ENSG00000170684) | 19: 45071500-45076588 |
| GEMIN7 (ENSG00000142252) | 19: 45079195-45091524 |
| MARK4 (ENSG00000007047) | 19: 45079288-45305283 |
| PPP1R37 (ENSG00000104866) | 19: 45091396-45148077 |
| NKPD1 (ENSG00000179846) | 19: 45149750-45160150 |
| TRAPPC6A (ENSG00000007255) | 19: 45162928-45178237 |
| BLOC1S3 (ENSG00000189114) | 19: 45178745-45181801 |
| AC005779.2 (ENSG00000267545) | 19: 45179822-45202444 |
| EXOC3L2 (ENSG00000130201) | 19: 45212621-45234211 |
| CKM (ENSG00000104879) | 19: 45306414-45322977 |

TABLE 3-continued

Representative list of genes located within about 2 Mb upstream
and downstream of APOE4 motif (genome assembly GRCh38.p5)

| Gene | Location |
|---|---|
| KLC3 (ENSG00000104892) | 19: 45333434-45351520 |
| ERCC2 (ENSG00000104884) | 19: 45349837-45370918 |
| PPP1R13L (ENSG00000104881) | 19: 45379634-45406349 |
| CD3EAP (ENSG00000117877) | 19: 45406209-45410766 |
| ERCC1 (ENSG00000012061) | 19: 45407333-45478828 |
| FOSB (ENSG00000125740) | 19: 45467995-45475179 |
| MIR6088 (ENSG00000275726) | 19: 45436654-45436704 |
| RTN2 (ENSG00000125744) | 19: 45485289-45497061 |
| PPM1N (ENSG00000213889) | 19: 45488777-45502510 |
| VASP (ENSG00000125753) | 19: 45506579-45526983 |
| OPA3 (ENSG00000125741) | 19: 45527427-45602212 |
| GPR4 (ENSG00000177464) | 19: 45589764-45602208 |
| EML2 (ENSG00000125746) | 19: 45606994-45645629 |
| MIR330 (ENSG00000199066) | 19: 45638994-45639087 |
| GIPR (ENSG00000010310) | 19: 45668244-45683724 |
| MIR642A (ENSG00000207773) | 19: 45674928-45675024 |
| SNRPD2 (ENSG00000125743) | 19: 45687454-45692569 |
| QPCTL (ENSG00000011478) | 19: 45692483-45703989 |
| FBXO46 (ENSG00000177051) | 19: 45710629-45730904 |
| BHMG1 (ENSG00000237452) | 19: 45733251-45764534 |
| SIX5 (ENSG00000177045) | 19: 45764785-45769226 |
| DMPK (ENSG00000104936) | 19: 45769717-45782552 |
| AC011530.4 (ENSG00000268434) | 19: 45779437-45785973 |
| DMWD (ENSG00000185800) | 19: 45782947-45792802 |
| RSPH6A (ENSG00000104941) | 19: 45795710-45815319 |
| SYMPK (ENSG00000125755) | 19: 45815410-45863290 |
| FOXA3 (ENSG00000 170608) | 19: 45863989-45873797 |
| IRF2BP1 (ENSG00000170604) | 19: 45883607-45886170 |
| MYPOP (ENSG00000176182) | 19: 45890020-45902604 |
| NANOS2 (ENSG00000188425) | 19: 45913214-45914870 |
| NOVA2 (ENSG00000104967) | 19: 45933734-45973546 |
| CCDC61 (ENSG00000104983) | 19: 45995461-46021318 |
| MIR769 (ENSG00000211580} | 19: 46019153-46023065 |
| PGLYRP1 (ENSG00000008438) | 19: 46019153-46023065 |
| IGFL4 (ENSG00000204869) | 19: 46039748-46077118 |
| IGFL3 (ENSG00000188624) | 19: 46120071-46124674 |
| IGFL2 (ENSG00000204866) | 19: 46143106-46161299 |
| IGFL1 (ENSG00000188293) | 19: 46229752-46231243 |
| HIF3A (ENSG00000124440) | 19: 46297046-46343433 |
| PPP5C (ENSG00000011485) | 19: 46346994-46392981 |
| CCDC8 (ENSG00000169515) | 19: 46410372-46413584 |
| PNMAL1 (ENSG00000182013) | 19: 46466491-46471563 |
| PPP5D1 (ENSG00000230510) | 19: 46480796-46601200 |
| PNMAL2 (ENSG00000204851) | 19: 46486906-46496498 |
| CALM3 (ENSG00000160014) | 19: 46601074-46610793 |
| PTGIR (ENSG00000160013) | 19: 46620468-46625118 |
| GNG8 (ENSG00000167414) | 19: 46634076-46634685 |
| DACT3 (ENSG00000197380) | 19: 46647612-46661138 |
| PRKD2 (ENSG00000105287) | 19: 46674275-46717127 |
| MIR320E (ENSG00000211513) | 19: 46709271-46709382 |
| STRN4 (ENSG00000090372) | 19: 46719507-46746994 |
| FKRP (ENSG00000181027) | 19: 46746046-46776988 |
| SLC1A5 (ENSG00000105281) | 19: 46774883-46788594 |
| AC008622.1 (ENSG00000280050) | 19: 46792971-46793189 |
| AP2S1 (ENSG00000042753) | 19: 46838136-46850992 |
| ARHGAP35 (ENSG00000160007) | 19: 46918676-47005077 |
| NPAS1 (ENSG00000130751) | 19: 47019820-47045775 |

Progression through the cell cycle in eukaryotes is achieved through highly controlled phosphorylation and degradation of cell-cycle-regulating proteins. The SCF controls the G1/S and G2/M phases transition through specific binding and ubiquitination of cyclins (e.g. FBXW7 binds directly to cyclin E and FBXO31 mediates cyclin D1 degradation). F-box proteins are themselves intrinsically unstable and are degraded by the ubiquitin-dependent pathway, probably through auto-ubiquitination within the assembled SCF complex thereby enabling cells to rapidly adapt to changing environmental conditions and progress through the cell cycle[lxxviii]. Cell cycle reentry has been observed in AD neurons and thus implicates F-box proteins function. FBXO46 interferes with the normal amyloidogenic pathway.

Studies have suggested that alterations in reticulons, such as increased aggregation, impair BACE1 binding, increasing amyloid-β production, and facilitating reticulon deposition in dystrophic neurites. Improper expression of RTN2 interferes with the normal amyloidogenic pathway in AD neurons.

APP transgenic mice with reduced KLC1 function exhibit earlier and accentuated brain amyloid plaques, thought to be caused by abnormal APP transport and/or cleavage. Inappropriate expression of the motor proteins subunit KLC3 in AD neurons interferes with the normal amyloidogenic pathway.

A list of genes located on chromosome 19 in a 2 Mb window around the APOE motif from the GRCh38.p2 *Homo sapiens* Genome Assembly of EnsEmbl is provided in Table 3. This list was then compared with a list of NRF1 target genes as determined from a published ChIP-Seq-Based data retrieved from ChIP-Seq experiments performed in SK-N-SH human neuroblastoma cells for the ENCODE project (encodeproject.org, DDBJ Sequence Read Archive, accession number of SRP007993)[lxvi]. By this analysis the F-box protein FBXO46 was identified to be among the genes controlled by NRF1 and to be located in the vicinity of the APOE4 motif. FBXO46 is situated in 19q13.32, 0.8 Mb downstream from APOE. Other genes located in the vicinity of the APOE4 motif and controlled by NRF1 comprise of FBXO46, SNRPD2, ZNF285, ZNF180, PVR, ERCC2, QPCTL, SYMPK, MYPOP, XRCC1, ZNF576, ZNF428, SMG9, PPP5C, PNMA8A/PNMAL1, PNMA8B/PNMAL2, DACT3, STRN4 and FKRP. The APOE4 variant creates a de novo binding site for NRF1 and that within a genomic distance to the APOE4 motif known to be within reach of transcriptional enhancer activity, FBXO46 was determined to be a target gene. Without being bound by any theory, it is believed that the APOE4 motif mediates transcription via NRF1 in AD neurons. APOE4 motif-mediated expression of a gene refers to the stimulation or alternatively, repression of the expression of a gene.

NRF1 binding sites were also detected in the 5' DNA regions of RTN2, IRGQ, SRRM5, FOXA3, FOSB/deltaFOSB, SIX5 and GPR4. The 5' DNA regions of genes RTN2, IRGQ, SRRM5, FOXA3, FOSB/deltaFOSB, SIX5 and GPR4 encompassing −1000 bp+400 bp with respect to the transcription start site were subjected to a JASPAR 2016 database (http://jaspar2016.genereg.net/) search of NRF1 binding motifs. One NRF1 binding site with a score 11.490 was identified in the 5' region of RTN2, five NRF1 binding sites with scores ranging from 14.489 to 18.058 were identified in the 5' DNA region of IRGQ, and five NRF1 binding sites with scores ranging from 14.489 to 18.058 were identified (Table 5) in the 5' DNA region of SRRM5, three NRF1 binding sites with scores ranging from 10.857 to 17.077 were identified in the 5' DNA region of FOXA3, eight NRF1 binding sites with scores ranging from 10.228 to 18.058 were identified in the 5' DNA region of FOSB/deltaFOSB, three NRF1 binding sites with scores ranging from 14.200 to 18.058 were identified in the 5' DNA region of SIX5, and one NRF1 binding site with a score of 9.693 was identified in the 5' region of GPR4. We concluded that genes RTN2, IRGQ, SRRM5, FOXA3, FOSB/deltaFOSB, SIX5 and GPR4 are controlled by the transcription factor NRF1.

Cell cycle or tissue specific DNA binding transcription factors bound at promoters and enhancers recruit "looping" factors which setup contacts between distal enhancers and promoters. Such factors appear to form loops within more "structural" loops mediated by general factors like CCCTC binding factor (CTCF). CTCF and cohesin are involved in the formation of self-associating, long-range chromatin topological domain in the mammalian genome. The differential recruitment of CTCF in different cell types controls differential gene expression patterns by helping to establish cell-type-specific chromatin domains that control enhancer activities. Interaction between two CTCF molecules bound to their binding sites positively influences the expression of all the genes within the created loop. Numerous CTCF binding sites are present in the APOE genomic region, upstream as well as downstream of APOE.

Influence of environment, lifestyle, and medical condition on the onset of AD has been amply documented. Concordance rates for AD for monozygotic twins vary between 59% and 80%, depending on the study. Moreover, among monozygotic twins both affected by AD, differences in age of onset ranges from 0 to 15 years. In the case of APOE4, penetrance is about 67%. Thus, expression of the AD gene is dependent on triggers that will influence the outcome of the disease by inducing a secondary chromatin loop inside an AD neuron specific CTCF loop. The APOE4 motif becomes active when the required factors are present in the AD vulnerable neuron, thus explaining how external triggers affect expression of the disease. A DNA loop overlapping APOE is created by a neuron specific interaction between 2 CTCF molecules. In subjects carrying the APOE4 variant, the trigger specific transcription factor NRF1 induces the formation of a secondary chromatin loop and subsequently mediates expression of the AD causing gene. APOE3 does not create the NRF1 binding site and is thus not a neuron specific enhancer for this transcription factor and does not typically allow transcriptional regulation. Protective APOE2 may bind a repressor of transcription for this gene (FIG. 3).

Without being bound by any theory, it is believed that in response to environmental and physiological stresses, including but not limited to infection, cerebral hypoxia, hypoglycemia, or hyperinsulinemia, NRF1 is activated in AD neurons. In one non-limiting example, by binding to the APOE4 motif and the proximal promoter region of the FBXO46 gene, it is believed that NRF1 turns on the inappropriate expression of the AD causing gene FBXO46.

One of the key steps in the amyloidogenic pathway involves endocytosis of LRP1, Fe65 and APP in a ternary complex followed by processing by BACE1 and γ-secretase, APP phosphorylation at $Thr^{668}$, and finally retromer mediated retrograde trafficking of c99-APP into the TGN. All these steps must take place in precise order. Delay or malfunction in any of these steps lead to cell cycle re-entry, CDK5 hyperactivation, Tau/MAPT hyperphosphorylation and tangles formation and ultimately cell death.

Figure 4:
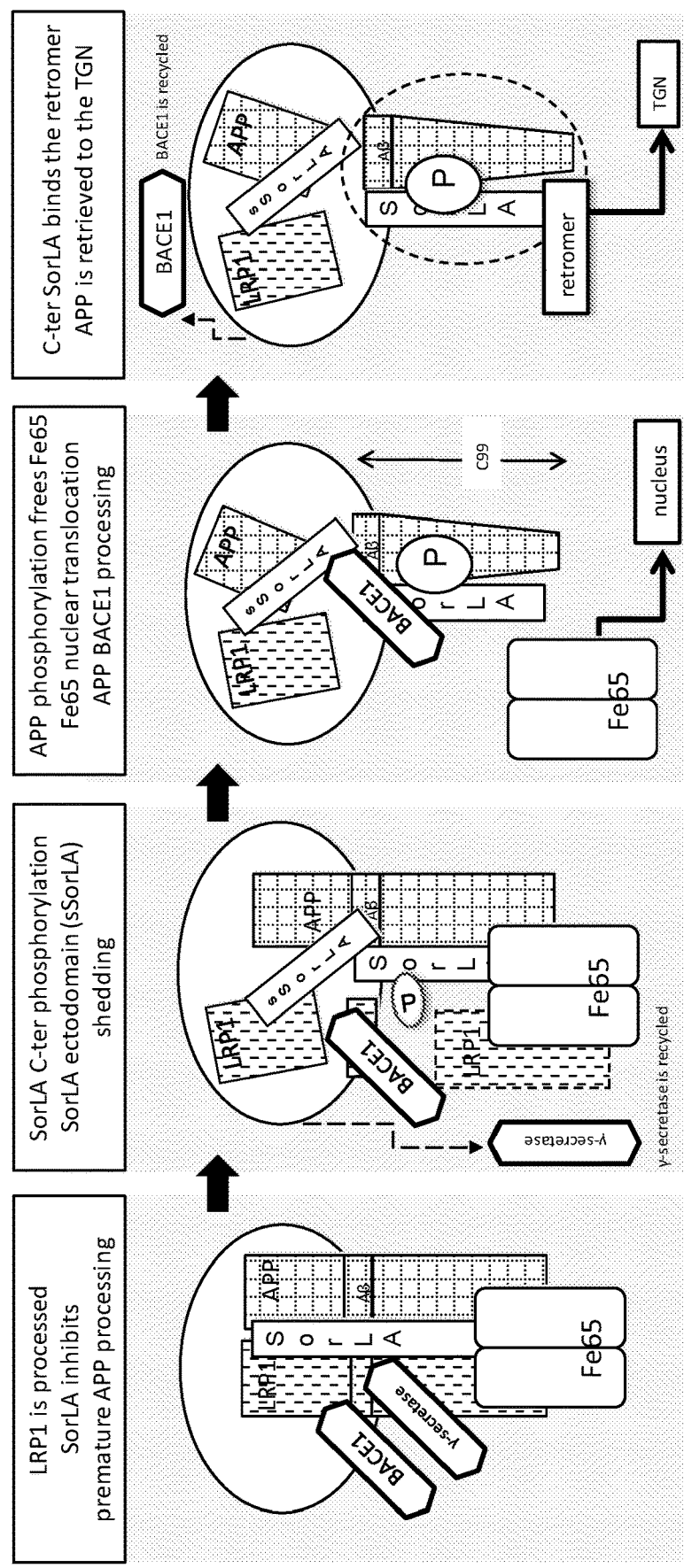
FIG. 4 illustrates the physiological role of SorLA in the amyloidogenic pathway in healthy subjects.

FIG. 4 illustrates the role of SorLA in the physiological amyloidogenic pathway. The SorLA interaction with APP inside the amyloidogenic trafficking endosome inhibits premature APP processing by BACE1. SorLA is phosphorylated and sheds its ectodomain after which APP is phosphorylated as well, which leads to a conformation change and frees Fe65. BACE1 gains access to APP and then is recycled after APP processing. The retromer is then able to bind to the C-tail of SorLA, which is still attached to C99, and retrieves APP to the TGN.

Overexpression of SorLA in AD neurons reduces amyloidogenic processing and senile plaque formation while inactivation of gene expression (as in knock-out mouse models) accelerates amyloidogenic processing and senile plaque formation.

Dysfunction of the amyloidogenic pathway in AD patients is linked to low SorLA concentration in neurons. We discovered that this low concentration in neurons of AD patients carrying the APOE4 variant is a direct consequence of the transcriptional enhancer activity of the APOE4 motif. In AD patients, APOE4 motif-mediated expression of the AD causing gene FBXO46 reduces levels of SorLA protein.

The present invention is based on the discovery of detailed knowledge of the underlying genetic mechanism for development of Alzheimer's disease as discussed above. In particular, such a discovery by the present inventors have provided methods for more accurate diagnose and/or treatment for Alzheimer's disease. This discovery also provides methods for preventing development of Alzheimer's disease (AD) in individuals, particular those individuals that are genetically predisposed to AD.

Based on the analysis of the gene structure, the present inventors have discovered that the APOE4 variant creates a de novo recognition motif for the neuron-specific transcription factor NRF1. An analysis of NRF1 target genes in the vicinity of the APOE4 variant identified FBXO46 as the AD causing gene. Based at least in part by this discovery, one aspect of the invention provides a method of inhibiting the function of this NRF1 recognition site created by the APOE4 motif to inter alia stabilize or improve the cognitive ability of subjects with AD.

In some embodiments, inhibition of APOE4 motif regulated gene expression is achieved by contacting a cell that is expressing a gene mediated by APOE4 motif with a molecule that is capable of inhibiting binding of a transcription factor to APOE4 motif (sometimes called a "decoy"). In some embodiments, the cell is a neuronal cell, a neuronal progenitor cell or a differentiated neuron.

Yet in another embodiment of the invention, the gene whose expression is mediated by the APOE4 motif is located on human chromosome 19 within 2 Mb of rs429358. Exemplary genes that are expressed by APOE4 motif include, but are not limited to, PSG1, XRCC1, PINLYP, IRGQ, ZNF576, SRRM5, ZNF428, PLAUR, SMG9, ZNF224, ZNF285, ZNF180, PVR, BCL3, CBLC, BCAM, PVRL2/NECTIN2, CLPTM1, RELB, CLASRP, GEMIN7, MARK4, PPP1R37, NKPD1, TRAPPC6A, BLOC1S3, EXOC3L2, CKM, KLC3, ERCC2, PPP1R13L, ERCC1, FOSB/deltaFOSB, RTN2, VASP, OPA3, GPR4, EML2, GIPR, SNRPD2, QPCTL, FBXO46, SIX5, SYMPK, FOXA3, MYPOP, NOVA2, CCDC61, HIF3A, PPP5C, PNMA8A/PNMAL1, PNMA8B/PNMAL2, DACT3, STRN4 and FKRP and a combination thereof. Still in other embodiments, the gene whose expression is mediated by APOE4 motif comprises FBXO46, SNRPD2, ZNF285, ZNF180, PVR, ERCC2, QPCTL, SYMPK, MYPOP, CCDC61, XRCC1, ZNF576, ZNF428, SMG9, PPP5C, PNMA8A/PNMAL1, PNMA8B/PNMAL2, DACT3, STRN4, FKRP, RTN2, IRGQ, SRRM5, FOXA3, FOSB/deltaFOSB, SIX5, GPR4. In a further embodiment, the gene whose expression is mediated by the APOE4 motif comprises FBXO46, PPP5C, FKRP, SYMPK, FOSB/deltaFOSB, FOXA3, GPR4, PSG1, PPP1R13L, EXOC3L2, SIX5, PLAUR, KLC3.

One particular embodiment of the invention provides a method for inhibiting binding of a transcription factor to the APOE4 motif. Still in another embodiment the invention provides a method for inhibiting expression of a gene mediated by binding of a transcription factor to APOE4 motif. It should be appreciated that the term "inhibiting" when referring to a gene expression means the amount of gene transcribed and/or translated is reduced by at least about 10%, typically by at least about 20%, or arrested substantially completely (i.e., >90% reduction) in the presence of a molecule of the invention compared to the same cell line in the absence of the molecule. One skilled in the art can readily measure the amount of inhibition using any of the methods that are known.

One specific embodiment of the invention provides a molecule that is capable of inhibiting the APOE4 motif-mediated expression of a gene by inhibiting the transcription factor NRF1. As used herein, the term "inhibiting transcription factor NRF1" includes inhibiting binding of NRF1 to APOE4 motif, inhibiting production of NRF1, e.g., by inhibiting transcription of NRF1 gene and/or by inhibiting translation of mRNA that encodes NRF1, etc.

The molecule used for inhibiting APOE4 motif-mediated expression of a gene by inhibiting the transcription factor NRF1 includes, but not limited to, a drug, an oligonucleotide, a peptide or a derivative thereof or a combination thereof. In some embodiments, sometimes called a "decoy oligonucleotide", the oligonucleotide is a subsequence or a segment of SEQ ID NO:1. In particular, the oligonucleotide is 11 to 30 nucleotides in length comprising consecutive nucleotide subsequence within SEQ ID NO: 1. In one instance, the decoy oligonucleotide is a single-strand oligonucleotide. Yet in another instance, the decoy oligonucleotide is a double-strand oligonucleotide.

The term "oligonucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). A "subsequence" or "segment" refers to a sequence of nucleotides that comprise a part of a longer sequence of nucleotides.

In another embodiment of the invention, a molecule is an oligonucleotide that can bind to APOE4 motif that binds to NRF1. In some instances, the oligonucleotide is substantially complementary to the APOE4 motif that binds to NRF1. The term "substantially complementary to" or "substantially the sequence" refers to sequences which hybridize to the sequences provided under stringent conditions and/or sequences having sufficient homology with APOE4 motif that binds to NRF1 such that the oligonucleotides of the invention hybridize to the APOE4 motif sequence. "Substantially" the same as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the APOE4 motif sequence that binds to NRF1. Unless the context requires otherwise, the term "APOE4 motif" refers to a portion of the E4 variant of the APOE gene that binds to NRF1.

Yet in some embodiments, the oligonucleotide is a phosphorothioate oligonucleotide, a methylphosphonate oligonucleotide, a phosphoamidite oligonucleotide, a peptide nucleic acid oligonucleotide, a locked-nucleic acid-modified oligonucleotide, and combinations thereof.

In another embodiment, the oligonucleotide is fused to a cell penetrating peptide.

In some embodiments, the molecule is a peptide that is a fragment of the NRF1 protein that can bind to the APOE4 motif. In a preferred embodiment, said peptide lacks the transactivation domain of NRF1 and encompasses amino acid residues 78 to 304. In a further preferred embodiment said peptide comprises the amino acid residues 110 to 304 of the NRF1 sequence or a fragment thereof.

In a further embodiment NRF1 peptides and fragments thereof are fused to a cell penetrating peptide to facilitate intracellular delivery of the NRF1 peptides and fragments thereof. In another embodiment the cell penetrating peptide has the amino acid sequence GRKKRRQRRRPQ. In another embodiment, the NRF1 peptide or fragment thereof is encoded by an expression vector.

The molecule can further include a pharmaceutically acceptable carrier. The terms "pharmaceutically acceptable carrier" and "pharmaceutically acceptable excipient" are used interchangeably herein and refer to an excipient that is useful in preparing a pharmaceutical composition that is generally safe, non-toxic and neither biologically nor otherwise undesirable, and includes excipient that is acceptable for human pharmaceutical use.

Still in other embodiments, the cell comprises a neuronal cell. Neuronal cells can be neuronal progenitor cells as well as differentiated neurons. Methods of the invention are applicable to a neuronal progenitor cell, a differentiated neuron or a combination thereof.

Methods of the invention include molecules that can inhibit APOE4 mediated gene expression by binding to the APOE4 motif, the transcription factor, or both.

Another aspect of the invention provides a method for identifying a molecule that can inhibit binding of a transcription factor to the APOE4 motif. This method can be used to identify a lead candidate for drug development for treatment of AD. The method typically involves an in vitro or a biochemical assay that does not contain whole cells. The assay may contain cell extracts or other cellular components. One skilled in the art having read the present disclosure can readily recognize suitable in vitro assay conditions necessary to identify a molecule that can inhibit binding of a transcription factor to APOE4 motif. Typically, it will be an in vitro binding assay in which direct binding of NRF1 to an immobilized APOE4 motif oligonucleotide is measured. Exemplary suitable in vitro assays include, but are not limited to, a surface plasmon resonance and an electrophoretic mobility shift assay (EMSA). Briefly, in EMSA a radioactively labeled APOE4 motif oligonucleotide is incubated with a recombinant NRF1 and a molecule to be tested as being a possible lead drug candidate. The ability of the molecule to inhibit binding of the recombinant NRF1 to the labeled APOE4 motif is then analyzed by gel electrophoresis. If NRF1 is bound to the labeled APOE4 motif (that is the molecule did not significantly inhibit binding), the observed mobility of the labeled APOE4 motif is shifted towards higher molecular weight.

High-Throughput Screening Assays:

Screening assays of the invention are designed to identify modulation of a function, activity or amount of an APOE4 motif-mediated gene or gene expression product, e.g., the mRNA or the protein generated from the gene sequence. As used herein the term "modulation" means any change in activity of a function or amount of the transcribed gene, mRNA or protein, (together which are sometimes called the "target") including any change in transcription rate or expression level, and includes inhibition or activation, and antagonist and agonist effects on the biochemical or biological activity of the target. Throughout this disclosure, the term "change" when referring to any biological activity, e.g., APOE4 motif-mediated gene expression or activity of APOE4 motif-mediated gene expression product, means the value is statistically different from a control (i.e., $p<0.25$, often $p<0.1$, and more often $p<0.05$). The term "control" of gene expression or activity of a gene expression product refers to a standard level against which gene expression or the activity of the gene expression product, respectively, in a patient sample is or can be compared. In some embodiments, the control can be relative to cells having no APOE4 allele, meaning the level compared to a non-APOE4 motif-mediated gene expression or the expression product thereof. This allows a determination based on the expression or biological activity against cells or subject without APOE4 allele. The term "control" can also be used in reference to the level established in a sample from the subject or from a population of individuals which is believed to carry APOE4 allele. In some cases, the terms "negative control", i.e., against subjects or cells without APOE4 allele or "positive control", i.e., against subjects or cells with APOE4 allele, is used to further distinguish the meaning of "control." In this manner, the level of APOE4 motif-modified gene expression or the level of activity of APOE4 motif-modified gene expression product can be compared against the "negative control" or the "positive control."

This specification discloses diverse functions of APOE4 motif-mediated genes, either known from the art or implied from proteins of the same class, that may be used to assess modulation. Some functions may be assessed directly, such as the catalyzing of a specific reaction, or less directly, such as by measuring the accumulation of a downstream product. Many assay designs are available to those skilled in the art. Preferred assays are optimized for speed, efficiency, signal detection and low reagent consumption. (Zhang et al. (1999) J. Biomolec. Screen. 4(2):67). Assays can be reporter assays measuring gene transcription, gene translation or a biological activity of the gene expression product. Assays can be developed in neurological cells or cells derived from a mammalian neurological cell or a mammalian pluripotent stem cell. The examples below include description of assays for accumulation of SorLa protein, which is an example of one such downstream product which can be measured in neurological cells to identify compounds which inhibit the activity of one or more of the APOE motif-mediated gene products. Based on the invention herein, those of skill in the art can now predictably develop screening assays for potential AD therapeutic agents based on assays designed to measure if the compound modulates the protein functions disclosed herein, and other functions known or to be discovered now that their significance is understood.

In some embodiments, the screening assays of the invention, either cellular, cell extract or biochemically based, are designed for testing a plurality of compounds (e.g., millions) through high-throughput screening of chemical libraries.

Chemical libraries of test compounds that may be screened to identify a modulator can be obtained from numerous available resources or using any of the numerous approaches in library synthesis methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). See also Dolle et al. (2010) Comprehensive Survey of Chemical Libraries for Drug Discovery and Chemical Biology: 2009. J. Comb. Chem., 2010, 12 (6), pp 765-806.

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Test compounds which successfully modulate, especially inhibit, the activity of an APOE4 motif-mediated gene or expression product are attractive candidates for further investigation and secondary screening in alternative assays for potential use in treating AD or mild cognitive disorder. Compounds are considered "potentially useful for treatment" when first identified in a screening assay, because it is well known that initial successful hits rarely contain all the required features for a successful pharmaceutical. They are however extremely useful to allow researchers to identify a chemical core structure shared among compounds that effectively modulates or inhibits the target activity. Typically, when a core structure is identified, an extensive library of possibly thousands of related compounds is further developed with the aim of identifying a lead compound that meets all the criteria for a successful pharmaceutical candidate. The assay is used repeatedly through many rounds of screening of up to millions of compounds to ultimately identify a small group of lead compounds, one of which may eventually become an approved therapeutic agent.

In some embodiments of the invention, a possible lead molecule for treatment of AD identified by methods of the invention has 50% inhibition concentration ($IC_{50}$) of about 500 µM or less, typically about 100 µM or less, often about 50 µM or less, more often about 10 µM or less, and most often about 500 nM or less.

Still another aspect of the invention provides a method for inhibiting APOE4 motif-mediated expression of a gene in a cell. It should be appreciated that throughout this disclosure the term "APOE4 motif-mediated expression of a gene" refers to expression of a gene caused by, due to, or mediated by binding of a transcription factor to APOE4 motif. Expression of a gene refers to induction or repression of said gene. Such a method includes contacting a cell that is expressing or is capable of expression a gene mediated by the APOE4 motif with a molecule that is capable of inhibiting expression of said gene. In one embodiment, the gene that is expressed by the APOE4 motif is located on human chromosome 19 within 2 Mb of rs429358. Exemplary genes that are expressed by the APOE4 motif include, but are not limited to PSG1, XRCC1, PINLYP, IRGQ, ZNF576, SRRM5, ZNF428, PLAUR, SMG9, ZNF224, ZNF285, ZNF180, PVR, BCL3, CBLC, BCAM, PVRL2/NECTIN2, CLPTM1, RELB, CLASRP, GEMIN7, MARK4, PPP1R37, NKPD1, TRAPPC6A, BLOC1S3, EXOC3L2, CKM, KLC3, ERCC2, PPP1R13L, ERCC1, FOSB/deltaFOSB, RTN2, VASP, OPA3, GPR4, EML2, GIPR, SNRPD2, QPCTL, FBXO46, SIX5, SYMPK, FOXA3, MYPOP, NOVA2, CCDC61, HIF3A, PPP5C, PNMA8A/PNMAL1, PNMA8B/PNMAL2, DACT3, STRN4 and FKRP. In particular, methods of the invention include inhibiting expression of the following genes that are expressed by binding of a transcription factor to the APOE4 motif: FBXO46, SNRPD2, ZNF285, ZNF180, PVR, ERCC2, QPCTL, SYMPK, MYPOP, CCDC61, XRCC1, ZNF576, ZNF428, SMG9, PPP5C, PNMA8A/PNMAL1, PNMA8B/PNMAL2, DACT3, STRN4, FKRP, RTN2, IRGQ, SRRM5, FOXA3, FOSB/deltaFOSB, SIX5 and GPR4 or a combination thereof. In a further embodiment, the APOE4 motif-mediated gene comprises FBXO46, PPP5C, FKRP, SYMPK, FOSB/deltaFOSB, FOXA3, GPR4, PSG1, PPP1R13L, EXOC3L2, SIX5, PLAUR, KLC3 or a combination thereof. In one specific embodiment, the gene whose expression is inhibited by methods of the invention is MIR4531, MIR8085, MIR6088, MIR330, MIR642A, MIR642B, MIR769, MIR320E, where the molecule used for inhibition is a locked nucleic acid modified oligonucleotide.

Clinical use of methods of the invention includes a method for treating a subject suffering from AD or mild cognitive impairment. Methods of the invention include determining the APOE genotype present in said subject; and (a) if said subject carries the APOE4 allele, administering the subject with a molecule that is capable of inhibiting binding of a transcription factor to APOE4 motif; or (b) if the subject does not carry the APOE4 allele, administering the subject with a molecule that is different from the molecule that inhibits binding of a transcription factor to APOE4 motif. In some embodiments, the step of determining the APOE genotype in the subject comprises a step of determining whether the subject is homozygous or heterozygous for APOE4.

The molecule of the invention can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the molecule of the invention may be incorporated with excipient and used in the form of ingestible tablets, buccal tablets, troches, capsules, elixirs, suspensions, syrups, wafers, and the like. Such compositions and preparation can contain at least 0.1% of molecule of the invention. The percentage of the compositions and preparation can, of course, be varied and can conveniently be between about 1 to about 10% of the weight of the unit. The amount of molecule of the invention in such therapeutically useful compositions is such that a suitable dosage will be obtained. Preferred compositions or preparations according to the present invention are prepared such that an oral dosage unit form contains from about 1 to about 1000 mg of molecule of the invention.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the molecule of the invention, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the molecule of the invention can be incorporated into sustained-release preparations and formulation.

The molecule of the invention can also be administered parenterally. Solutions of the molecule of the invention as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the molecule of the invention in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The physician will determine the dosage of the molecule of the invention which will be most suitable for prophylaxis or treatment and it will vary with the form of administration and the particular molecule chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

Examples

Analysis of the DNA Sequence Overlapping the APOE Alleles:

The two SNPs determining the APOE alleles, rs429358 and rs7412, are located 138 bp apart on exon 4 (FIG. 5a). We aligned the DNA sequences overlapping these SNPs and observed that they are very similar (FIG. 5b).

Moreover, a rare APOE variant Val236Glu located on APOE exon 4 (r5199768005, Val254Glu in the full length sequence, FIG. 5c) was found to be significantly associated with a marked reduction in risk of AD (P=7.5×10$^{-5}$; OR=0.10 [0.03 to 0.45])[lxxix]. The sequence overlapping this polymorphism was analyzed and found that it is very similar to the DNA sequence harboring the APOE4 rs429358 SNP (FIG. 5d).

As rs429358 is the genetic variant determining the APOE ε4 allele, the sequence "TGGAGGACGTGCGC-GGCCGCCTGG" (SEQ ID NO:1) located around rs429358 was defined as the "APOE4 motif" (FIG. 5e).

Occurrence of APOE4 Motif in the Human Genome:

A Basic Local Alignment Search Tool (BLAST) analysis was conducted to find genomic regions similar to the APOE4 motif and found that this motif occurs in other genomic locations, for example in the IRF5 gene (FIG. 6a).

Hispanic populations show both a high risk of AD and Type 2 diabetes. A 32 bp insertion (r53842570) within intron 6 of the Calpain 10 (CAPN10) gene has been linked to higher risk of type 2 diabetes in the Mexican-American population. Two alleles are associated with this polymorphism, UCSNP-19: allele 1 harbors 2 repeats, and allele 3, 3 repeats of the 32-bp sequence. The reverse complementary sequence of this insertion (CAPN10Ins) was found to be very similar to the APOE4 motif (FIG. 6a).

Analysis of APOE Exon 4 DNA Sequence:

Rs429358 and rs7412 are both located inside exon 4 of the APOE gene and are part of a 880 bp CpG island (CGI) that extends from the end of intron 3 and overlaps the totality of exon 4. This APOE CGI normally carries a high level of methylation in the brain. As the DNA region overlapping these SNPs shows a high level of identity, the exon 4 DNA sequence was inspected in search of other structural elements and found numerous repeats interspersed across the whole exon, some of them very similar to the APOE4 motif (FIG. 6b). Enhancer sequences contain short DNA sequence motifs that serve as binding sites for transcription factors and other regulatory proteins. Exon 4 of APOE surprisingly harbors an arrangement of modular short-sequence motifs typical of transcriptional enhancer elements. The APOE4 transcriptional enhancer element can therefore extend beyond the central APOE4 motif, encompassing neighboring sequences on APOE4 exon 4.

Identification of an NRF1 Transcription Factor Binding Site in the APOE4 Motif:

Enhancers exert their regulatory function through binding of cell-type specific transcription factors. Thus, the DNA sequence around the APOE4 motif was searched for putative transcription factor binding sites using binding profiles from the JASPAR CORE database of experimentally defined transcription factor binding sites for eukaryotes (jaspar.genereg.net). A score is calculated for the probed sequence that provides a measure of similarity to the transcription factor consensus sequence. This analysis of the APOE4 motif resulted in a statistically significant hit for the nuclear respiratory factor 1 (NRF1) consensus binding motif (FIG. 7a). Table 4 shows the highest values obtained for APOE4 rs429358/C variant, compared to the score and relative score obtained for APOE3 at the same position. The novel NRF1 binding site created by the APOE4 variant is located on the reverse strand (FIG. 7b), with a score of 11.859 while APOE3 resulted in a score of 3.879. As a comparison, the highest score to be expected for the NRF1 consensus sequence in JASPAR is 18.058. Score is 0 if the sequence has equal probability for being a functional or a random site. Moreover, the APOE4 variant changes a non-consensus T nucleotide (A on the reverse strand) with 0 appearance in the nucleotide frequency matrix of the NRF1 consensus sequence into a highly conserved, consensus matching C nucleotide (G on the reverse strand) with 4275 appearances in the frequency matrix (FIG. 7c). Surprisingly and unexpectedly, it was discovered that the change of the T nucleotide (APOE3) to a C nucleotide (APOE4) creates a de novo NRF1 binding site.

This binding site is a legitimate enhancer as these sequences can be positioned in both forward or reversed orientations, inside, downstream, or upstream of the regulated gene and most transcription factor binding sites can occur in both orientations in promoters or enhancers.

Matching NRF1 Targets with Genes in Vicinity to the APOE4 Motif:

The NRF1 transcription factor is expressed in response to cellular injury/traumatic brain injury, metabolic and xenobiotic stress. It was realized that these are all factors associated with an increased AD risk. A list of all the genes located on chromosome 19 in a 2 Mb window around rs429358 was established from the GRCh38.p5 *Homo sapiens* Genome Assembly of EnsEmbl (Table 3). This list was then compared with a list of NRF1 target genes as determined from a published ChIP-Seq-Based data retrieved from ChIP-Seq experiments performed in SK-N-SH human neuroblastoma cells for the ENCODE project (encodeprojec-t.org, DDBJ Sequence Read Archive, accession number of SRP007993), and involving chromatin immunoprecipitation with a monoclonal anti-NRF1 antibody followed by deep sequencing at a 36 bp read length on Genome Analyzer[lvi]. By this analysis, F-box protein FBXO46 was identified to be among the genes controlled by NRF1 and to be located in the vicinity of APOE. FBXO46 is situated on 19q13.32, 0.8 Mb downstream from APOE. Other genes located in the vicinity of the APOE4 motif and controlled by NRF1 comprise SNRPD2, ZNF285, ZNF180, PVR, ERCC2, QPCTL, SYMPK, MYPOP, CCDC61, XRCC1, ZNF576, ZNF428, SMG9, PPP5C, PNMA8A/PNMAL1, PNMA8B/PNMAL2, DACT3, STRN4 and FKRP.

NRF1 Binding Sites were Also Detected in the 5' DNA Regions of RTN2, IRGQ, SRRM5, FOXA3, FOSB/deltaFOSB, SIX5 and GPR4:

Functional transcription factor binding sites are likely to be observed between 100 bp downstream from the transcription start site and about 200 bp upstream, but can sometimes be found further away. We subjected the 5' DNA regions of genes RTN2, IRGQ, SRRM5, FOXA3, FOSB (deltaFOSB, a splice variant of FOSB), SIX5 and GPR4 encompassing −1000 bp+400 bp with respect to the transcription start site to a JASPAR 2016 database (http://jaspar2016.genereg.net/) search of NRF1 binding motifs. Genomic regions chr19: 45496661-45408061 (RTN2), chr19:43595735-43597135 (IRGQ) and chr19:43596017-43597017 (SRRM5), chr19: 45862989:45874397 (FOXA3), chr19:45466995-45468395 (FOSB/deltaFOSB), chr19:45768826-45770226 (SIX5) and chr19:45589164:45601808 (GPR4) respectively, were scanned using a stringent relative profile score threshold of 90% (all coordinates are from genome assembly GRCh38.p10). One NRF1 binding site with a score 11.490 was identified in the 5' region of RTN2, five NRF1 binding sites with scores ranging from 14.489 to 18,058 were identified in the 5' DNA region of IRGQ, five NRF1 binding sites with scores ranging from 14.489 to 18.058 were identified in the 5' DNA region of SRRM5, three NRF1 binding sites with scores ranging from 10.857 to 17.077 were identified in the 5' DNA region of FOXA3, eight NRF1 binding sites with scores ranging from 10.228 to 18.058 were identified in the 5' DNA region of FOSB/deltaFOSB, three NRF1 binding sites with scores ranging from 14.200 to 18.058 were identified in the 5' DNA region of SIX5, and one NRF1 binding site with a score of 9.693 was identified in the 5' region of GPR4 (Table 5) The highest score to be expected for the NRF1 consensus sequence in JASPAR is 18.058. We concluded that genes RTN2, IRGQ, SRRM5, FOXA3. FOSB/deltaFOSB, SIX5 and GPR4 are controlled by the transcription factor NRF1.

TABLE 5

JASPAR Analysis of the 5' DNA Regions of RTN2, IRGQ, SRRM5, FOXA3, FOSB/deltaFOSB, SIX5 and GPR4.

| Model ID | Model name | Score | Relative score | Gene | Strand | Predicted site sequence |
|---|---|---|---|---|---|---|
| MA0506.1 | NRF1 | 11.490 | 0.92 | RTN2 | forward | GCGCTTGCCCG (SEQ ID NO: 2) |
| MA0506.1 | NRF1 | 15.197 | 0.96 | IRGQ | reverse | ACGCATGCGCA (SEQ ID NO: 3) |
| MA0506.1 | NRF1 | 17.551 | 0.99 | IRGQ | reverse | GCGCCTGCGCG (SEQ ID NO: 4) |
| MA0506.1 | NRF1 | 14.489 | 0.96 | IRGQ | forward | GCGCAGGCGCG (SEQ ID NO: 5) |
| MA0506.1 | NRF1 | 18.058 | 1.00 | IRGQ | reverse | GCGCCTGCGCA (SEQ ID NO: 6) |
| MA0506.1 | NRF1 | 14.489 | 0.96 | IRGQ | forward | GCGCAGGCGCG (SEQ ID NO: 7) |
| MA0506.1 | NRF1 | 14.489 | 0.96 | SRRM5 | reverse | GCGCAGGCGCG (SEQ ID NO: 8) |
| MA0506.1 | NRF1 | 18.058 | 1.00 | SRRM5 | forward | GCGCCTGCGCA (SEQ ID NO: 9) |
| MA0506.1 | NRF1 | 14.489 | 0.96 | SRRM5 | reverse | GCGCAGGCGCG (SEQ ID NO: 10) |
| MA0506.1 | NRF1 | 17.551 | 0.99 | SRRM5 | forward | GCGCCTGCGCG (SEQ ID NO: 11) |
| MA0506.1 | NRF1 | 15.197 | 0.96 | SRRM5 | forward | ACGCATGCGCA (SEQ ID NO: 12) |
| MA0506.1 | NRF1 | 17.077 | 0.99 | FOXA3 | reverse | GCGCGTGCGCA (SEQ ID NO: 13) |
| MA0506.1 | NRF1 | 13.157 | 0.94 | FOXA3 | forward | GCGCACGCGCC (SEQ ID NO: 14) |
| MA0506.1 | NRF1 | 10.857 | 0.91 | FOXA3 | reverse | GCGCCCGCCCG (SEQ ID NO: 15) |
| MA0506.1 | NRF1 | 18.058 | 1.00 | FOSB | reverse | GCGCCTGCGCA (SEQ ID NO: 16) |
| MA0506.1 | NRF1 | 14.489 | 0.96 | FOSB | forward | GCGCAGGCGCG (SEQ ID NO: 17) |
| MA0506.1 | NRF1 | 10.228 | 0.90 | FOSB | reverse | CCGCCCGCGCC (SEQ ID NO: 18) |
| MA0506.1 | NRF1 | 13.453 | 0.94 | FOSB | reverse | GCGCCCGCGCC (SEQ ID NO: 19) |
| MA0506.1 | NRF1 | 13.803 | 0.95 | FOSB | forward | GCGCGGGCGCG (SEQ ID NO: 20) |
| MA0506.1 | NRF1 | 10.372 | 0.91 | FOSB | forward | GCGGGCGCGCG (SEQ ID NO: 21) |
| MA0506.1 | NRF1 | 12.472 | 0.93 | FOSB | reverse | GCGCGCGCGCC (SEQ ID NO: 22) |
| MA0506.1 | NRF1 | 13.427 | 0.94 | FOSB | forward | GCGCGCGCGCG (SEQ ID NO: 23) |

TABLE 5-continued

JASPAR Analysis of the 5' DNA Regions of
RTN2, IRGQ, SRRM5, FOXA3, FOSB/deltaFOSB, SIX5 and GPR4.

| Model ID | Model name | Score | Relative score | Gene | Strand | Predicted site sequence |
|---|---|---|---|---|---|---|
| MA0506.1 | NRF1 | 14.995 | 0.96 | SIX5 | reverse | GCGCAGGCGCA (SEQ ID NO: 24) |
| MA0506.1 | NRF1 | 18.058 | 1.00 | SIX5 | forward | GCGCCTGCGCA (SEQ ID NO: 25) |
| MA0506.1 | NRF1 | 14.200 | 0.95 | SIX5 | reverse | GCGGATGCGCG (SEQ ID NO: 26) |
| MA0506.1 | NRF1 | 9.693 | 0.90 | GPR4 | reverse | GCGGATGCCCC (SEQ ID NO: 27) |

As can be clearly seen, the APOE4 variant creates a de novo binding site for NRF1. In response to environmental signals including but not limited to herpes reactivation, head injury or metabolic stress, it is believed NRF1 is activated in AD neurons. By binding to APOE4 and the proximal promoter region of one of the genes harboring NRF1 binding sites this transcription factor leads to inappropriate (increase or decrease) expression of AD causing genes. Thus, some aspects of the invention provide a method of treating AD by inhibiting the expression of AD causing genes.

Figure 8B:
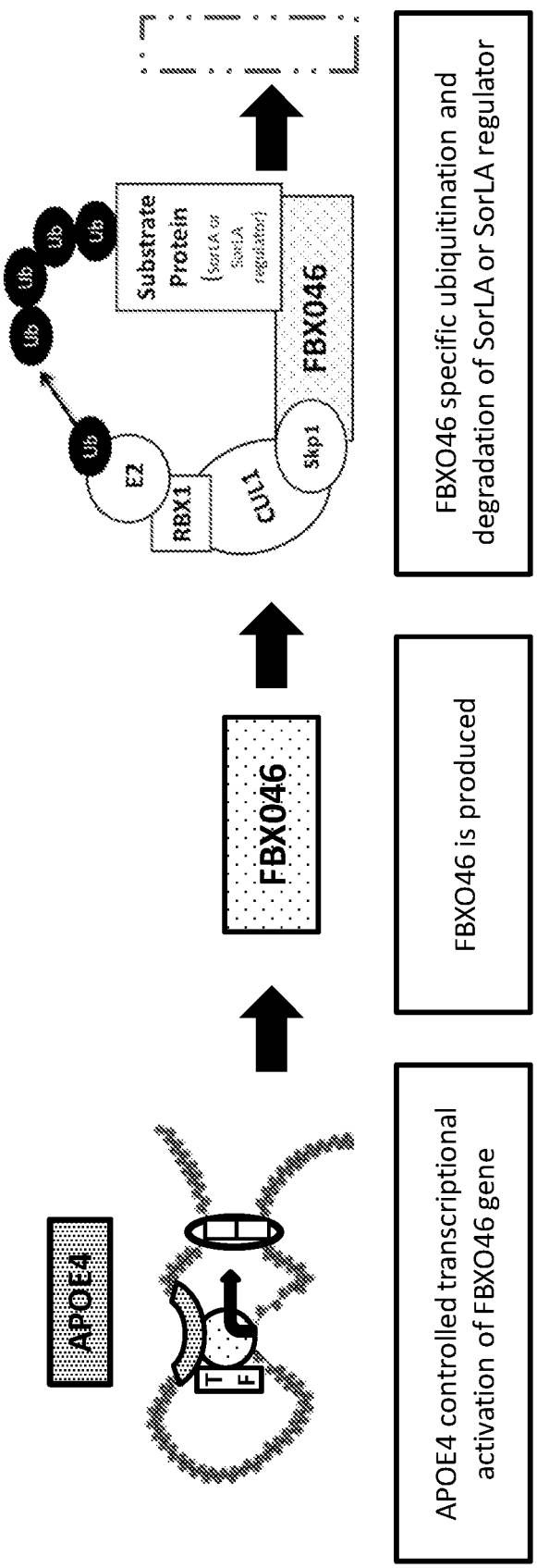

FBXO46 Interference with Amyloidogenic Pathway:

SorLA levels are decreased both in AD patients and in people with mild cognitive impairment. FBXO46 has been shown to interact with key members of the ubiquitination/neddylation pathway[lxxx, lxxxi], SKP1, NEDD8, and COPS5, indicating its role in protein ubiquitination and proteosomal degradation (FIG. 8a). The APOE4 motif-mediated expression of FBXO46 reduces levels of SorLA. Furthermore, the APOE4 motif-mediated expression of FBXO46 leads to the degradation and ensuing low expression of SorLA (FIG. 8b). Moreover, FBXO46 directly binds and ubiquitinates SorLA causing its extraction from the membrane and premature degradation by the proteasome or the lysosome. In addition, FBXO46 degrades or binds SorLA's transcription factor and leads to decreased transcription of SorLA. It is believed that FBXO46 causes the premature degradation of SorLA by binding to a SorLA binding protein.

Figure 8C:
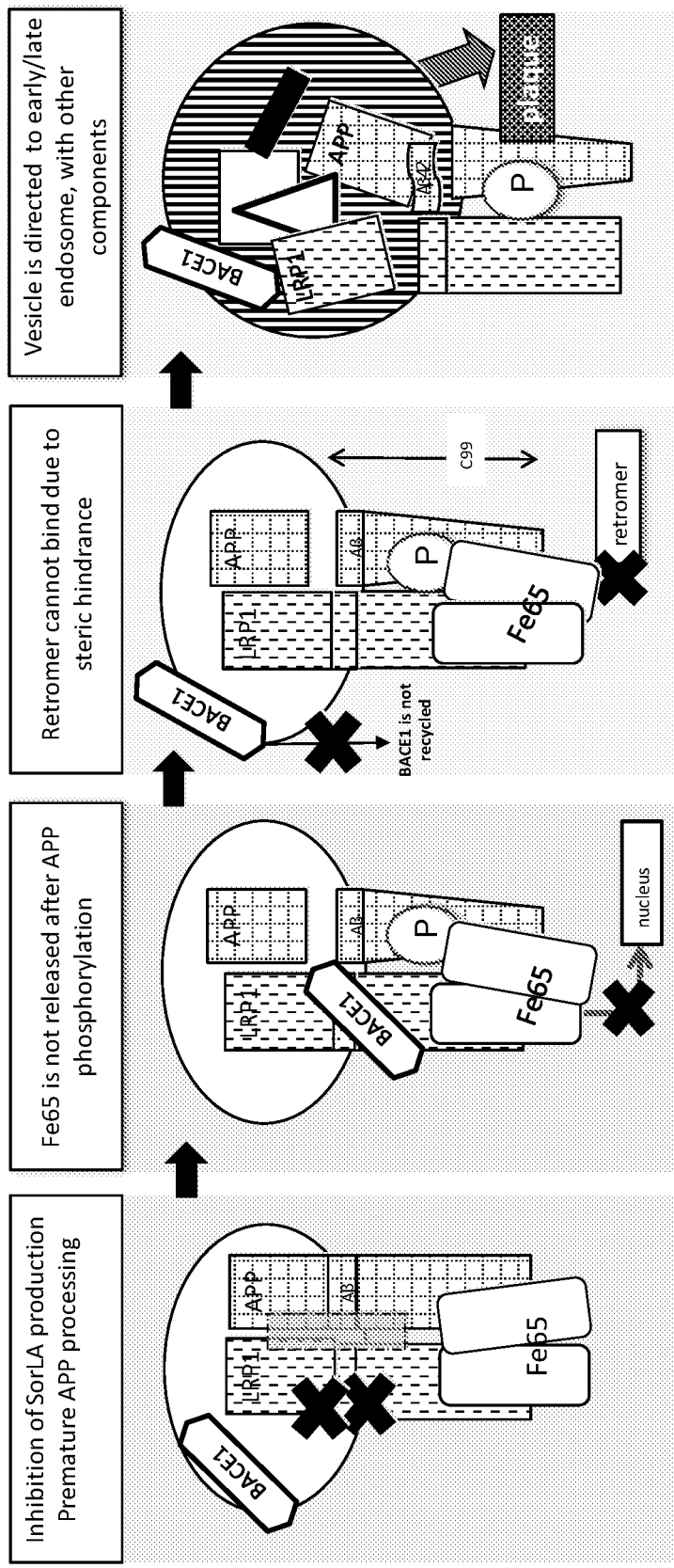

In AD patients, APOE4 motif-mediated expression of FBXO46, thereby reducing levels of SorLA protein (FIG. 8c). Without being bound by any theory, it is believed that APP-BACE1 processing occurs prematurely, to the detriment of LRP1 processing. γ-secretase is unable to process uncleaved LRP1. The LRP1 cytoplasmic domain remains associated with the Fe65/APP complex, and Fe65 cannot be released after APP phosphorylation. Retromer and GGA protein cannot bind due to steric hindrance. As a result, pAPP is not trafficked to the TGN. The endocytic vesicle is directed to the early/late endosome, and intermixes with other cell components. Insoluble Aβ42 is produced and the content of vesicles is expelled as plaque.

Figure 9:
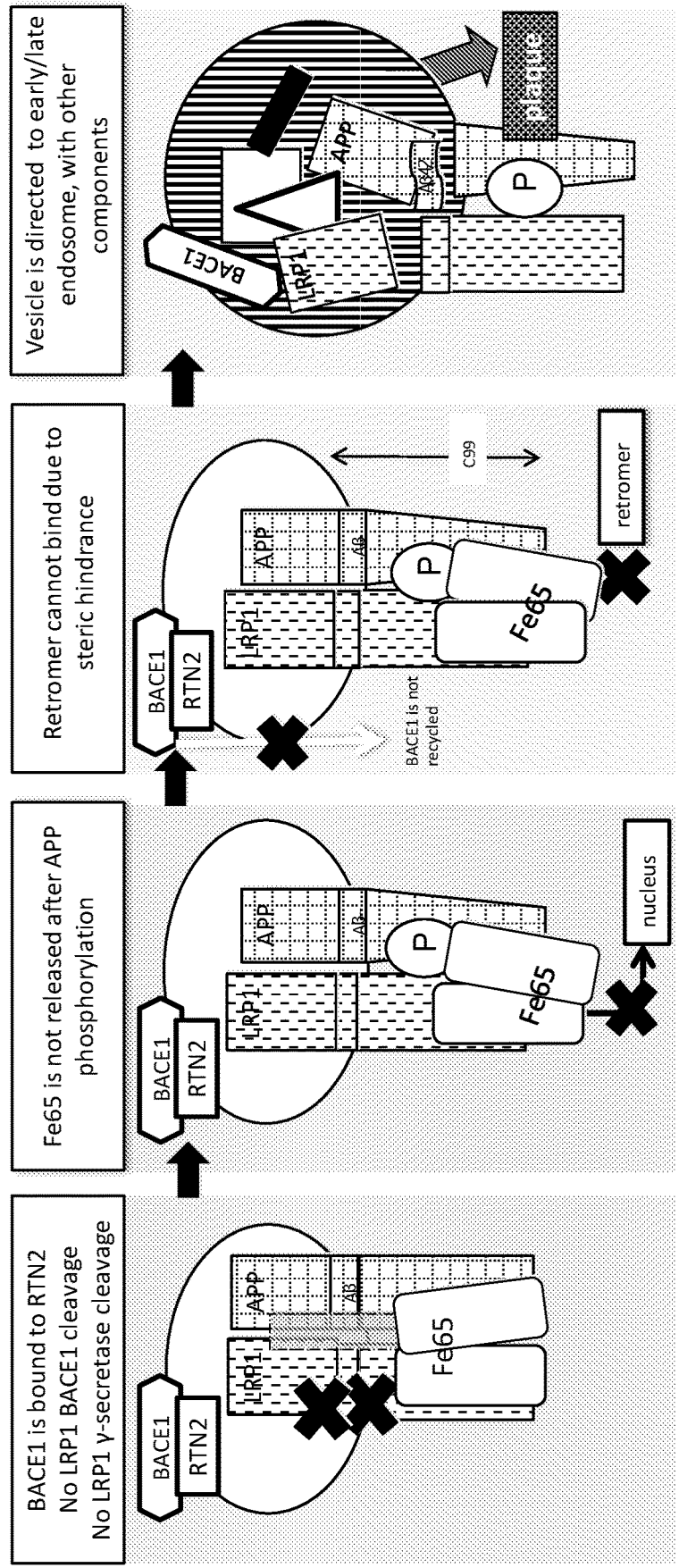
FIG. 9 is a schematic illustration of the effect of Reticulon-2 misexpression on the amyloidogenic pathway.

RTN2 Interference with Amyloidogenic Pathway:

The cytogenic location of RTN2 is at 19q13.32, about 0.58 Mb qter on the reverse strand from APOE, and thus in the range of the APOE4 motif. The APOE4 motif enhances expression of RTN2 (FIG. 9). RTN2 binds to BACE1 retaining more BACE1 in the endoplasmic reticulum compartment, and keeping it from accumulating in lipid rafts at the plasma membrane. APP-BACE1 processing occurs prematurely—when the endocytosed APP complex subsequently merges with a BACE-1-positive recycling endosome. γ-secretase is unable to process uncleaved LRP1 and the LRP1 cytoplasmic domain remains associated with the Fe65/APP complex, and Fe65 cannot be released after APP phosphorylation. The retromer and GGA protein cannot bind due to steric hindrance. As a result, phosphorylated APP is not trafficked to the TGN. The endocytic vesicle is directed to the early/late endosome, and intermixes with other cell components. Insoluble Aβ42 is produced and the content of vesicles is expelled as plaque.

KLC3 Interference with Amyloidogenic Pathway:

The KLC3 (kinesin light chain 3) gene is located on chromosome 19q13.32, downstream of APOE. KLC3 is normally expressed in several tissues, including testis and brain. Under specific environmental or cellular triggers KLC3 is expressed in AD neurons through the transcriptional enhancer activity of the APOE4 motif. Transport of the APP-Fe65-LRP1 vesicle depends on motor protein dynein-, as does retromer transport of APP to the TGN. Kinesin-1 is also required for correct association of dynein on APP vesicles. Improper expression of KLC3 in AD neurons disrupts proper coordination between anterograde and retrograde transport of APP vesicles by shifting the balance towards anterograde transport. In AD patients, APOE motif-mediated expressed KLC3 binds to the heavy chain of kinesin-1, and/or to APP keeping the endocytosed complex from being properly transported to, and from the plasma membrane and other cellular compartments. The key players involved in the amyloidogenic pathway are not recruited in timely fashion. APP-BACE1 processing occurs prematurely. Moreover, transport to the perinuclear space and APP back-trafficking back to the TGN do not take place. The endocytic vesicle remains inside the dendrite and matures into a late endosome. Insoluble Aβ42 is produced and the content of vesicles is expelled as plaque.

Determination of Expression Levels in Cells of Proteins Encoded by the AD Causing Gene:

Human induced pluripotent stem cells (iPSC) derived from a subject with AD and with a known genotype at the rs429358 locus are cultivated and differentiated into neurons. There are numerous protocols available to the one skilled in the art to perform cultivation of iPSC and achieve differentiation into neurons, for example cortical neurons. Cells are typically received in cryovials, cells are then thawed and seeded in an appropriate culture vessel at a density of approximately 50,000 cells/cm$^2$. Cells are then grown in the presence of a neuronal differentiation medium for three days and cultivated for a further several weeks in the presence of a neuronal maintenance medium. Cells are typically assessed 35 days after differentiation for neuronal and synaptic marker expression. Neuronal markers are typically Tuj1 and MAP2, while synaptic markers are PSD-95 (postsynaptic terminals) and synaptophysin (presynaptic terminals). Cell cultures containing one, several or all of these neuronal and synaptic markers can be analyzed as such or further subjected to stress. While there are many procedures to induce cellular stress available to the skilled artisan, osmotic stress is induced by replacing the culture medium of the differentiated neurons with medium containing sorbitol, at a concentration of for example 0.1 to 2.0 M, for 15 to 180 minutes. NRF1 expression and binding to the APOE4 motif can also be achieved by infecting the neuronal cell culture with herpes simplex virus. A further procedure to stress the differentiated neurons is to replace the culture medium of the differentiated neurons with medium lacking glucose for 15 to 180 minutes. After incubation of the differentiated neurons under these described stress conditions, the medium is removed. Some of the cultures are kept in the original culture medium (negative control) and are not exposed to stress conditions. All the neuronal cultures are then rinsed with an appropriate buffer, for example phosphate-buffered saline, and lysed. The lysate is then analyzed for presence of the expressed protein encoded by the AD causing gene using one of the numerous methods available to the one skilled in the art. Cell lysates are prepared and mixed with an appropriate loading buffer. The levels of specific proteins in the lysate are determined by a combination of sodium dodecyl sulfate polyacrylamide gel electrophoresis (SDS-PAGE) of the lysates with a specific detection method (Western blot) using antibodies directed to the proteins to be analyzed. The levels of FBXO46, PPP5C, FKRP, SYMPK, FOSB/deltaFOSB, FOXA3, GPR4, PSG1, PPP1R13L, EXOC3L2, SIX5, PLAUR, KLC3 or any of the genes listed in Table 3 in neurons with an E4 genotype at rs429358 are compared to levels in neurons with an E3 genotype at rs429358 (negative control). Further, the levels of FBXO46, PPP5C, FKRP, SYMPK, FOSB/deltaFOSB, FOXA3, GPR4, PSG1, PPP1R13L, EXOC3L2, SIX5, PLAUR, KLC3 or any of the genes listed in Table 3 in neurons exposed to stress can be compared to levels in neurons that were not exposed to stress (negative control). The expression levels of the AD causing gene are also determined by quantification of messenger RNA (mRNA) levels and compared in cells carrying the E4 genotype versus the E3 genotype. Further the effect of stress conditions can be measured by comparison to the mRNA levels in neurons that were not exposed to stress.

In order to assess the activity of a compound on inhibition of stress-induced expression in differentiated neurons the same cell culture and stress conditions are employed. However, in this case the cell culture is incubated for 1 to 48 hours prior to stress induction with a pharmaceutical composition. The pharmaceutical composition can contain a compound, an oligonucleotide or a derivative thereof, a siRNA or derivative thereof, a protein or a peptide.

It is readily apparent to one skilled in the art that this described method is not limited to neuronal cultures but can be applied to a neuronal cell line, neuronal progenitor cells, cells collected from a patient with AD or cells derived from cells collected from a human subject. It is readily apparent that this assay can be performed using blood, plasma, serum or isolated blood cells collected from human subjects, and can be used to diagnose AD.

Determination of the Activity of AD Causing Genes in Cellular Assay:

Differentiated neurons derived from human iPSC, neuronal progenitor cells, cells of a neuronal cell line such as PC12 or SH-SY5Y are maintained in culture. Cells are transfected with a viral delivery system, using an adeno-associated or semliki-forest like virus, pBROAD, lentivirus, HSV vector or other transfection vehicles carrying a DNA sequence encoding the FBXO46, RTN2, KLC3 or any of the genes listed in Table 3 gene.

After transient expression of the AD causing gene or establishment of stable expression of the AD causing gene, levels of SorLA are determined in the lysate of cultured cells by a combination of sodium dodecyl sulfate polyacrylamide gel electrophoresis (SDS-PAGE) of the lysates with a specific detection method using antibodies directed to SorLA, using Western blots.

The activity of a pharmaceutical composition on inhibition of the AD causing gene activity is measured by the levels of SorLA in cultured cells expressing the AD causing gene. The cell culture is incubated for 1 to 48 hours with the pharmaceutical composition. The pharmaceutical composition can contain a compound, an oligonucleotide or a derivative thereof, a protein or a peptide. The levels of SorLA in presence or absence of the pharmaceutical composition are compared.

It is readily apparent to one skilled in the art that this described method is not limited to neuronal cultures but can be applied to a neuronal cell line, neuronal progenitor cells, cells collected from a patient with AD or cells derived from cells collected from a human subject. It is readily apparent that this assay can be performed using blood, plasma, serum or isolated blood cells collected from human subjects and can be used to diagnose AD.

A method for measuring inhibition of binding of a transcription factor to the APOE4 motif in the presence of a test molecule can comprise a biochemical assay. A biochemical assay is substantially devoid of whole cells but may contain cell extracts or other cellular components, comprises of a recombinant or chemically synthesized transcription factor, a recombinant or chemically synthesized oligonucleotide, and a detection method to measure the binding of the transcription factor to the oligonucleotide. There are numerous methods available to the ones skilled in the art to measure the binding of a transcription factor to an oligonucleotide.

The transcription factor can be immobilized on a solid support and the oligonucleotide is brought into contact with the transcription factor in a reaction chamber. The binding of the oligonucleotide is quantified in an appropriate instrument using techniques known to one skilled in the art. In a preferred embodiment, the binding is quantified by surface plasmon resonance technology. Alternatively, the oligonucleotide is immobilized to the solid support and the transcription factor is brought into proximity in an appropriate reaction chamber. The transcription factor can be a recombinantly expressed NRF1 or a fragment thereof. The oligonucleotide comprises the APOE4 motif. In one embodiment, the oligonucleotide is the exon 4 of the APOE gene or a fragment thereof. In a preferred embodiment the oligonucleotide is 11 to 30 nucleotides in length comprising 11 to 30 consecutive nucleotides within SEQ ID NO: 1.

The biochemical assay comprises an electrophoretic mobility shift assay (EMSA). An APOE4 motif containing oligonucleotide, labeled with a radioactive, fluorescent or biotin label is incubated with a transcription factor to allow complex formation. In one embodiment, the transcription factor is recombinantly expressed NRF1 or a fragment thereof. In another embodiment, the transcription factor is chemically synthesized NRF1 or a fragment thereof. In another embodiment, NRF1 is contained in a nuclear extract of a cell. In one embodiment the oligonucleotide is 11 to 30 nucleotides in length comprising 11 to 24 consecutive nucleotides within SEQ ID NO: 1. The reaction mixture is then analyzed by gel electrophoresis. If NRF1 or a fragment thereof is bound to the APOE4 motif oligonucleotide it shifts the observed mobility of the labeled oligonucleotide towards an apparent higher molecular weight.

In the alternative to a decoy oligonucleotide which inhibits activity of the NRF1 transcription factor, the invention also includes oligonucleotides targeting any transcript of an APOE4 motif-mediated gene. Such oligonucleotide may comprise an oligonucleotide of 11 to 30 nucleotides in length which binds to the transcription product of an APOE4 motif-mediated gene. It may be a single-strand oligonucleotide or a double-strand oligonucleotide. For use as a therapeutic agent, such oligonucleotide may further comprise a pharmaceutically acceptable carrier. Optionally it may be chemically modified or formulated to enable transport into the brain across the blood-brain barrier. Preferred modifications include a phosphorothioate oligonucleotide, a methylphosphonate oligonucleotide, a phosphoamidite oligonucleotide, a peptide nucleic acid oligonucleotide, a locked-nucleic acid-modified oligonucleotide, and combinations thereof. The invention includes methods for inhibiting expression of an APOE4 motif-mediated gene in a cell, said method comprising contacting a cell with an oligonucleotide disclosed herein.

In another embodiment, the oligonucleotide is a short-interfering RNA (siRNA). There are several methods for preparing siRNA, such as chemical synthesis, in vitro transcription, siRNA expression vectors, and PCR expression cassettes. Irrespective of which method one uses, the first step in designing a siRNA requires choosing the siRNA target site. Standard guidelines for choosing siRNA target sites available in the current literature. Using standard guidelines, approximately half of all siRNAs yield >50% reduction in target mRNA levels, thus providing compounds potentially useful in the treatment of AD, and of great interest for further investigation and secondary screening.

Antibodies and Antigen Binding Fragments Thereof:

The term "antibody" as used to herein can include whole antibodies and refers, in one embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. In certain naturally occurring IgG, IgD, and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens.

Antibodies can also include, by way of example, both naturally occurring and non-naturally occurring antibodies; monoclonal and polyclonal antibodies; chimeric and humanized antibodies; fully-human antibodies and many variations known in the art.

The phrase "selectively binds to" refers to the ability of an antibody, antigen binding fragment or binding partner (antigen binding peptide) to preferentially bind to APOE4 motif-mediated gene expression product. Often the phrase "selectively binds" refers to the specific binding of antibody, fragment thereof, or binding partner to an antigen. The level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

Isolated antibodies of the invention can include serum containing such antibodies, or antibodies that have been purified to varying degrees. Whole antibodies of the invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), can also be employed in the invention.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies can be produced according to the methodology of Kohler and Milstein (*Nature*, 1975, 256, 495-497). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

The term "antigen-binding fragment" of an antibody, as used herein, refers to one or more fragments of an antibody that retain the ability to selectively bind to an antigen (e.g., the expression product of an APOE4 motif-mediated gene). It has been shown that the antigen-binding function of an antibody can be performed by fragments of a full-length antibody. Examples of binding fragments encompassed within the term "antigen-binding fragment" of an antibody, e.g., an antibody directed to the expression product of an APOE4 motif-mediated gene, include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These and other potential constructs are described at Chan & Carter (2010) Nat. Rev. Immunol. 10:301. Those skilled in the art are also familiar with antigen-binding fragments such as minibodies, cys-diabodies and fibronectin binding domains, which are also included in the invention herein. These antigen binding fragments are obtained using conventional techniques known to those with skill in the art, and the fragments are screened for utility in the same manner as are intact antibodies. Antigen-binding fragments can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas, or by linking of antigen-binding fragments. See, e.g., Songsivilai & Lachmann, Clin. Exp. Immunol. 79:315-321 (1990); Kostelny et al., J. Immunol. 148, 1547-1553 (1992). The invention includes a bispecific antibody for use in the treatment of AD when one or both of the binding sites are specific for the expression product of an APOE4 motif-mediated gene. Based on the invention disclosed herein, an attractive avenue for therapeutic antibodies and antigen-binding fragments thereof include modifications to enhance transport from the blood to the brain across the blood-brain barrier (BBB).

Antibodies have demonstrated the capacity to cross the blood-brain barrier ("BBB") on their own, often in cases of BBB defects (Prins and Scheltens (2013) Alzheimer's Research & Therapy 5:56; Doody et al. N Engl J Med 370:4). Antibody fragments able to do so have been isolated by phenotypic panning of a naive llama single-domain antibody phage display library. Single domain antibodies, also referred to as nanobodies, are derived from camelids, which make a unique subset of immunoglobulins consisting of heavy chain homodimers devoid of light chains. Their variable region (VHH) is the smallest antigen-binding single polypeptide chain naturally found in the antibody world. Selected antibodies FC5 and FC44 demonstrated significantly ($p<0.01$) enhanced transport (50-100-fold) across the BBB in a rat in vitro model compared to control VHHs.

An alternative to enhance BBB transport is to employ linker molecules that transport antibodies/fragments from the blood into the brain. For example, specific brain delivery is achieved by engineering bispecific antibodies in which a therapeutic "arm" is combined with a BBB-transcytosing arm. Such work is based on recognized BBB specific receptors and transporters. Many endogenous molecules in circulation are able to cross the BBB via specific receptors and transporters expressed on the luminal side of brain endothelial cells, a process known as receptor-mediated transcytosis. Antibodies generated against these receptors, e.g. transferrin receptor (TFRC), insulin receptor (INSR), low density lipoprotein receptor-related protein 1 (LRP1), Basigin (Ok Blood Group, BSG), Glucose Transporter Type 1 (SLC2A1) and solute carrier CD98hc (SLC3A2) have been shown to accumulate in the brain in vivo. These antibodies can be used as platform to deliver therapeutic antibodies across the BBB (Bispecific antibodies in which one half targets the transport system, and the other half is the therapeutic antibody). Bispecific antibodies against the transferrin receptor and BACE1 have been shown to traverse the blood-brain barrier and effectively reduce brain amyloid β levels.

The single-domain antibody FC5 has been shown to engage an active RMT process by binding a putative α(2,3)-sialoglycoprotein receptor. Use of FC5 as the BBB-carrier arm in bispecific antibodies or antibody-drug conjugates offers an avenue to develop pharmacologically active biotherapeutics for CNS indications.

Another BBB transport moiety is the heavy-chain only antibodies identified in sharks. Antigen binding is mediated by a small and highly stable domain, known as VNAR. Antigen-specific VNAR molecules have been generated against a multitude of different targets via immunization, for instance VNAR that target the BBB transferrin receptor, as demonstrated by Ossianix Inc (Philadelphia, Pa.). This VNAR can be incorporated into a bispecific antibody, wherein the other binding moiety targets the expression product of an APOE4 motif-mediated gene.

Diagnosis and Prognosis of AD Using APOE4 Motif-Mediated Genes:

Another aspect of the present invention provides diagnostic assays for measuring levels of an APOE4 motif-mediated gene, or its protein activity, in the context of a biological sample (e.g., blood, urine, biopsies, lymph, saliva, cerebral spinal fluid) to thereby contribute to diagnosis of AD or mild cognitive disorder.

Tissues, cells or body fluids from subjects are collected and analyzed for expression levels of the AD causing gene or for expression levels of any of the genes listed in Table 3. There are numerous methods known to the skilled artisan to measure protein or mRNA expression levels in tissues, cells or body fluids. In a preferred embodiment, the tissue collected from subjects for expression analysis includes whole blood. In another preferred embodiment, fluids collected from subjects for expression analysis include blood plasma, blood serum, sputum, saliva or cerebrospinal fluid. In yet another preferred embodiment, cells collected from subjects include blood cells, buccal cells or skin fibroblasts.

An exemplary method for detecting the presence or absence of an APOE4 motif-mediated protein or nucleic acid in a biological sample involves obtaining a biological sample from a test subject and contacting the biological sample with a compound or an agent capable of detecting the protein or a nucleic acid (e.g., mRNA) that encodes the protein such that the presence of the protein or nucleic acid is detected in the biological sample. A preferred agent for detecting mRNA is a labeled nucleic acid probe capable of hybridizing to the mRNA. The nucleic acid probe can be, for example, a nucleic acid or a corresponding nucleic acid for an APOE4 motif-mediated gene such as an oligonucleotide of at least 15, 30, 50, 100, 250 or 500 nucleotides in length which is capable of specifically hybridizing under stringent conditions to the mRNA. Other suitable probes for use in the diagnostic assays of the invention are known to those skilled in the art.

A preferred agent for detecting protein expression is an antibody capable of binding to a protein expressed from an APOE4 motif-mediated gene, preferably an antibody with a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise antibodies against an appropriate immunogen of an APOE4 motif-mediated gene protein expression product using no more than routine experimentation. Conditions for using such antibodies in a diagnostic assay include incubating an antibody with a test sample under conditions that vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ an antibody of the invention. Examples of such assays can be found in Chard, "An Introduction to Radioimmunoassay and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," is Elsevier Science Publishers, Amsterdam, The Netherlands (1985).

The diagnostic methods of the invention can be used to detect mRNA or protein of an APOE4 motif-mediated gene in a biological sample in vitro as well as in vivo. For example, in vitro techniques for detection of mRNA include northern blot hybridizations and in situ hybridizations. In vitro techniques for detection of proteins include enzyme linked immunosorbent assays (ELISAs), Western blots, immunoprecipitations, immunofluorescence, or quantitative sequencing reactions. Protein or mRNA levels can also be measured in an assay designed to evaluate a panel of target genes, e.g., a microarray or multiplex sequencing reaction.

The invention also provides kits for detecting the presence of an APOE4 motif-mediated gene transcript or its protein expression product in a biological sample. For example, the kit can comprise a labeled compound or agent capable of detecting such protein or mRNA in a biological sample; means for determining the amount of such protein or mRNA in the sample; and means for comparing the amount in the sample with a known standard. The compound or agent can be packaged in a suitable container. The kit can further comprise instructions for using the kit.

One of skill in the art would be capable of performing these well-established protocols for the methods of the invention. (See, for example, Ausubel, et al., "Current Protocols in Molecular Biology," John Wiley & Sons, NY, N.Y. (1999)).

Companion Diagnostic or Selection of Therapeutic Agent:

The diagnostic methods of the invention provide advantages in the selection of an appropriate therapeutic agent for treatment or prevention of AD or mild cognitive disorder. Given that a variety of therapeutic agents are employed in the treatment of symptoms of AD, and new therapeutics are anticipated in coming years, it is now possible to stratify patients who are responders or non-responders to such treatments on the basis of the activity or expression of the APOE4 motif-mediated genes. Those of skill in the art can now perform clinical trials which correlate drug responsiveness with the results of one or more diagnostic assays for APOE4 motif-mediated genes and their protein products.

At least two categories of such tests are immediately apparent. In one, a method for selecting a therapeutic agent for administration to a subject having, or at-risk of having, Alzheimer's disease or mild cognitive impairment, comprises measuring the activity of an APOE4 motif-mediated gene in a biological sample from the subject, and selecting a therapeutic agent based on whether the subject demonstrates elevated activity of said gene in said sample. This example facilitates selection of a therapeutic agent of any type for the patient based on the diagnostic result.

In another method, a therapeutic agent which inhibits activity of an APOE4 motif-mediated gene expression product may be recommended only if the subject demonstrates an elevated level of such gene expression product in the tissue sample. In this case the diagnostic test for an APOE4 motif-mediated gene expression product is commonly known as a companion diagnostic. In such cases, if said subject does not demonstrate elevated levels of gene or protein activity, the treatment is different than if he/she does.

Experimental Validation of APOE4 Motif-Mediated Genes as Diagnostic and Therapeutic Targets in Human Neural Cells Study 1: FBXO46 RNA Expression Levels in AD and Control Neurological Tissue:

In this study, elevated RNA transcript level of FBX046, one of the APOE4 motif-mediated genes, is identified in AD subjects compared to non-AD subjects, thereby validating the potential for FBX046 as a target for diagnosis and therapy of AD.

Relative RNA expression levels of FBXO46 in hippocampal tissues isolated from subjects with or without Alzheimer's disease was determined. The Dataset Browser of GEO (Gene Expression Omnibus), a public functional genomics data repository to search for gene expression profiles in Alzheimer's disease, was used. The GEO Profiles database stores gene expression profiles derived from curated data sets submitted by the research community. The present inventors identified 32 dataset records containing search term ("Alzheimer"), the present inventors selected the study titled: "Postmortem Alzheimer's disease brains: Hisayama study"[lxxxii] as most relevant as it is a comparative microarray analyses of postmortem brain tissues (frontal cortex, temporal cortex, hippocampus) from male and female Hisayama residents pathologically diagnosed as having Alzheimer's disease (AD) or an AD-like disorder (Reference series GSE36980).

Total RNA from the dissected hippocampi of 7 Alzheimer's disease patients (4 females and 3 males), and 10 healthy (non-AD) subjects (5 females and 5 males) were analyzed. All AD patients were diagnosed as Braak stage V-VI. Affymetrix GeneChip Human Gene 1.0 ST arrays ((GPL6244 platform) were used, all experimental steps followed manufacturer's instructions and data analysis was done using manufacturer's software. The obtained dataset, recorded as GDS4758 in GEO profiles, is based on expression data for 33,297 transcript clusters. This dataset was analyzed using the browser DATA analysis tools. Term "FBXO46" was entered in the search window and retrieved the data for each of the 17 tissue samples representing the log 2 transformed relative expression levels of FBXO46. An exponent of 2 (i.e., $2^x$) was applied to this data to yield untransformed expression level information for each of the 17 tissues (Table 6).

The average expression level for the 7 tissues derived from the AD patients and the 10 tissues from the control patients, respectively, was calculated and compared the values using a two-tailed Student t-test. The FBXO46 expression values were for the AD patients 271.6±14.1 (mean±standard deviation) and for the control subjects 254.7±15.6 (mean±standard deviation). This difference was statistically significant with a p-value <0.05. These results indicate that FBXO46 expression is increased in Alzheimer's disease.

TABLE 6

FBXO46 expression levels in Alzheimer's disease and control human hippocampal tissues.

| Sample | log 2 transformed expression level | Untransformed expression level ($2^x$) | Mean | SD* |
|---|---|---|---|---|
| AD hippocampus subject 1 | 7.992 | 254.55 | | |
| AD hippocampus subject 2 | 8.131 | 280.29 | | |
| AD hippocampus subject 3 | 8.005 | 256.87 | | |
| AD hippocampus subject 4 | 8.030 | 261.36 | | |
| AD hippocampus subject 5 | 8.187 | 291.46 | | |
| AD hippocampus subject 6 | 8.103 | 275.04 | | |
| AD hippocampus subject 7 | 8.138 | 281.78 | 271.62 | 14.13 |
| Control* hippocampus subject 1 | 8.068 | 268.41 | | |
| Control hippocampus subject 2 | 7.985 | 253.39 | | |
| Control hippocampus subject 3 | 7.884 | 236.14 | | |
| Control hippocampus subject 4 | 7.933 | 244.32 | | |
| Control hippocampus subject 5 | 8.123 | 278.71 | | |
| Control hippocampus subject 6 | 8.075 | 269.69 | | |
| Control hippocampus subject 7 | 7.834 | 228.25 | | |
| Control hippocampus subject 8 | 8.019 | 259.44 | | |
| Control hippocampus subject 9 | 7.974 | 251.39 | | |
| Control hippocampus subject 10 | 8.010 | 257.74 | 254.75 | 15.58 |

*Control = non-AD
** Standard Deviation

Study 2: PPP5C RNA Expression Levels in AD and Control Neurological Tissue:

In this study, decreased RNA transcript level of PPP5C, one of the APOE4 motif-mediated genes, is identified in AD subjects compared to non-AD subjects, thereby validating the potential for PPP5C as a target for diagnosis and therapy of AD.

Relative expression levels of PPP5C (Protein Phosphatase 5 Catalytic Subunit) were determined in hippocampal tissues isolated from subjects with or without Alzheimer's disease. The study titled: "Postmortem Alzheimer's disease brains: Hisayama study"[lxxxiii] (Reference series GSE36980) from the GEO functional genomics data repository was selected as the most relevant as it is a comparative microarray analyses of postmortem brain tissues (frontal cortex, temporal cortex, hippocampus) from male and female Hisayama residents pathologically diagnosed as having Alzheimer's disease (AD) or an AD-like disorder. The pertaining dataset (GDS4758) for "PPP5C" was searched using the DATA analysis tools browser and retrieved the data for each of the 17 tissue samples representing the log 2 transformed relative expression levels of PPP5C. An exponent of 2 (i.e., 2') was applied to this data to yield untransformed expression level information for each of the 17 tissues (Table 7). The average expression level for the 7 tissues derived from the AD patients and the 10 tissues from the control patients, respectively, were calculated and compared using a two-tailed Student t-test. The PPP5C expression values were for the AD patients 496.01±50.83 (mean±standard deviation) and for the control subjects 574.14±51.28 (mean±standard deviation). This difference was statistically significant with a p-value <0.05. The results indicate that PPP5C expression is decreased in Alzheimer's disease.

TABLE 7

PPP5C expression in Alzheimer's disease and control human hippocampal tissues

| Sample | log 2 transformed expression level | Untransformed expression level ($2^x$) | Mean | SD* |
|---|---|---|---|---|
| AD hippocampus subject 2 | 9.01 | 517.06 | | |

TABLE 7-continued

PPP5C expression in Alzheimer's disease
and control human hippocampal tissues

| Sample | log 2 transformed expression level | Untransformed expression level (2^x) | Mean | SD* |
|---|---|---|---|---|
| AD hippocampus subject 3 | 8.85 | 461.58 | | |
| AD hippocampus subject 4 | 9.07 | 538.48 | | |
| AD hippocampus subject 5 | 9.09 | 545.87 | | |
| AD hippocampus subject 6 | 8.99 | 508.47 | | |
| AD hippocampus subject 7 | 8.66 | 404.58 | 496.01 | 50.83 |
| Control** hippocampus subject 1 | 9.27 | 619.13 | | |
| Control hippocampus subject 2 | 9.24 | 602.68 | | |
| Control hippocampus subject 3 | 9.01 | 515.31 | | |
| Control hippocampus subject 4 | 8.96 | 497.85 | | |
| Control hippocampus subject 5 | 9.12 | 557.68 | | |
| Control hippocampus subject 6 | 9.23 | 601.33 | | |
| Control hippocampus subject 7 | 9.22 | 597.78 | | |
| Control hippocampus subject 8 | 9.35 | 654.11 | | |
| Control hippocampus subject 9 | 9.01 | 514.70 | | |
| Control hippocampus subject 10 | 9.18 | 580.88 | 574.14 | 51.28 |

* Standard Deviation
**Non-AD

Study 3: Fukutin Related Protein and Symplekin Expression Levels in AD and Control Tissues:

In this study, increased RNA transcript levels of Fukutin Related Protein (FKRP) and Symplekin (SYMPK), which are APOE4 motif-mediated genes, are identified in incipient AD subjects compared to non-AD subjects, thereby validating the potential for FKRP and SYMPK as a target for diagnosis and therapy of AD.

Relative expression levels of FKRP and SYMPK were determined in hippocampal tissues from subjects at varying stages of Alzheimer's disease. The Dataset Browser of the GEO functional repository was used to search for gene expression profiles and selected the study titled: "Various stages of Alzheimer's disease: laser-captured hippocampal CA1 gray matter"[lxxxiv] as most relevant. This study is a comparative microarray analysis of hippocampal CA1 gray matter microdissected by laser capture from formalin-fixed, paraffin-embedded hippocampal sections of subjects at varying stages of Alzheimer's disease (Reference series GSE28146). Brain sections from a total of 30 subjects were analyzed. Subjects were separated into four categories of varying AD severity based on Mini Mental Status Exam results (MMSE), Neurofibrillary Tangle (NFT) count and Braak stage. Hence, 8 subjects were classified as control (MMSE: 27.6±0.6; NFT: 3.0±1.1; Braak: 2.3±0.40), 7 subjects were classified as incipient AD (MMSE: 24.3±1.1; NFT: 17.5±8.2; Braak: 5.0±0.5), 8 subjects as moderate AD (MMSE: 16.5±0.6; NFT: 8/25.6±3.5; Braak: 5.5±0.2), and 7 subjects as severe AD (MMSE: 6.0±1.4; NFT: 32.7±3.2; Braak: 5.8±0.2). A Zeiss AxioObserver PALM Microbeam with RoboMover cap system was used to image, cut and capture CA1 gray matter region for each specimen. Total RNA from the dissected regions was then prepared for labeling and microarray hybridization (Affymetrix Human Genome U133 Plus 2.0 Array, GPL570 platform). All experimental steps followed manufacturer's instructions and data analysis was done using manufacturer's software. The obtained dataset, recorded as GDS4136 in GEO profiles, is based on expression data for 12,665 genes.

This dataset was analyzed using the browser DATA analysis tools. The term "FKRP" was entered in the search window and retrieved the data for each of the four tissue sample categories representing the untransformed expression levels of Fukutin Related Protein (Table 8). The average expression level for the 8 tissues derived from the control patients and the 7 tissues from incipient AD patients, respectively, was calculated after removing values below 1/3 of average or above 3 times the average in all groups. The remaining 7 control values and 5 incipient AD values were compared using a two-tailed Student t-test. The FKRP expression values were for the AD patients 455.32±88.39 (mean±standard deviation) and for the control subjects 262.97±72.09 (mean±standard deviation). This difference was statistically significant with a p-value <0.05. The results showed that FKPD expression is increased in Alzheimer's disease.

TABLE 8

FKRP expression in incipient Alzheimer's
disease and control human CA1 gray matter.

| Sample | Untransformed expression level | Mean | Standard deviation |
|---|---|---|---|
| Control (non AD) CA1 subject 1 | 159.1 | | |
| Control (non AD) CA1 subject 2 | 282.5 | | |
| Control (non AD) CA1 subject 4 | 210.7 | | |
| Control (non AD) CA1 subject 5 | 232.2 | | |
| Control (non AD) CA1 subject 6 | 250.9 | | |
| Control (non AD) CA1 subject 7 | 359.2 | | |
| Control (non AD) CA1 subject 8 | 346.2 | 262.97 | 72.09 |
| Incipient AD CA1 subject 1 | 488.2 | | |
| Incipient AD CA1 subject 3 | 471.0 | | |
| Incipient AD CA1 subject 4 | 321.5 | | |
| Incipient AD CA1 subject 5 | 562.7 | | |
| Incipient AD CA1 subject 6 | 433.2 | 455.32 | 88.39 |

The term "SYMPK" was entered in the search window of the browser DATA analysis tools and retrieved the data for each of the four tissue sample categories representing the untransformed expression levels of Symplekin. (Table 9). The average expression level for the 8 tissues derived from the control patients and the 7 tissues from incipient AD patients, respectively, was calculated and removed values below 1/3 of average or above 3 times the average in all groups. The remaining 7 control values and 6 incipient AD values was compared using a two-tailed Student t-test. The SYMPK expression values were for the AD patients 504.73±198.01 (mean±standard deviation) and for the control subjects 253±127.81 (mean±standard deviation). This difference was statistically significant with a p-value <0.05. These results showed that SYMPK expression is increased in Alzheimer's disease.

TABLE 9

SYMPK expression in incipient Alzheimer's disease and control human CA1 gray matter.

| Sample | Untransformed expression level | Mean | Standard deviation |
|---|---|---|---|
| Control (non AD) CA1 subject 1 | 498.3 | | |
| Control (non AD) CA1 subject 2 | 174.9 | | |
| Control (non AD) CA1 subject 3 | 317.2 | | |
| Control (non AD) CA1 subject 5 | 134.2 | | |
| Control (non AD) CA1 subject 6 | 274.4 | | |
| Control (non AD) CA1 subject 7 | 231.1 | | |
| Control (non AD) CA1 subject 8 | 140.9 | 253 | 127.81 |
| Incipient AD CA1 subject 1 | 515.1 | | |
| Incipient AD CA1 subject 3 | 457.6 | | |
| Incipient AD CA1 subject 4 | 353.9 | | |
| Incipient AD CA1 subject 5 | 264.8 | | |
| Incipient AD CA1 subject 6 | 823.4 | | |
| Incipient AD CA1 subject 7 | 613.6 | 504.73 | 198.01 |

Study 4: Differential Gene Expression of Isogenic Human Neurons with APOE4/E4, APOE3/E3 and APOE2/E2 Genotypes Using qPCR Methods:

Quantitative real-time reverse-transcription polymerase chain reaction (qPCR) analysis was performed to evaluate the expression profile of genes located within 2 Mb of rs429358 (APOE4) on chromosome 19.

PCR (Polymerase Chain Reaction) is a common laboratory method known to one skilled in the art where a specific part of a template DNA is replicated in cycles of repeated heating and cooling, thus permitting an exponential amplification of the target sequences. PCR relies on a thermostable DNA polymerase, and requires primers, short fragments of single-stranded DNA that bind to the template by complementary base pairing. Primers are design so they flank the DNA region to be amplified. While in standard PCR the amplified DNA product is detected in an end-point analysis, in qPCR (quantitative PCR or real-time PCR) the accumulation of amplification products is measured as the reaction progresses after each cycle. Detection of PCR products is enabled by the use of a fluorescent reporter molecule in the reaction that yields increased fluorescence with an increasing amount of product DNA. We employed a method of detection that involves the double-stranded DNA intercalating molecule SYBR Green® to determine gene expression levels of protein encoding genes located within 2 Mb of rs429358 (APOE4) on chromosome 19. We employed a method that uses dual-labeled probes, also known as TaqMan® probes to measure expression levels of miRNAs located within 2 Mb of rs429358 (APOE4) on chromosome 19. A dual-labeled probe consists of a 18-22 bp single-stranded oligonucleotide that is labeled with a reporter dye at the 5' end and a quencher moiety at the 3' end. This type of fluorogenic probe is designed to anneal specifically to an internal region of the target sequence between the forward and reverse primer. Amplification of the target gene causes displacement and cleavage of the probe by the 5' nuclease activity of Taq DNA polymerase, generating an increase in reporter fluorescence as the PCR primer is extended. Both of these methods are commonly used for quantification of gene expression levels and are known to a skilled artisan.

Quantitative PCR (qPCR) was performed to determine transcript levels of a subset of the APOE4 motif-mediated genes in commercially available human neurons differentiated from induced pluripotent stem cells (IPSC) (Cellular Dynamics Inc., Wisconsin, USA). Human IPCS are derived from somatic cells that have been reprogrammed to pluripotency by application of a set of transcription factors[lxxxv]. One original neuron line was modified by CRISPR to carry either the APOE4/E4, APOE3/E3 or APOE2/E2 genotype, respectively, thereby minimizing any other genetic variation between the cell lines. Hence, each of these neurons is homozygous for the E4, E3 or E2 allele, respectively. Neurons analyzed are thus designated E3E3, E4E4 and E2E2 for homozygous genotypes E3/E3, E4/E4 and E2/E2, respectively. These neurons are a mixture of post-mitotic neural subtypes, but comprise primarily of GABAergic, inhibitory neurons, with typical physiological characteristics and responses.

Total RNA was extracted from $4.0 \times 10^6$ E3E3 neurons, $4.9 \times 10^6$ E4E4 neurons and $4.4 \times 10^6$ E2E2 neurons by methods known to the skilled artisan. Initial assessment of RNA purity and concentration was performed by NanoDrop spectrophotometer analysis and RNA integrity was determined by using the Agilent 2100 Bioanalyzer. The yields for total RNA were 9.6 micrograms, 5.8 micrograms and 8.4 micrograms for the E3E3, E4E4 and E2E2 neurons, respectively. Complementary DNA was synthesized using proven, consistent and reliable reagents from established manufacturers known to the skilled artisan. qPCR experiments were run in the 7900 HT fast real-time PCR system from Thermo Fisher Scientific using SYBR Green-based assays for the detection of messenger RNAs and TaqMan probes for the detection of micro RNAs. Each experiment encompassed three independent amplification assays of the genetic material isolated from each independent pellet.

Results:

Quantification of nucleic acids was achieved using relative quantification analysis (Double delta Ct data analysis). Relative quantification allows to determine fold-differences in expression of the target gene in the disease cell line relative to the control cell lines. First a baseline was subtracted from the raw data based on the raw fluorescence values. Next, the threshold cycle (Ct) value was determined for each sample, which represents the number of cycles needed to reach a particular quantification threshold fluorescence signal level. Ct values were determined both for the genes being evaluated and for reference genes for normalization purposes. Four genes, Glyceraldehyde-3-Phosphate Dehydrogenase (GAPDH), ubiquitin conjugating enzyme E2 D2 (UBE2D2), cytochrome c1 (CYC1) and ribosomal protein L13 (RPL13) were used as reference genes in the SYBR® Green-based assays and MIR103, MIR106b, MIR26b and MIR191 were used as references in the TaqMan® microRNAs expression assays. Average Ct values were determined for a gene of interest and the reference genes (designated as "Ref") in the E4E4 IPSC-derived neurons and each of the control cell lines (E3E3 and E2E2 IPSC-derived neurons, respectively). For further data analysis the E4E4 samples were compared to either the E3E3 or the E2E2 samples. For each paired comparison the following four values were generated: Avg. Ct Ref in E4E4, Avg. Ct Ref in E3E3 (or E2E2), Avg. Ct gene of interest in E4E4, and Avg. Ct gene of interest in E3E3 (or E2E2). The differences between Ct values of the gene of interest and reference genes (delta Ct values, short dCt) were calculated for the E4E4 and the control. Next, the difference between E4E4 and control was calculated to arrive at the Double Delta Ct Value (ddCt E4E4-E3E3 or ddCt E4E4-E2E2). Since the quantity of amplified product doubles in each cycle, the expression fold change between E4E4 and control (Relative Quantification or RQ (E4E4/E3E3 or E4E4/E2E2)

was computed with the following formula $2^{-ddCt}$. P values to assess statistical significance of observed differences were calculated by a two-tailed t test using dCt values of each sample set as the data. Protein encoding genes which are significantly different in IPSC-derived neurons with the homozygous E4E4 genotype compared to the E3E3 or E2E2 neurons are listed in Table 10. A negative value in the fold change column indicates that the gene is downregulated in E4E4 neurons, while a positive value indicates that the gene is upregulated. MIR320E was elevated in E4E4 neurons (1.37-fold) relative to E3E3 neurons. MIR320E was elevated in E4E4 neurons (1.54-fold) relative to E2E2 neurons.

TABLE 10

Genes exhibiting significant differential expression in IPSC-derived neurons with the homozygous E4E4 genotype compared to E3E3 and E2E2 neurons, respectively.

| Gene | E4E4 vs E3E3 | | E4E4 vs E2E2 | |
| --- | --- | --- | --- | --- |
| | Fold Change (Test/Control) | p value | Fold Change (Test/Control) | p value |
| deltaFOSB | −6.254 | 0.0016556 | −7.492 | 0.0008517 |
| FOXA3 | −5.604 | 0.0000212 | −5.261 | 0.0000187 |
| GPR4 | −5.427 | 0.0002294 | −5.705 | 0.0001269 |
| PSG1 | −4.201 | 0.0004173 | −3.774 | 0.0002849 |
| PPP1R13L | −2.339 | 0.0000247 | −1.682 | 0.0012937 |
| EXOC3L2 | −2.243 | 0.0003368 | −2.202 | 0.0010158 |
| ZNF285 | −1.889 | 0.0029322 | −1.512 | 0.0172506 |
| SIX5 | −1.754 | 0.0038547 | −9.791 | 0.0000017 |
| PLAUR | −1.730 | 0.0105537 | −2.521 | 0.0002754 |
| VASP | −1.689 | 0.0009335 | −1.290 | 0.0019558 |
| EML2 | −1.331 | 0.0048007 | −1.386 | 0.0031142 |
| OPA3 | −1.287 | 0.0132998 | −1.239 | 0.0112741 |
| BCAM | −1.266 | 0.0011660 | −1.762 | 0.0003897 |
| QPCTL | −1.246 | 0.0396793 | −1.378 | 0.0066485 |
| STRN4 | 1.127 | 0.0031971 | 1.315 | 0.0009115 |
| SYMPK | 1.269 | 0.0037928 | 1.180 | 0.0133916 |
| KLC3 | 4.092 | 0.0000493 | 4.419 | 0.0005891 |

These results show strikingly that the presence of the APOE4 motif in E4E4 neurons mediates significant changes in expression levels of genes in the vicinity of rs429358 (APOE4) on chromosome 19 compared to isogenic neurons that are either homozygous for the E3 or homozygous for the E2 genotype, respectively. Further, the presence of the APOE4 motif can decrease the expression level (FOSB splice variant deltaFOSB, FOXA, GPR4, PSG1, PPP1R13L, EXOC3L2, ZNF285, SIX5, PLAUR, VASP, EML2, OPA3, BCAM, QPCTL) or increase the expression level (KLC3, SYMPK, STRN4) of a target gene.

Together the examples herein provide experimental validation of APOE4 motif-mediated genes and expression products thereof as targets for diagnosis, prevention and treatment of Alzheimer's disease and mild cognitive impairment.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

CITED REFERENCES

[i] Shelton S B, Johnson G V. Cyclin-dependent kinase-5 in neurodegeneration. J. Neurochem. 2004 March; 88(6): 1313-26.

[ii] Zekanowski C, Wojda U. Aneuploidy, chromosomal missegregation, and cell cycle reentry in Alzheimer's disease. Acta Neurobiol Exp (Wars). 2009; 69(2):232-53.

[iii] Zivković L, Spremo-Potparević B, Plecas-Solarović B, Djelić N, Ocić G, Smiljković P, Siedlak S L, Smith M A, Bajić V. J Premature centromere division of metaphase chromosomes in peripheral blood lymphocytes of Alzheimer's disease patients: relation to gender and age. Gerontol A Biol Sci Med Sci. 2010 December; 65(12): 1269-74. doi: 10.1093/gerona/glq148. Epub 2010 Aug. 30.

[iv] Trippi F, Botto N, Scarpato R, Petrozzi L, Bonuccelli U, Latorraca S, Sorbi S, Migliore L. Spontaneous and induced chromosome damage in somatic cells of sporadic and familial Alzheimer's disease patients. Mutagenesis. 2001 July; 16(4):323-7.

[v] Moreira P I, Santos R X, Zhu X, Lee H G, Smith M A, Casadesus G, Perry G. Autophagy in Alzheimer's disease. Expert Rev Neurother. 2010 July; 10(7):1209-18.

[vi] Stieber A, Mourelatos Z, Gonatas N K. In Alzheimer's disease the Golgi apparatus of a population of neurons without neurofibrillary tangles is fragmented and atrophic. Am J Pathol. 1996 February; 148(2):415-26.

[vii] Carter T L, Rissman R A, Mishizen-Eberz A J, Wolfe B B, Hamilton R L, Gandy S, Armstrong D M. Differential preservation of AMPA receptor subunits in the hippocampi of Alzheimer's disease patients according to Braak stage. Exp Neurol. 2004 June; 187(2):299-309.

[viii] Cataldo A M, Peterhoff C M, Troncoso J C, Gomez-Isla T, Hyman B T, Nixon R A. Endocytic pathway abnormalities precede amyloid beta deposition in sporadic Alzheimer's disease and Down syndrome: differential effects of APOE genotype and presenilin mutations. Am J Pathol. 2000 July; 157(1):277-86.

[ix] Mahley R W1, Rall S C Jr. Apolipoprotein E: far more than a lipid transport protein. Annu Rev Genomics Hum Genet. 2000; 1:507-37.

[x] Farrer L A1, Cupples L A, Haines J L, Hyman B, Kukull W A, Mayeux R, Myers R H, Pericak-Vance M A, Risch N, van Duijn C M. Effects of age, sex, and ethnicity on the association between apolipoprotein E genotype and Alzheimer disease. A meta-analysis. APOE and Alzheimer Disease Meta Analysis Consortium. JAMA. 1997 Oct. 22-29; 278(16):1349-56.

[xi] Raber J, Huang Y, Ashford J W. ApoE genotype accounts for the vast majority of AD risk and AD pathology. Neurobiol Aging. 2004 May-June; 25(5):641-50.

[xii] Genin E, Hannequin D, Wallon D, Sleegers K, Hiltunen M, Combarros O, Bullido M J, Engelborghs S, De Deyn P, Ben C, Pasquier F, Dubois B, Tognoni G, Fiévet N, Brouwers N, Bettens K, Arosio B, Coto E, Del Zompo M, Mateo I, Epelbaum J, Frank-Garcia A, Helisalmi S, Porcellini E, Pilotto A, Forti P, Ferri R, Scarpini E, Siciliano G, Solfrizzi V, Sorbi S, Spalletta G, Valdivieso F, Vepsalainen S, Alvarez V, Bosco P, Mancuso M, Panza F, Nacmias B, Bossù P, Hanon O, Piccardi P, Annoni G, Seripa D, Galimberti D, Licastro F, Soininen H, Dartigues J F, Kamboh M I, Van Broeckhoven C, Lambert J C, Amouyel P, Campion D. APOE and Alzheimer disease: a major gene with semi-dominant inheritance. Mol Psychiatry. 2011 September; 16(9):903-7. doi: 10.1038/mp.2011.52. Epub 2011 May 10.

[xiii] Morgen K, Frölich L, Tost H, Plichta M M, Kölsch H, Rakebrandt F, Rienhoff O, Jessen F, Peters O, Jahn H, Luckhaus C, Hüll M, Gertz H J, Schröder J, Hampel H, Teipel S J, Pantel J, Heuser I, Wiltfang J, Rüther E, Kornhuber J, Maier W, Meyer-Lindenberg A. APOE-dependent phenotypes in subjects with mild cognitive impairment converting to Alzheimer's disease. J Alzheimers Dis. 2013; 37(2):389-401. doi: 10.3233/JAD-130326.

[xiv] Xu W L, Caracciolo B, Wang H X, Santoni G, Winblad B, Fratiglioni L. Accelerated progression from mild cognitive impairment to dementia among APOE ε4ε4 carriers. J Alzheimers Dis. 2013; 33(2):507-15. doi: 10.3233/JAD-2012-121369.

[xv] Davies G, Harris S E, Reynolds C A, Payton A, Knight H M, Liewald D C, Lopez L M, Luciano M, Gow A J, Corley J, Henderson R, Murray C, Pattie A, Fox H C, Redmond P, Lutz M W, Chiba-Falek O, Linnertz C9, Saith S, Haggarty P1, McNeill G, Ke X1, Ollier W, Horan M, Roses A D, Ponting C P, Porteous D J, Tenesa A, Pickles A, Starr J M, Whalley L, Pedersen N L, Pendleton N, Visscher P M, Deary I J. A genome-wide association study implicates the APOE locus in nonpathological cognitive ageing. Mol Psychiatry. 2014 January; 19(1):76-87. doi: 10.1038/mp.2012.159. Epub 2012 Dec. 4.

[xvi] Yu C E, Cudaback E, Foraker J, Thomson Z, Leong L, Lutz F, Gill J A, Saxton A, Kraemer B, Navas P, Keene C D, Montine T, Bekris L M. Epigenetic signature and enhancer activity of the human APOE gene. Hum Mol Genet. 2013 Dec. 15; 22(24):5036-47. doi: 10.1093/hmg/ddt354. Epub 2013 Jul. 25.

[xvii] Chen H P, Lin A, Bloom J S, Khan A H, Park C C, Smith D J. Screening reveals conserved and nonconserved transcriptional regulatory elements including an E3/E4 allele-dependent APOE coding region enhancer. Genomics. 2008 November; 92(5):292-300. doi: 10.1016/j.ygeno.2008.07.009. Epub 2008 Sep. 3.

[xviii] Lambert J C, Ibrahim-Verbaas C A, Harold D, Naj A C, Sims R, Bellenguez C, DeStafano A L, Bis J C, Beecham G W, Grenier-Boley B, Russo G, Thorton-Wells T A, Jones N, Smith A V, Chouraki V, Thomas C, Ikram M A, Zelenika D, Vardarajan B N, Kamatani Y, Lin C F, Gerrish A, Schmidt H, Kunkle B, Dunstan M L, Ruiz A, Bihoreau M T, Choi S H, Reitz C, Pasquier F, Cruchaga C, Craig D, Amin N, Berr C, Lopez O L, De Jager P L, Deramecourt V, Johnston J A, Evans D, Lovestone S, Letenneur L, Morón F J, Rubinsztein D C, Eiriksdottir G, Sleegers K, Goate A M, Fiévet N, Huentelman M W, Gill M, Brown K, Kamboh M I, Keller L, Barberger-Gateau P, McGuiness B, Larson E B, Green R, Myers A J, Dufouil C, Todd S, Wallon D, Love S, Rogaeva E, Gallacher J, St George-Hyslop P, Clarimon J, Lleo A, Bayer A, Tsuang D W, Yu L, Tsolaki M, Bossù P, Spalletta G, Proitsi P, Collinge J, Sorbi S, Sanchez-Garcia F, Fox N C, Hardy J, Deniz Naranjo M C, Bosco P, Clarke R, Brayne C, Galimberti D, Mancuso M, Matthews F; European Alzheimer's Disease Initiative (EADI); Genetic and Environmental Risk in Alzheimer's Disease; Alzheimer's Disease Genetic Consortium; Cohorts for Heart and Aging Research in Genomic Epidemiology, Moebus S, Mecocci P, Del Zompo M, Maier W, Hampel H, Pilotto A, Bullido M, Panza F, Caffarra P, Nacmias B, Gilbert J R, Mayhaus M, Lannefelt L, Hakonarson H, Pichler S, Carrasquillo M M, Ingelsson M, Beekly D, Alvarez V, Zou F, Valladares O, Younkin S G, Coto E, Hamilton-Nelson K L, Gu W, Razquin C, Pastor P, Mateo I, Owen M J, Faber K M, Jonsson P V, Combarros O, O'Donovan M C, Cantwell L B, Soininen H, Blacker D, Mead S, Mosley T H Jr, Bennett D A, Harris T B, Fratiglioni L, Holmes C, de Bruijn R F, Passmore P, Montine T J, Bettens K, Rotter J I, Brice A, Morgan K, Foroud T_M, Kukull W A, Hannequin D, Powell J F, Nalls M A, Ritchie K, Lunetta K L, Kauwe J S, Boerwinkle E, Riemenschneider M, Boada M, Hiltuenen M, Martin E R, Schmidt R, Rujescu D, Wang L S, Dartigues J F, Mayeux R, Tzourio C, Holman A, Nöthen M M, Graff C, Psaty B M, Jones L, Haines J L, Holmans P A, Lathrop M, Pericak-Vance M A, Launer L J, Farrer L A, van Duijn C M, Van Broeckhoven C, Moskvina V, Seshadri S, Williams J, Schellenberg G D, Amouyel P. Meta-analysis of 74,046 individuals identifies 11 new susceptibility loci for Alzheimer's disease. Nat Genet. 2013 December; 45(12):1452-8. doi: 10.1038/ng.2802. Epub 2013 Oct. 27.

[xix] Zhang S, Zhang M, Cai F, Song W. Biological function of Presenilin and its role in AD pathogenesis. Transl Neurodegener. 2013 Jul. 17; 2(1):15. doi: 10.1186/2047-9158-2-15.

[xx] Nelson O, Supnet C, Liu H, Bezprozvanny I. Familial Alzheimer's Disease mutations in presenilins: effects on endoplasmic reticulum calcium homeostasis and correlation with clinical phenotypes. J Alzheimers Dis. 2010; 21(3):781-93.

[xxi] Zheng H, Koo E H. The amyloid precursor protein: beyond amyloid. Mol Neurodegener. 2006 Jul. 3; 1:5.

[xxii] Cupers P, Orlans I, Craessaerts K, Annaert W, De Strooper B. The amyloid precursor protein (app)-cytoplasmic fragment generated by γ-secretase is rapidly degraded but distributes partially in a nuclear fraction of neurones in culture. J Neurochem. 2001 September; 78(5):1168-78.

[xxiii] Thinakaran G, Koo E H. Amyloid precursor protein trafficking, processing, and function. J Biol Chem. 2008 Oct. 31; 283(44):29615-9. Epub 2008 Jul. 23. Review.

[xxiv] Choy R W, Cheng Z, Schekman R. Amyloid precursor protein (APP) traffics from the cell surface via endosomes for amyloid β (Aβ) production in the trans-Golgi network. Proc Natl Acad Sci USA. 2012 Jul. 24; 109(30):E2077-82. Epub 2012 Jun. 18.

[xxv] Das U, Scott D A, Ganguly A, Koo E H, Tang Y, Roy S. Activity-induced convergence of APP and BACE-1 in acidic microdomains via an endocytosis-dependent pathway. Neuron. 2013 Aug. 7; 79(3):447-60. doi: 10.1016/j.neuron.2013.05.035.

[xxvi] Radzimanowski J, Simon B, Sattler M, Beyreuther K, Sinning I, Wild K. Structure of the intracellular domain of the amyloid precursor protein in complex with Fe65-PTB2. EMBO Rep. 2008 November; 9(11):1134-40. Epub 2008 Oct. 3.

[xxvii] Guenette S, Chang Y, Hiesberger T, Richardson J A, Eckman C B, Eckman E A, Hammer R E, Herz J. Essential roles for the FE65 amyloid precursor protein-interacting proteins in brain development. EMBO J. 2006; 25: 420-431 xxvi

[xxviii] Cao X, Südhof T C. Dissection of amyloid-β precursor protein-dependent transcriptional activation. J Biol Chem 2004 279:24601-11.

[xxix] Bertram L, Parkinson M, McQueen M B, Mullin K, Hsiao M, Menon R, Moscarillo T J, Blacker D, Tanzi R E. Further evidence for LBP-1c/CP2/LSF association in Alzheimer's Disease families. J Med Genet. 2005 November; 42(11):857-62.

xxx Lin W H, Nebhan C A, Anderson B R, Webb D J. Vasodilator-stimulated phosphoprotein (VASP) induces actin assembly in dendritic spines to promote their development and potentiate synaptic strength. J Biol Chem. 2010 Nov. 12; 285(46):36010-20. doi: 10.1074/jbc.M110.129841. Epub 2010 Sep. 8.

xxxi Fuentealba R A, Liu Q, Kanekiyo T, Zhang J, Bu G. Low density lipoprotein receptor-related protein 1 promotes anti-apoptotic signaling in neurons by activating Akt survival pathway. J Biol Chem. 2009 Dec. 4; 284(49): 34045-53. Epub 2009 Oct. 8.

xxxii Bu G. Apolipoprotein E and its receptors in Alzheimer's Disease: pathways, pathogenesis and therapy. Nature Reviews Neuroscience 2009 May; 10:333-344.

xxxiii Arélin K, Kinoshita A, Whelan C M, Irizarry M C, Rebeck G W, Strickland D K, Hyman B T. LRP and senile plaques in Alzheimer's disease: colocalization with apolipoprotein E and with activated astrocytes. Brain Res Mol Brain Res. 2002 Jul. 15; 104(1):38-46.

xxxiv Ulery P G, Beers J, Mikhailenko I, Tanzi R E, Rebeck G W, Hyman B T, Strickland D K. Modulation of beta-amyloid precursor protein processing by the low density lipoprotein receptor related (LRP). Evidence that LRP contributes to the pathogenesis of Alzheimer's Disease. J Biol Chem. 2000 Mar. 10; 275(10):7410-5.

xxxv Mulvihill M M, Guttman M, Komives E A. Protein Interactions among Fe65, the Low-Density Lipoprotein Receptor-Related Protein, and the Amyloid Precursor Protein. Biochemistry, 2011 Jul. 19; 50(28):6208-16. Epub 2011 Jun. 24.

xxxvi Colombo A, Bastone A, Ploia C, Sclip A, Salmona M, Forloni G, Borsello T. JNK regulates APP cleavage and degradation in a model of Alzheimer's disease. Neurobiol Dis. 2009 March; 33(3):518-25. doi: 10.1016/j.nbd.2008.12.014. Epub 2009 Jan. 8.

xxxvii Mazzitelli S, Xu P, Ferrer I, Davis R J, Tournier C. The loss of c-Jun N-terminal protein kinase activity prevents the amyloidogenic cleavage of amyloid precursor protein and the formation of amyloid plaques in vivo. J Neurosci. 2011 Nov. 23; 31(47):16969-76. doi: 10.1523/JNEUROSCI.4491-11.2011.

xxxviii Suzuki T, Nakaya T. Regulation of amyloid beta-protein precursor by phosphorylation and protein interactions. J Biol Chem. 2008 Oct. 31; 283(44):29633-7. doi: 10.1074/jbc.R800003200. Epub 2008 Jul. 23.

xxxix Lee M S, Kao S C, Lemere C A, Xia W, Tseng H C, Zhou Y, Neve R, Ahlijanian M K, Tsai L H. APP processing is regulated by cytoplasmic phosphorylation. J Cell Biol. 2003 Oct. 13; 163(1):83-95.

xl Vardarajan B N, Bruesegem S Y, Harbour M E, Inzelberg R, Friedland R, St George-Hyslop P, Seaman M N, Farrer L A. Identification of Alzheimer disease-associated variants in genes that regulate retromer function. Neurobiol Aging. 2012 September; 33(9): 2231.e15-2231.e30. doi: 10.1016/j.neurobiolaging. 2012.04.020. Epub 2012 Jun. 5.

xli Willnow T E, Carlo A S, Rohe M, Schmidt V. SORLA/SORL1, a neuronal sorting receptor implicated in Alzheimer's disease. Rev Neurosci. 2010; 21(4):315-29.

xlii Fjorback A W, Andersen O M. SorLA is a molecular link for retromer-dependent sorting of the Amyloid precursor protein. Commun Integr Biol. 2012 Nov. 1; 5(6):616-9. doi: 10.4161/cib.21433.

xliii Sullivan CP1, Jay A G, Stack E C, Pakaluk M, Wadlinger E, Fine R E, Wells J M, Morin P J. Retromer disruption promotes amyloidogenic APP processing. Neurobiol Dis. 2011 August; 43(2):338-45. doi: 10.1016/j.nbd.2011.04.002. Epub 2011 Apr. 16.

xliv Scherzer, C. R., Offe, K., Gearing, M. Rees, H. D. Fang, G. Heilman, C. J. Schaller, C. Bujo, H. Levey, A. I., Lah, J. J. Loss of apolipoprotein E receptor LR11 in Alzheimer disease. Arch. Neurol. 61: 1200-1205, 2004. Note: Erratum: Arch. Neurol. 64: 557 only, 2007.

xlv Ma, Q. L., Galasko, D. R., Ringman, J. M., Vinters, H. V., Edland, S. D., Pomakian, J., Ubeda, O. J., Rosario, E. R., Teter, B., Frautschy, S. A. et al. (2009). Reduction of SorLA/LR11, a sorting protein limiting beta-amyloid production, in Alzheimer disease cerebrospinal fluid. Arch. Neurol. 66, 448-457.

xlvi Dodson S E, Gearing M, Lippa C F, Montine T J, Levey A I, Lah J J. LR11/SorLA expression is reduced in sporadic Alzheimer disease but not in familial Alzheimer disease. J Neuropathol Exp Neurol. 2006 September; 65(9):866-72.

xlvii Sager K L, Wuu J, Leurgans S E, Rees H D, Gearing M, Mufson E J, Levey A I, Lah J J. Neuronal LR11/sorLA expression is reduced in mild cognitive impairment. Ann Neurol. 2007 December; 62(6):640-7.

xlviii Thakurta I G and Andersen O. Associations of sorLA/SORL1 with Alzheimer's disease. Receptors & Clinical Investigation 2015; 2: e700. doi: 10.14800/rci.700.

xlix Andersen O M1, Schmidt V, Spoelgen R, Gliemann J, Behlke J, Galatis D, McKinstry W J, Parker M W, Masters C L, Hyman B T, Cappai R, Willnow T E. Molecular dissection of the interaction between amyloid precursor protein and its neuronal trafficking receptor SorLA/LR11. Biochemistry. 2006 Feb. 28; 45(8):2618-28.

l Schmidt V, Baum K, Lao A, Rateitschak K, Schmitz Y, Teichmann A, Wiesner B, Petersen C M, Nykjaer A, Wolf J, Wolkenhauer O, Willnow T E. Quantitative modelling of amyloidogenic processing and its influence by SORLA in Alzheimer's disease. EMBO J. 2012 Jan. 4; 31(1):187-200. doi: 10.1038/emboj.2011.352. Epub 2011 Oct. 11.

li Spoelgen R, von Arnim C A, Thomas A V, Peltan I D, Koker M, Deng A, Irizarry M C, Andersen O M, Willnow T E, Hyman B T. Interaction of the cytosolic domains of sorLA/LR11 with the amyloid precursor protein (APP) and beta-secretase beta-site APP-cleaving enzyme. J Neurosci. 2006 Jan. 11; 26(2):418-28.

lii Herskowitz J H, Seyfried N T, Gearing M, Kahn R A, Peng J, Levey A I, Lah J J. Rho kinase II phosphorylation of the lipoprotein receptor LR11/SORLA alters amyloid-beta production. J Biol Chem. 2011 Feb. 25; 286(8):6117-27. doi: 10.1074/jbc.M110.167239. Epub 2010 Dec. 8.

liii Kelly D P, Scarpulla R C. Transcriptional regulatory circuits controlling mitochondrial biogenesis and function. Genes Dev. 2004 Feb. 15; 18(4):357-68.

liv Johar K, Priya A, Wong-Riley M T. Regulation of Na(+)/K(+)-ATPase by nuclear respiratory factor 1: implication in the tight coupling of neuronal activity, energy generation, and energy consumption. J Biol Chem. 2012 Nov. 23; 287(48):40381-90. doi: 10.1074/jbc.M112.414573. Epub 2012 Oct. 9.

lv Tong C W1, Wang J L, Jiang M S, Hsu C H, Chang W T, Huang A M. Gene. 2013 Feb. 15; 515(1):62-70. doi: 10.1016/j.gene.2012.11.026. Epub 2012 Dec. 7. Novel genes that mediate nuclear respiratory factor 1-regulated neurite outgrowth in neuroblastoma IMR-32 cells.

lvi Satoh J, Kawana N, Yamamoto Y. Pathway Analysis of ChIP-Seq-Based NRF1 Target Genes Suggests a Logical

[lvii] Chandrasekaran S, Bonchev D. Network Topology Analysis of Post-Mortem Brain Microarrays Identifies More Alzheimer's Related Genes and MicroRNAs and Points to Novel Routes for Fighting with the Disease. PLoS One. 2016 Jan. 19; 11(1):e0144052.

Hypothesis of their Involvement in the Pathogenesis of Neurodegenerative Diseases. Gene Regul Syst Bio. 2013 Nov. 4; 7:139-52. doi: 10.4137/GRSB.S13204. eCollection 2013.

[lviii] Yang Y S, Strittmatter S M. The reticulons: a family of proteins with diverse functions. Genome Biol. 2007; 8(12):234. doi: 10.1186/gb-2007-8-12-234.

[lix] Montenegro G, Rebelo A P, Connell J, Allison R, Babalini C, D'Aloia M, Montieri P, Schüle R, Ishiura H, Price J, Strickland A, Gonzalez M A, Baumbach-Reardon L, Deconinck T, Huang J, Bernardi G, Vance J M, Rogers M T, Tsuji S, De Jonghe P, Pericak-Vance M A, Schöls L, Orlacchio A, Reid E, Züchner S. Mutations in the ER-shaping protein reticulon 2 cause the axon-degenerative disorder hereditary spastic paraplegia type 12. J Clin Invest. 2012 February; 122(2):538-44. doi: 10.1172/JCI60560. Epub 2012 Jan. 9.

[lx] He W, Lu Y, Qahwash I, Hu X Y, Chang A, Yan R. Reticulon family members modulate BACE1 activity and amyloid-beta peptide generation. Nat Med. 2004; 10:959-965. doi: 10.1038/nm1088.

[lxi] Murayama K S, Kametani F, Saito S, Kume H, Akiyama H, Araki W. Reticulons RTN3 and RTN4-B/C interact with BACE1 and inhibit its ability to produce amyloid beta-protein. Eur J Neurosci. 2006 September; 24(5): 1237-44. Epub 2006 Sep. 8.

[lxii] Araki W, Oda A, Motoki K, Hattori K, Itoh M, Yuasa S, Konishi Y, Shin R W, Tamaoka A, Ogino K. Reduction of β-amyloid accumulation by reticulon 3 in transgenic mice. Curr Alzheimer Res. 2013 February; 10(2):135-42.

[lxiii] Hu X, Shi Q, Zhou X, He W, Yi H, Yin X, et al. Transgenic mice overexpressing reticulon 3 develop neuritic abnormalities. EMBO Journal. 2007; 26(11):2755-2767.

[lxiv] Kamal A, Stokin G B, Yang Z, Xia C H, Goldstein L S. Axonal transport of amyloid precursor protein is mediated by direct binding to the kinesin light chain subunit of kinesin-I. Neuron. 2000 November; 28(2):449-59. Proc Natl Acad Sci USA. 2012 May 29; 109(22):8582-7. doi: 10.1073/pnas.1120510109. Epub 2012 May 11.

[lxv] Szpankowski L, Encalada S E, Goldstein L S. Subpixel colocalization reveals amyloid precursor protein-dependent kinesin-1 and dynein association with axonal vesicles. Proc Natl Acad Sci USA. 2012 May 29; 109 (22):8582-7. doi: 10.1073/pnas.1120510109. Epub 2012 May 11.

[lxvi] Morihara T, Hayashi N, Yokokoji M, Akatsu H, Silverman M A, Kimura N, Sato M, Saito Y, Suzuki T, Yanagida K, Kodama T S, Tanaka T, Okochi M, Tagami S, Kazui H, Kudo T, Hashimoto R, Itoh N, Nishitomi K, Yamaguchi-Kabata Y, Tsunoda T, Takamura H, Katayama T, Kimura R, Kamino K, Hashizume Y, Takeda M. Transcriptome analysis of distinct mouse strains reveals kinesin light chain-1 splicing as an amyloid-β accumulation modifier. Proc Natl Acad Sci USA. 2014 Feb. 18; 111(7):2638-43. doi: 10.1073/pnas.1307345111. Epub 2014 Feb. 4.

[lxvii] Liu C C, Kanekiyo T, Xu H, Bu G. Apolipoprotein E and Alzheimer disease: risk, mechanisms and therapy. Nat Rev Neurol. 2013 February; 9(2):106-18. doi: 10.1038/nrneurol.2012.263. Epub 2013 Jan. 8. Erratum in: Nat Rev Neurol. 2013. doi: 10.1038/nmeurol.2013.32. Liu, Chia-Chan [corrected to Liu, Chia-Chen].

[lxviii] Theendakara V, Peters-Libeu C A, Spilman P, Poksay K S, Bredesen D E, Rao RV. Direct Transcriptional Effects of Apolipoprotein E. J Neurosci. 2016 Jan. 20; 36(3):685-700.

[lxix] Schirm S, Jiricny J, Schaffner W. The SV40 enhancer can be dissected into multiple segments, each with a different cell type specificity. Genes Dev. 1987 March; 1(1):65-74.

[lxx] Lezza A M, Pesce V, Comio, A, Fracasso F, Vecchiet J, Felzani G, Cantatore P, Gadaleta M N. Increased expression of mitochondrial transcription factor A and nuclear respiratory, factor-1 in skeletal muscle from aged human subjects. FEBS Lett. 2001 Jul. 13; 501(1):74-8.

[lxxi] Peers C, Pearson H A, Boyle J P. Hypoxia and Alzheimer's disease. Essays Biochem. 2007; 43:153-64.

[lxxii] van Tienen F H, Lindsey P J, van der Kallen C J, Smeets H J. Prolonged Nrf1 overexpression triggers adipocyte inflammation and insulin resistance. J Cell Biochem. 2010 Dec. 15; 111(6):1575-85. doi: 10.1002/jcb.22889.

[lxxiii] Tokusumi Y, Zhou S, Takada S. Nuclear respiratory factor 1 plays an essential role in transcriptional initiation from the hepatitis B virus x gene promoter. J Virol. 2004 October; 78(20):10856-64.

[lxxiv] Miele A, Dekker J. Long-range chromosomal interactions and gene regulation. Mol Biosyst. 2008 November; 4(11):1046-57. doi: 10.1039/b803580f. Epub 2008 Aug. 13.

[lxxv] Erceg J, Saunders T E, Girardot C, Devos D P, Hufnagel L, Furlong E E. Subtle changes in motif positioning cause tissue-specific effects on robustness of an enhancer's activity. PLoS Genet. 2014 January; 10(1):e1004060. doi: 10.1371/journal.pgen.1004060. Epub 2014 Jan. 2.

[lxxvi] Guenther C A, Tasic B, Luo L, Bedell M A, Kingsley DM. A molecular basis for classic blond hair color in Europeans. Nat Genet. 2014 July; 46(7):748-52. doi: 10.1038/ng.2991. Epub 2014 Jun. 1.

[lxxvii] http://uswest.ensembl.org/Homo_sapiens/Info/Index

[lxxviii] Galan J M, Peter M. Ubiquitin-dependent degradation of multiple F-box proteins by an autocatalytic mechanism. Proc Natl Acad Sci USA. 1999 Aug. 3; 96(16): 9124-9.

[lxxix] Medway C W, Abdul-Hay S, Mims T, Ma L, Bisceglio G, Zou F, Pankratz S, Sando S B, Aasly J O, Barcikowska M, Siuda J, Wszolek Z K, Ross O A, Carrasquillo M, Dickson D W, Graff-Radford N, Petersen R C, Ertekin-Taner N, Morgan K, Bu G, Younkin S G. ApoE variant p.V236E is associated with markedly reduced risk of Alzheimer's disease. Mol Neurodegener. 2014 Mar. 10; 9:11. doi: 10.1186/1750-1326-9-11.

[lxxx] Lockwood W W, Chandel S K, Stewart G L, Erdjument-Bromage H, Beverly L J. The novel ubiquitin ligase complex, SCF(Fbxw4), interacts with the COP9 signalosome in an F-box dependent manner, is mutated, lost and under-expressed in human cancers. PLoS One. 2013 May 2; 8(5):e63610. doi: 10.1371/journal.pone.0063610. Print 2013.

[lxxxi] Bennett E J1, Rush J, Gygi S P, Harper J W. Dynamics of cullin-RING ubiquitin ligase network revealed by systematic quantitative proteomics. Cell. 2010 Dec. 10; 143(6):951-65. doi: 10.1016/j.cell.2010.11.017.

lxxxii Hokama M, Oka S, Leon J, Ninomiya T, Honda H, Sasaki K, Iwaki T, Ohara T, Sasaki T, LaFerla F M, Kiyohara Y, Nakabeppu Y. Altered expression of diabetes-related genes in Alzheimer's disease brains: the Hisayama study. Cereb Cortex. 2014 September; 24(9):2476-88. doi: 10.1093/cercor/bht101. Epub 2013 Apr. 17 lxxxiii Hokama M, Oka S, Leon J, Ninomiya T, Honda H, Sasaki K, Iwaki T, Ohara T, Sasaki T, LaFerla F M, Kiyohara Y, Nakabeppu Y. Altered expression of diabetes-related genes in Alzheimer's disease brains: the Hisayama study. Cereb Cortex. 2014 September; 24(9):2476-88. doi: 10.1093/cercor/bht101. Epub 2013 Apr. 17

[lxxxiv] Blalock E M, Buechel H M, Popovic J, Geddes J W, Landfield P W. Microarray analyses of laser-captured hippocampus reveal distinct gray and white matter signatures associated with incipient Alzheimer's disease. J Chem Neuroanat. 2011 October; 42(2):118-26. doi: 10.1016/j.jchemneu.2011.06.007. Epub 2011 Jul. 2.

[lxxxv] Takahashi K, Yamanaka S. Induction of pluripotent stem cells from mouse embryonic and adult fibroblast cultures by defined factors. Cell. 2006 Aug. 25; 126(4): 663-76. Epub 2006 Aug. 10.

What is claimed is:

1. A method for detecting a change in the expression of, or an activity of a gene expression product encoded by, an Apolipoprotein E allele ε4 (APOE4) motif-mediated gene located on human chromosome 19 to identify one or more molecules to treat or alleviate symptoms in an individual suffering from Alzheimer's disease or mild cognitive impairment, the method comprising:
measuring the expression of, or the activity of the gene expression product encoded by, an APOE4 motif-mediated gene located on human chromosome 19 in cells having an APOE4 allele,
wherein the APOE4 motif-mediated gene is G-Protein Coupled Receptor 4 (GPR4), and detecting a decrease in the expression or the activity in response to a molecule,
wherein the one or more molecules comprise an oligonucleotide, or a derivative thereof, and
wherein the decrease in the expression or the activity detected comprises a decrease in the synthesis of a gene expression product, a decrease in an activity of the gene expression product, or a decrease in the expression of an mRNA encoded by the APOE4 motif-mediated gene; and
wherein detecting the decrease in the expression or the activity indicates the one or more molecules are directed to treat and/or alleviate Alzheimer's disease or mild cognitive impairment, and wherein the APOE4 allele comprises SEQ ID NO: 1, and wherein the one or more molecules is an oligonucleotide that comprises at least 11 contiguous nucleotides of SEQ ID NO:1 or its complementary sequence.

2. The method of claim 1, wherein the gene expression product is a protein and a level of the protein is determined by a combination of sodium dodecyl sulfate polyacrylamide gel electrophoresis (SDS-PAGE) and a Western blot.

3. The method of claim 1, further comprising a step of assaying a plurality of molecules to identify a core structure shared among the plurality of molecules that show a change in expression of, or the activity of the gene expression product to ascertain potential lead compounds for treatment of Alzheimer's disease or mild cognitive impairment.

4. The method of claim 1, wherein the one or more molecules comprise an oligonucleotide that is between 11 and 30 nucleotides in length, and comprises at least 11 contiguous nucleotides of SEQ ID NO:1.

5. The method of claim 4, wherein the one or more molecules comprise an oligonucleotide that is between 24 and 30 nucleotides in length, and comprises SEQ ID NO:1.

6. A method for detecting a change in the expression of, or an activity of a gene expression product encoded by, an Apolipoprotein E allele ε4 (APOE4) motif-mediated gene located on human chromosome 19 to identify a molecule to treat and/or diagnose an individual suffering from Alzheimer's disease or mild cognitive impairment, the method comprising:
measuring the expression of, or the activity of the gene expression product encoded by, an APOE4 motif-mediated gene located on human chromosome 19 in cells having an APOE4 allele,
wherein the APOE4 motif-mediated gene is G-Protein Coupled Receptor 4 (GPR4), and detecting an increase in the expression or the activity in response to a molecule,
wherein the molecule is an oligonucleotide, or a derivative thereof, and
wherein the increase in the expression or the activity detected comprises an increase in the synthesis of a gene expression product, an increase in an activity of the gene expression product, or an increase in the expression of an mRNA encoded by the APOE4 motif-mediated gene; and
wherein detecting the increase in the expression or the activity indicates the molecule is directed to treat and/or diagnose Alzheimer's disease or mild cognitive impairment and wherein the APOE4 allele comprises SEQ ID NO: 1, and wherein the one or more molecules is an oligonucleotide that comprises at least 11 contiguous nucleotides of SEQ ID NO: 1 or its complementary sequence.

7. The method of claim 6, wherein the increase in expression of, or the activity of a protein encoded by, the APOE4 motif-mediated gene is detected by a change in the amount of secreted Sortilin Related Receptor 1 (SORLA) protein.

8. The method according to claim 6 wherein the cells are human cells.

9. The method according to claim 6 wherein the cells are neuronal cells, neuronal progenitor cells, or differentiated neurons.

10. The method according to claim 6 wherein the method is a cell-based method.

11. The method of claim 6, wherein the molecule comprises an oligonucleotide that is between 11 and 30 nucleotides in length, and comprises at least 11 contiguous nucleotides of SEQ ID NO:1.

* * * * *

```
                       SEQUENCE LISTING

<160> NUMBER OF SEQ ID NOS: 27

<210> SEQ ID NO 1
<211> LENGTH: 24
<212> TYPE: DNA
<213> ORGANISM: Homo sapiens

<400> SEQUENCE: 1
tggaggacgt gcgcggccgc ctgg                                          24

<210> SEQ ID NO 2
<211> LENGTH: 11
<212> TYPE: DNA
<213> ORGANISM: Artificial Sequence
<220> FEATURE:
<223> OTHER INFORMATION: RTN2 - Forward Primer

<400> SEQUENCE: 2
gcgcttgccc g                                                        11

<210> SEQ ID NO 3
<211> LENGTH: 11
<212> TYPE: DNA
<213> ORGANISM: Artificial Sequence
<220> FEATURE:
<223> OTHER INFORMATION: IRGO reverse 01

<400> SEQUENCE: 3
acgcatgcgc a                                                        11

<210> SEQ ID NO 4
<211> LENGTH: 11
<212> TYPE: DNA
<213> ORGANISM: Artificial Sequence
<220> FEATURE:
<223> OTHER INFORMATION: IRGQ reverse 02

<400> SEQUENCE: 4
gcgcctgcgc g                                                        11

<210> SEQ ID NO 5
<211> LENGTH: 11
<212> TYPE: DNA
<213> ORGANISM: Artificial Sequence
<220> FEATURE:
<223> OTHER INFORMATION: IRGQ forward 01

<400> SEQUENCE: 5
gcgcaggcgc g                                                        11

<210> SEQ ID NO 6
<211> LENGTH: 11
<212> TYPE: DNA
<213> ORGANISM: Artificial Sequence
<220> FEATURE:
<223> OTHER INFORMATION: IRGQ reverse 03

<400> SEQUENCE: 6
```
gcgcctgcgc a                                           11

<210> SEQ ID NO 7
<211> LENGTH: 11
<212> TYPE: DNA
<213> ORGANISM: Artificial Sequence
<220> FEATURE:
<223> OTHER INFORMATION: IRGQ forward 02

<400> SEQUENCE: 7
gcgcaggcgc g                                           11

<210> SEQ ID NO 8
<211> LENGTH: 11
<212> TYPE: DNA
<213> ORGANISM: Artificial Sequence
<220> FEATURE:
<223> OTHER INFORMATION: SRRM5 reverse 01

<400> SEQUENCE: 8
gcgcaggcgc g                                           11

<210> SEQ ID NO 9
<211> LENGTH: 11
<212> TYPE: DNA
<213> ORGANISM: Artificial Sequence
<220> FEATURE:
<223> OTHER INFORMATION: SRRM5 forward 01

<400> SEQUENCE: 9
gcgcctgcgc a                                           11

<210> SEQ ID NO 10
<211> LENGTH: 11
<212> TYPE: DNA
<213> ORGANISM: Artificial Sequence
<220> FEATURE:
<223> OTHER INFORMATION: SRRM5 reverse 02

<400> SEQUENCE: 10
gcgcaggcgc g                                           11

<210> SEQ ID NO 11
<211> LENGTH: 11
<212> TYPE: DNA
<213> ORGANISM: Artificial Sequence
<220> FEATURE:
<223> OTHER INFORMATION: SRRM5 forward 02

<400> SEQUENCE: 11
gcgcctgcgc g                                           11

<210> SEQ ID NO 12
<211> LENGTH: 11
<212> TYPE: DNA
<213> ORGANISM: Artificial Sequence
<220> FEATURE:
<223> OTHER INFORMATION: SRRM5 forward 03

<400> SEQUENCE: 12
acgcatgcgc a                                           11

<210> SEQ ID NO 13
<211> LENGTH: 11
<212> TYPE: DNA

```
<213> ORGANISM: Artificial Sequence
<220> FEATURE:
<223> OTHER INFORMATION: FOXA reverse 01

<400> SEQUENCE: 13
gcgcgtgcgc a                                                          11

<210> SEQ ID NO 14
<211> LENGTH: 11
<212> TYPE: DNA
<213> ORGANISM: Artificial Sequence
<220> FEATURE:
<223> OTHER INFORMATION: FOXA3 forward 01

<400> SEQUENCE: 14
gcgcacgcgc c                                                          11

<210> SEQ ID NO 15
<211> LENGTH: 11
<212> TYPE: DNA
<213> ORGANISM: Artificial Sequence
<220> FEATURE:
<223> OTHER INFORMATION: FOXA3 reverse 02

<400> SEQUENCE: 15
gcgcccgccc g                                                          11

<210> SEQ ID NO 16
<211> LENGTH: 11
<212> TYPE: DNA
<213> ORGANISM: Artificial Sequence
<220> FEATURE:
<223> OTHER INFORMATION: FOSB reverse 01

<400> SEQUENCE: 16
gcgcctgcgc a                                                          11

<210> SEQ ID NO 17
<211> LENGTH: 11
<212> TYPE: DNA
<213> ORGANISM: Artificial Sequence
<220> FEATURE:
<223> OTHER INFORMATION: FOSB forward 01

<400> SEQUENCE: 17
gcgcaggcgc g                                                          11

<210> SEQ ID NO 18
<211> LENGTH: 11
<212> TYPE: DNA
<213> ORGANISM: Artificial Sequence
<220> FEATURE:
<223> OTHER INFORMATION: FOSB reverse 02

<400> SEQUENCE: 18
ccgcccgcgc c                                                          11

<210> SEQ ID NO 19
<211> LENGTH: 11
<212> TYPE: DNA
<213> ORGANISM: Artificial Sequence
<220> FEATURE:
<223> OTHER INFORMATION: FOSB reverse 03

<400> SEQUENCE: 19
gcgcccgcgc c                                                          11
```

<210> SEQ ID NO 20
<211> LENGTH: 11
<212> TYPE: DNA
<213> ORGANISM: Artificial Sequence
<220> FEATURE:
<223> OTHER INFORMATION: FOSB forward 02

<400> SEQUENCE: 20
gcgcgggcgc g                                                          11

<210> SEQ ID NO 21
<211> LENGTH: 11
<212> TYPE: DNA
<213> ORGANISM: Artificial Sequence
<220> FEATURE:
<223> OTHER INFORMATION: FOSB forward 03

<400> SEQUENCE: 21
gcgggcgcgc g                                                          11

<210> SEQ ID NO 22
<211> LENGTH: 11
<212> TYPE: DNA
<213> ORGANISM: Artificial Sequence
<220> FEATURE:
<223> OTHER INFORMATION: FOSB reverse 04

<400> SEQUENCE: 22
gcgcgcgcgc c                                                          11

<210> SEQ ID NO 23
<211> LENGTH: 11
<212> TYPE: DNA
<213> ORGANISM: Artificial Sequence
<220> FEATURE:
<223> OTHER INFORMATION: FOSB forward 04

<400> SEQUENCE: 23
gcgcgcgcgc g                                                          11

<210> SEQ ID NO 24
<211> LENGTH: 11
<212> TYPE: DNA
<213> ORGANISM: Artificial Sequence
<220> FEATURE:
<223> OTHER INFORMATION: SIX5 reverse 01

<400> SEQUENCE: 24
gcgcaggcgc a                                                          11

<210> SEQ ID NO 25
<211> LENGTH: 11
<212> TYPE: DNA
<213> ORGANISM: Artificial Sequence
<220> FEATURE:
<223> OTHER INFORMATION: SIX5 forward 01

<400> SEQUENCE: 25
gcgcctgcgc a                                                          11

<210> SEQ ID NO 26
<211> LENGTH: 11
<212> TYPE: DNA
<213> ORGANISM: Artificial Sequence
<220> FEATURE:

```
<223> OTHER INFORMATION: SIX5 reverse 02

<400> SEQUENCE: 26
gcggatgcgc g                                                              11

<210> SEQ ID NO 27
<211> LENGTH: 11
<212> TYPE: DNA
<213> ORGANISM: Artificial Sequence
<220> FEATURE:
<223> OTHER INFORMATION: GPR4 reverse 01

<400> SEQUENCE: 27
gcggatgccc c                                                              11
```